(12) United States Patent
Larsen et al.

(10) Patent No.: US 6,611,766 B1
(45) Date of Patent: Aug. 26, 2003

(54) PROTEOME ANALYSIS FOR CHARACTERIZATION OF UP-AND DOWN-REGULATED PROTEINS IN BIOLOGICAL SAMPLES

(76) Inventors: Peter Mose Larsen, Valmuemarken 46, DK-5260 Odenses (DK); Stephen J. Fey, Vestervang 772, DK-8000 Aarhus C (DK)

( * ) Notice: Subject to any disclaimer, the term of this patent is extended or adjusted under 35 U.S.C. 154(b) by 0 days.

(21) Appl. No.: 09/297,034

(22) PCT Filed: Oct. 24, 1997

(86) PCT No.: PCT/IB97/01337
§ 371 (c)(1),
(2), (4) Date: Jun. 21, 1999

(87) PCT Pub. No.: WO98/19271
PCT Pub. Date: May 7, 1998

Related U.S. Application Data
(60) Provisional application No. 60/030,186, filed on Nov. 5, 1996, provisional application No. 60/029,325, filed on Oct. 25, 1996, and provisional application No. 60/029,324, filed on Oct. 24, 1996.

(30) Foreign Application Priority Data

Sep. 16, 1997 (WO) .................. PCT/IB97/01114

(51) Int. Cl.$^7$ .............. G06F 19/00; G05B 15/00; G01N 27/26; C07K 14/00; C12M 3/00
(52) U.S. Cl. ............ 702/19; 435/287.1; 435/325; 435/348; 435/410; 435/243; 530/350; 700/1; 700/204; 700/450; 702/23
(58) Field of Search .............. 364/413.13; 530/300, 530/350; 435/69.2, 287.1, 325, 348, 410, 243; 204/450; 536/23.1, 24.31, 24.3; 702/19, 23; 700/1

(56) References Cited

U.S. PATENT DOCUMENTS 5,073,963 A 12/1991 Sammons et al.
5,400,249 A 3/1995 Soll et al. .............. 364/413.13

OTHER PUBLICATIONS

Appel, Ron D., et al, "the MELANIE project: from a bopsy to automatic protein map interpretation by computer", Electrophoresis, 1991, 12, pp. 722–735.*
Knecht, M. et al, "Dilated cardiomyopathy: computer-assisted analysis of endomyocardial biopsy protein patterns by 2–D gel electrophoresis", Eur J. Chem Clin Biocfchem, vol. 32, 1994, pp. 615–624.*
Manabe, Takashi, et al, Studies on the procedure for the construction of cellular protein databases employing micro 2–D electrophoresis: an HL–60 protein database, Electrophoresis, 1995, vol. 16, pp. 407–422.*
Microsoft Corporation, Microsoft Excel User's Guide, 1992–93, pp. 305–316.*
Eizirik, D.S., et al, "Role of receptor binding and gene transcription for both the stimulatory and inhibitory effects of interleukin–1 in pancreatic cells", Autoimmunity, 1992, 12(2), pp. 127–33.*
Grunberger, G, et al, "Insulin receptors in normal and disease states", Clinics in Endocrinology and Metabolosim (Mar. 1983), 12(1) pp. 191–219.*
Andersen, H.U. et al., "Genetically determined differences in newborn rat islet sensitivity to interleukin–1 in vitro: no association with the diabetes prone phenotype in the BB–rat," *Acta Endocrinologica* (*Copenh*) 120:92–98 (1989).
Andersen, H.U. et al., "Nicotinamide Prevents Interleukin–1 Effects on Accumulated Insulin Release and Nitric Oxide Production in Rat Islets of Langerhans," *Diabetes* 43(6):770–777 (Jun. 1994).
Andersen, H.U. et al., "Two–Dimensional Gel Electrophoresis of Rat Islet Proteins: Interleukin 1β–Induced Changes in Protein Expression Are Reduced by L–Arginine Depletion and Nicotinamide," *Diabetes* 44(4):400–407 (Apr. 1995).
Christensen, U. B. et al., "Islet Protein Expression at Diabetes Onset in BB–Rats Differs from that Seen During Islet Allograft Rejection," *Diabetologia* 38(1):A85 (abstract 327) (1995).
Eizirik, D.L. et al., "The harmony of the spheres: inducible nitric oxide synthase and related genes in pancreatic beta cells," *Diabetologia* 39(8):875–890 (Aug. 1996).
Garrels, J.I. et al., "The QUEST System for Quantitative Analysis of Two–dimensional Gels," *J. Biol. Chem.* 264(9):5269–5282 (1989).
Giometti, C.S. et al., "Mouse liver protein database: A catalog of proteins detected by two–dimensional gel electrophoresis," *Electrophoresis* 13(12):970–991 (1992).
Helqvist, S. et al., Interleukin 1 induces new protein formation in isolated rat islets of Langerhans, *Acta Endocrinologica* 121(1):136–140 (1989).
Helqvist, S. et al., "Heat shock protein induction in rat pancreatic islets by recombinant human interleukin 1β," *Diabetologia* 34(1):150–156 (1991).
Hughes, J.H. et al., "Interleukin 1 Inhibits Insulin Secretion from Isolated Rat Pancreatic Islets by a Process That Requires Gene Transcription and mRNA Translation,", *J. Clin. Invest.* 86:856–863 (1990).
Jin, J.S. et al., "Shape Representations and Pattern Matching Under the Multi–Channel Theory," *Proceedings of the 3rd Pacific Rim International Conference on Artificial Intelligence*,Beijing China, Aug. 15–18, 1994, vol. 2, pp. 970–975.

(List continued on next page.)

*Primary Examiner*—John S. Brusca
(74) *Attorney, Agent, or Firm*—Sterne, Kessler, Goldstein & Fox P.L.L.C.

(57) ABSTRACT

Methods and computer systems are provided for analyzing cell proteomes to characterize proteins that are up- or down-regulated under different conditions, such as under abnormal or compound treated conditions, including drug screening and testing, as well as proteins and encoding or complementary nucleic acids characterized using such methods and computer systems.

55 Claims, 22 Drawing Sheets

OTHER PUBLICATIONS

Jungblut, P. et al., "Quantitative Analysis of Two-Dimensional Electrophoretic Protein Patterns: Comparison of Visual Evaluation with Computer-Assisted Evaluation," in *Electrophoresis '84* (Volker Neuhoff ed.) Göttingen 1984, pp. 301–303.

Jungblut, P. et al., "Protein analysis on a genomic scale," *J. Biotech.* 41(2–3):111–120 (Jul. 1995).

Karlsen, A. E. et al., "Cloning and Expression of Cytokine-Inducible Nitric Oxide Synthase cDNA from Rat Islets of Langerhans," *Diabetes* 44(7):753–758 (Jul. 1995).

Mandrup-Poulsen, T., "The role of interleukin-1 in the pathogenesis of IDDM," *Diabetologia* 39(9):1005–1029 (Sep. 1996).

Mandrup-Poulsen, T., "Islet Cytotoxicity of Interleukin 1: Influence of Culture Conditions and Islet Donor Characteristics," *Diabetes* 36(5):641–647 (1987).

Martin, J.-P., "Intelligent imaging automates gel analysis for molecular biology," *Scientific Computing World*, pp. 25–28 (Sep. 1995).

O'Farrell, P. H., "High Resolution Two-Dimensional Electrophoresis of Proteins," *J. Biol. Chem.* 250(10):4007–4021 (1975).

O'Farrell, P.Z. et al., "High Resolution Two-Dimensional Electrophoresis of Basic as Well as Acidic Proteins," *Cell* 12(4):1133–1141 (1977).

Shi, C.Z. et al., "Protein Databases for Compacted Eight-Cell and Blastocyst-Stage Mouse Embryos," 37(1):34–47 (1994).

Steiner, S. et al., "Protein variability in male and female Wistar rat liver proteins," *Electrophoresis* 16:1969–1976 (Oct. 1995).

Welsh, N. et al., "Interleukin-1β Increases the Biosynthesis of the Heat Shock Protein hsp 70 and Selectively Decreases the Biosynthesis of Five Proteins in Rat Pancreatic Islets," *Autoimmunity* 9(1):33–40 (1991).

Wilkins, M. R. et al., "From Proteins to Proteomes: Large Scale Protein Identification by Two-Dimensional Electrophoresis and Amino Acid Analysis," *Biotechnology* 14:61–65 (Jan. 1996).

Wilm, M. et al., "Femtomole sequencing of proteins from polyacrylamide gels by nano-electrospray mass spectrometry," *Nature* 379(6564):466–469 (Feb. 1996).

Young, D. S. and Tracy, R. P., "Clinical applications of two-dimensional electrophoresis," *J. Chromatography A* 698:163–179 (1995).

* cited by examiner

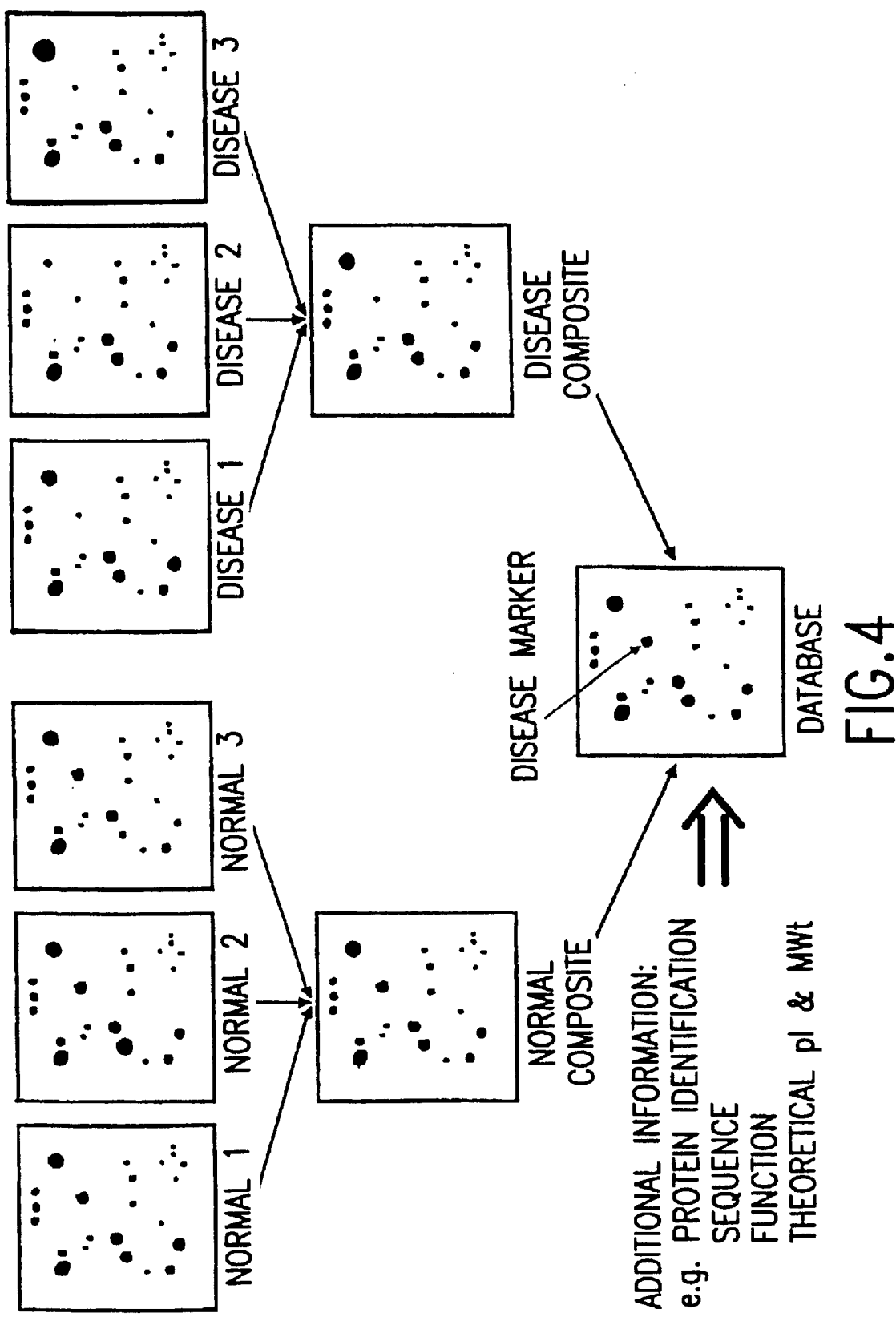

PROTEOME ANALYSIS FOR CHARACTERIZATION OF UP-AND DOWN-REGULATED PROTEINS IN BIOLOGICAL SAMPLES

This application claims the benefit of U.S. Provisional Application No. 60/029,324, filed Oct. 24, 1996, U.S. Provisional Application No. 60/029,325, filed Oct. 24, 1996, and U.S. Provisional Application No. 60/030186, filed Nov. 5, 1996.

BACKGROUND OF THE INVENTION

1. Field of the Invention

The present invention, in the fields of molecular biology and computer image analysis, relates to methods and computer systems for analyzing proteomes of organisms, organs, tissues, biopsies, primary, secondary or established cell lines, and body fluids (serum, plasma, cerebrospinal fluid, urine etc. or culture media) (hereinafter referred to as 'cells')" to characterize cellular and secreted proteins and/or nucleic acids that are up- or down-regulated in affected or unaffected conditions, for diagnostic or therapeutic applications. Proteins characterized using such methods or computer systems are also provided, as well as peptide fragments, and nucleic acids encoding the proteins or fragments, for use in diagnostic applications.

2. Related Art

Proteins and Two Dimensional Gel Electrophoresis. Two-dimensional gel electrophoresis (2-DGE) is a particularly effective tool for separating mixtures of proteins. Cell protein extracts are put onto a gel, and the individual proteins are separated first by charge and then by size. The result is a characteristic picture of as many as 1000 to 5000 spots, each usually a single protein. Resolution can be improved by increasing gel size, and by enhancing the sensitivity through the use of radiolabel methods, silver staining, and the reduction in thickness of the gels to 1.5 mm and less. Jungblut et al., *Journal of Biotechnology* 41:111–120 (1995), have reported that up to 5000 protein spots were run from mouse brain cell extracts on gels of size 23×30 cm.

High resolution 2-DGE has been used for analyzing basic as well as acidic proteins. Isoelectric focusing (IEF) in the first dimension can be combined with sodium dodecylsulfate (SDS) gel electrophoresis in the second dimension (IEF-SDS). Alternatively, NonEquilibrium pH Gradient Electrophoresis (NEPHGE) in the first dimension can be combined with SDS gel electrophoresis in the second dimension (NEPHGE-SDS). Such procedures are described in O'Farrell, *J. Biol. Chem.* 250:4007–4021 (1975) and O'Farrell et al., *Cell,* 12:1133–1142 (1977), which are entirely incorporated herein by reference. NEPHGE gels cannot be used for the determination of isoelectric points of proteins. The isoelectric point of a protein is usually determined in a stable pH gradient with reference to known proteins. As discussed in O'Farrell (1977), good resolution of acidic proteins is obtained with equilibrium IEF. Good resolution of basic proteins can be with a pH 7–10 NEPHGE gel. For the highest resolution of the entire range of proteins, two gels are used: (1) an IEF gel for acidic proteins; and (2) a NEPHGE gel for basic proteins. An alternate method for separating proteins according to pI is to use immobilized pH gradient gel electrophoresis (IPG), according to known method steps.

Once a 2-DGE gel is run, the proteins may be visualized in a variety of ways including staining (Coomasie blue, silver or gold), flourescence (if the sample has been appropriately prepared, e.g. with monobromobimane), or an image captured on X-ray or phosphoimaging plates (if the sample is radioactivly labelled e.g. with [35S]-methionine, [14C]-amino acids, or [32P] phosphate). Stained and flourescent images are captured electronically e.g. using a camera, while X-ray film and phosphor imaging plates are scanned in appropriate devices to yeild the electronic image. For example, after electrophoresis, a 2-DGE gel can be fixed with methanol and acetic acid, treated with AMPLIFY® (Amersham), and dried. The gel is then placed in contact with X-ray film and exposed. The gel can be exposed for multiple time periods to compensate for the lack of dynamic range of X-ray films. Each film image contains a multiplicity of "spots" of differing position, size, shape, and optical density. The spots on the image are analyzed to determine the correspondence between spots and proteins. The use of phosphorimaging technology is preferred because the responce of the phosphorimaging plates is linear and covers a range of 1:100,000 obviating the need for multiple exposures and avoiding the non-linear response of film.

Analysis of 2DGE Gels. Manual visual inspection and analysis of gel images is limited in the number of spots resolvable (Jungblut et al., In: Neuhoff, V. (ed.) *Electrophoresis,* Verlag Chemie GmbH, Weinheim, p. 301–303; (1984); Andersen et al., *Diabetes,* Vol. 44:400–407 (April, 1995)). Additionally, increasing gel size makes visual analysis laborious and time consuming. Analysis of one film can take at least eight to 20 hours, even for one having an expert level of skill and experience in this art. Further, quantification by visual analysis is limited. Typically, visual analysis only detects changes in protein amounts of a factor greater than or equal to 2.

Various computer programs and computer evaluation systems have been developed to improve quantification and assist in evaluation of individual gel films, e.g., PDQUEST (Protein Database Inc., New York), BioImage (Ann Arbor, Mass., USA), Phoretix (Phoretix International, Newcastle, UK), and Kepler (Large Scale Biology Corporation, Rockville, Md.). To use a computer program such as BioImage, the image on the gel film is usually scanned or captured using a digital camera and the digital image entered into the memory or storage of a computer. The digitized gel image is analyzed by the computer program. Each spot is assigned an intensity value, such as an integrated optical density percentage (IOD%), and a position on the gel, such as an "X,Y" Cartesian-type coordinate. Computer programs such as BioImage require the highest qualities in resolution and the highest reproducibility of the spot position. Because the gel medium is so elastic, gel patterns are not identical, i e., two gels, run under essentially identical conditions, will not have each protein spot located in exactly the same position. If two gels are run under conditions that are not essentially the same, then the variations in position of corresponding protein spots will be even greater.

Computer evaluation systems such as those described above have improved the quantification of spot intensities and IOD% for generation of a "spot list" for a gel image. However, computer evaluation systems such as those described above still require significant operator effort for editing. A gel image to be evaluated is input to a computer, such as by scanning. The digitized image is searched to locate spots having an intensity or optical density above a sensitivity threshold. The operator must then edit the gel image. For example, if two very big spots are close together, the computer may have identified the two spots as one elongated spot. The computer may not be able to resolve that there are actually two spots. The operator would then be required to manually edit the image to divide the spot into two spots. As another example, the computer may incorrectly identify as a protein spot a non-protein spot on the gel image, such as a high intensity streak. The operator would then be required to manually edit the image to delete the non-protein spot. It can take from six to eight hours for a skilled operator to edit a gel image evaluated using a conventional computer evaluation system. This manual editing introduces a considerable degree of subjectivity into the analysis and this is the major drawback to the analysis of 2D gel images. Even though attempts can be made to reduce this by having the same operator carry out the entire analysis, there are bound to be differences in how he/she defines spots and how the computer does. This will introduce a degree of error into the analysis.

As reported in Jungblut et al. (1995), numerous researchers have used conventional computer evaluation systems to produce 2-DGE databases for various tissues or cell types. However, these systems require significant effort on the part of the operator to produce an accurate spot list for a new gel image. More importantly, conventional computer evaluation systems do not provide an analysis and interpretation tool that uses information from other gel images of the same cell type to allow an operator to quickly and efficiently analyze and interpret a new gel image. Conventional computer evaluation systems cannot be used to reliably detect proteins only present in small amounts. Thus, there is a need in the art for a computer-based analysis system that reduces the effort required by the operator, and increases the speed with which new gel images can be analyzed and interpreted. There is a further need in the art for a computer-based analysis system for analyzing and interpreting new gel images that uses information from other gel images of the same cell type.

Most conventional computer evaluation systems also do not provide an analysis tool for statistical comparison between groups of gel images. Thus, there is a further need in the art for a computer-based analysis system that is capable not only of analyzing and interpreting a new gel image, but also of executing statistical comparisons between various groups of gel images.

Accordingly, there is a need to provide methods and analysis systems for determining which proteins or nucleic acids are up or down regulated in diseases, as well as methods and systems for testing potential diagnostic or therapeutic compositions and methods for diagnosing or treating such diseases.

SUMMARY OF THE INVENTION

The present invention relates to methods and computer systems for analyzing images of specific cell type proteomes of organisms, organs, tissues, biopsies, primary, secondary or established cell lines, and body fluids (serum, plasma, cerebrospinal fluid, urine etc. or culture media) (hereinafter referred to as 'cells'). The proteomes are analyzed to characterize proteins or nucleic acids that are up- or down-regulated in treated, diseased or immunologically affected conditions. The present invention thus provides such proteins and nucleic acids in purified or isolated form, as well as fragments, probes and related diagnostic and therapeutic compositions and methods.

The invention, in one aspect, provides methods and computer systems for identifying or characterizing unaffected proteins and affected proteins that distinguish normal cells from treated, diseased or immunologically affected cells, in vitro or in vivo, the cells derived from a sample of a specific cell type, or cell lines derived therefrom. The sample can be subjected to two dimensional gel electrophoresis (2DGE) to provide a 2DGE gel comprising the unaffected or affected proteins, as well as recorded images thereof.

These images can be colored or black and white (a colored image can have three grey scale ranges for the primary colors and can thus be analyzed in the same way as described below). For the purposes of this description only, one grey scale is considered although for one skilled in the art, there would be no difficulty to extend the description to the three primary colors, or combinations thereof.

In biotechnology, applications can include, but are not limited to, Northern, Southern or Western blots, one-dimensional gel electrophoresis (1DGE) gels and/or 2DGE gels. The present invention is described below with respect to analyzing gel electrophoresis images to identify proteins and encoding nucleic acids, and to compare gel images to identify changes in protein or nucleic acid expression.

In one aspect of the invention, a method for analyzing images is provided. The method comprises at least one of the following steps, such as, but not limited to (1) to (3), (4), (5), (6), (7), (8), (9), (10), (11) or (12):

(1) capturing a new image, wherein the new image contains a plurality of new image spots corresponding to one or more proteins in an electrophoresis gel, each new image spot having a spot number, an integrated optical density percentage (IOD%) and a position;

(2) generating a master composite image for use in analyzing the new image, wherein the master composite image contains a plurality of master composite spot data list, each master composite spot data list having a spot number, an IOD% and a position;

(3) generating a master composite spot data list, wherein the master composite spot data list comprises the spot number, the IOD%, the position, the variability of the spot (for example the standard deviation expressed as a percentage) for the position and IOD%, and a saturation value (corresponding to the value of the maximum pixel intensity found in any of the spots (from the original images which were used to derive the spot in question) (this value is expressed as a fraction on a scale from white (0) to black (1)) for each of the plurality of master composite spot data list;

(4) generating a database which contains information which might be necessary to interpret the gel images in a meaningful way. This information might include, but is not limited to: the type of sample analysed (including whether it is an organism, an organ, a tissue sample, a biopsy, a body fluid, isolated cells, primary, secondary or from established cell culture; whether it is a total cell extract, a protein containing supernatant or medium produced by cells; the type of cells (including origin, species, age); whether the sample is from a diseased organism or is a control sample for a disease; whether the individual organism or sample has been infected with another organism including any form of microorganism, virus, bacterium, bacteriophage, prion or other infectious agent (and if so which and how and to what extent the infection has progressed); whether the individual organism or sample has been treated with any form of drug or chemical compound (and if so which and how and at what amount); whether the individual organism or sample has been treated with any form of stress or environmental factor which could be expected to influence its response (and if so which and how and at what amount); the manner in which the sample has been collected and treated; information concerning the experiments execution; characteristics of the proteins that have been entered manually or imported from various sources (including the internet), e.g the protein identity, cellular localalisation etc.; or other data that has been generated by analysing some or all of other gel images;

(5) aligning the new image with the master composite image;

(6) selecting a set of anchor points from the master composite spot data list;

(7) detecting new image spots that have a position that is within a position tolerance of the position of corresponding anchor points and that have an IOD% that is within an IOD% tolerance of the IOD% of corresponding anchor points, and matching the detected new image spots to the corresponding anchor points to form a set of matched new image -spots;

(8) calculating a set of vectors linking spots of the same number in the master composite image and in the new gel image; and determining for each vector the length and angle;

(9) calculating a vector difference for each of the set of matched new image spots corresponding to the difference between the vector in question and the vectors originating from a number (for example, 2–500 of the nearest spots to the spot in question. This will generate a vector difference for each of the new matched new image spots and in a subsequent step, removing from the set of matched new image spots those matches for which the vector differences are greater than a predetermined percentage of the best (shortest length and numerically smaller angle) vector differences. A means by which these vector differences can be used to quality check the alignment of the images and to guide the correction of mismatches in a reiterative manner until an optimal match is obtained);

(10) selecting a set of well-defined spots from the master composite spot data list, detecting new image spots that have a position that is within a position tolerance of the position of corresponding well-defined spots, matching the detected new image spots to the corresponding well-defined spots, and adding the matched new image spots to the set of matched new image spots;

(11) selecting a set of saturated spots from the master composite spot data list, detecting new image spots that have a position that is within a position tolerance of the position of corresponding saturated spots, matching the detected new image spots to the corresponding saturated spots, and adding the matched new image spots to the set of matched new image spots;

(12) selecting a set of weak spots from the master composite spot data list, detecting new image spots that have a position that is within a position tolerance of the position of corresponding weak spots, matching the detected new image spots to the corresponding weak spots, and adding the matched new image spots to the set of matched new image spots; and

(13) (optionally replacing step (5) above) searching the new image outside the set of matched new image spots to locate unidentified new image spots.

In another aspect of the present invention, the master composite spot data list or master composite image optionally further comprises at least one characteristic of at least one of said proteins, said characteristic selected from the group comprising pI, molecular weight, amino acid sequence, mass spectra and a post-translational modification.

In another aspect of the present invention, the method further includes comparing a first set of images to a second set of images.

In yet a further aspect of the present invention, the new image is aligned with the master composite image through the use of a common anchor point. Common anchor points correspond to spots present in both the new image and the master composite image. Anchor points selected from the master composite spot data list can include primary anchor points and secondary anchor points. Primary and secondary anchor points are obtained at different stages in the image processing using different selection criteria to select the master composite spot data list proteins to be used.

In still a further aspect of the present invention, well-defined spots have a saturation value S in the range of $0.2<S<0.8$. Saturated spots have a saturation value $S \geq 0.8$. Weak spots have a saturation value $S \leq 0.2$.

In another aspect, a related method of the invention comprises (a) providing at least one recorded image of at least a portion of the 2DGE gel comprising the unaffected or affected proteins, the proteins being resolvable as spots in the protein image;

(b) analyzing the image to identify (i) at least one of the unaffected or affected proteins; (ii) qualitative or quantitative changes in at least one of the affected proteins; (iii) at least one identifying characteristic of at least one of the affected proteins; or (iv) at least one marker protein present in each 2DGE gel from the normal, treated, diseased or immunologically affected cells.

In this method, at least one of the proteins can be selected from the group consisting of unaffected proteins, affected proteins or marker proteins.

The invention, in another aspect provides, methods and computer systems for identifying or characterizing unaffected proteins and affected proteins that distinguish normal cells from treated, diseased or immunologically affected cells, in vitro or in vivo. The sample can be subjected to two dimensional (2D) gel electrophoresis to provide a 2DGE gel comprising the unaffected or affected proteins.

In another aspect, the computer-based system comprises (a) a computer readable medium having stored thereon at least one protein image or protein composite image of at least a portion of the 2DGE gel comprising the unaffected or affected proteins, the proteins being resolvable as spots in the protein image or in the protein composite image;

(b) at least one computing subroutine that, when executed on a computer, causes the computer to analyze the protein image or protein composite image to provide output data representing at least one of the unaffected or affected proteins, the output data optionally further comprising at least one marker image or marker composite image representing at least one marker protein present in each 2DGE gel from the affected and unaffected cells, wherein the protein image or protein composite image, when used to compare images or composite images of the unaffected and affected proteins, identifies (i) qualitative or quantitative changes in at least one of the affected proteins; or (ii) at least one identifying characteristic of at least one of the affected proteins; and (c) retrieval means for recording the output data comprising the protein image or protein composite image, and optionally further comprising (1) data for the marker image or marker composite image; (2) data for the qualitative or quantitative changes; or (3) data for said at least one characteristic.

In a further aspect, the invention provides a computer method, comprising (a) providing a computer readable medium having stored thereon at least one protein image or protein composite image of at least a portion of the 2DGE gel comprising the unaffected or affected proteins, the proteins being resolvable as spots in the protein image or in the protein composite image;

(b) analyzing, on a computer using at least one computing subroutine executed in the computer, the at least one protein image or protein composite image to provide output data representing at least one of the unaffected or affected proteins, the output data optionally further comprising at least one marker image or marker composite image representing at least one marker protein present in each 2DGE gel from the normal, treated, diseased or immunologically affected cells, wherein the protein image or protein composite image, when used to compare images or composite images of the unaffected and affected proteins, identifies (i) qualitative or quantitative changes in at least one of the affected proteins; or (ii) at least one identifying characteristic of at least one of the affected proteins; and (c) obtaining the output data comprising the protein image or protein composite image, and optionally further comprising at least one of (1) data for the marker image or marker composite image; (2) data for the qualitative or quantitative changes; or (3) data for the at least one characteristic.

In the above computer system or method, the at least one characteristic of at least one of said proteins can be characterised in a number of ways including but not limited to protein identity, pI, molecular weight, amino acid sequence, IOD%, mass spectra or a protein modification.

The invention also provides computer readable media comprising output data provided by the above computer system of method.

In preferred embodiments, computer systems or methods of the present invention are provided where the treated cells have been treated with at least one compound prior to providing the cell sample. The compound, such as a chemical or a biological molecule, can be a potential diagnostic or therapeutic compound.

In methods, computer systems or gels of the present invention, qualitative changes can be changes in the structure of at least one of said proteins in said 2DGE gel, and quantitative changes can be changes in the amount of at least one of said proteins in said 2DGE gel.

In methods, computer systems or gels of the present invention, at least one characteristic can be selected from the group consisting of pI, molecular weight, %IOD, amino acid sequence, mass spectra and a protein modification.

In methods, computer systems or gels of the present invention, the cell type or cell line can be derived from a prokaryotic or eukaryotic cell, and it is preferred that the eukaryotic cell is a mammalian cell or bird cell.

In methods, computer systems or gels of the present invention, the treated cells can have been treated with at least one compound prior to providing said cell sample, where a preferred compound is selected from the group consisting of a protein, a nucleic acid and a chemical compound, and a more preferred compound can be a potential drug.

According to the present invention, at least one purified protein is provided by the present invention, where the protein corresponds to a protein identified or characterized by methods, computer systems or gels of the present invention.

It is a feature of the present invention that it can analyze and interpret new gel images, and also conduct statistical comparisons between groups of gel images.

It is a further feature of the present invention that it uses information from a single gel (using default tolerance values) or a master composite image to guide the analysis and interpretation of new gel images.

It is yet a further feature of the present invention that it uses the integrated optical density percentage, as well as the position, in locating spots in new gel images.

It is an advantage of the present invention that new gel images can be analyzed and interpreted with minimal input from an operator.

It is a further advantage of the present invention that new gel images can be analyzed and interpreted quickly and efficiently.

It is a still further advantage of the present invention that if can reliably detect proteins that are present in small amounts.

It is yet a further advantage of the present invention that it is not limited to analysis and interpretation of two-dimensional gel electrophoresis images, and can be used to compare any two similar images, whether black and white or color or in any situation where image interpretation and recognition is involved. This process could include the comparison of "freshly derived images" from any image capture device with an image recovered from a computer memory device.

Other objects of the invention will be apparent to skilled practitioners from the following detailed description and examples relating to the present invention.

BRIEF DESCRIPTION OF THE FIGURES

FIG. 4: is flow diagram showing a statistical approach by which a disease-related protein (i.e., a protein exhibiting an altered expresion related to treatment. disease or immunological condition) is selected or identified by a method according to the present invention. Gel images labeled "normal 1," "normal 2" and "normal 3" are from gels of proteomes from a normal control cell. Gel images labeled "disease 1," "disease 2" and "disease 3" are from gels from affected cells as a disease cell. A gel image master composite spot data list (labeled "normal composite") is a composite of control images containing statistical values of the variability of each normal or control protein. A gel image master composite spot data list (labeled a "disease composite") is a composite of disease or affected images containing statistical values of the variability of each disease or affected protein. The bottom gel image labeled "database" comprises a statistical comparison between the normal composite and the disease composite in order to identify those proteins which are affected by the disease, treatment or immunologically affected state.

DETAILED DESCRIPTION OF THE PREFERRED EMBODIMENTS

Figure 1:
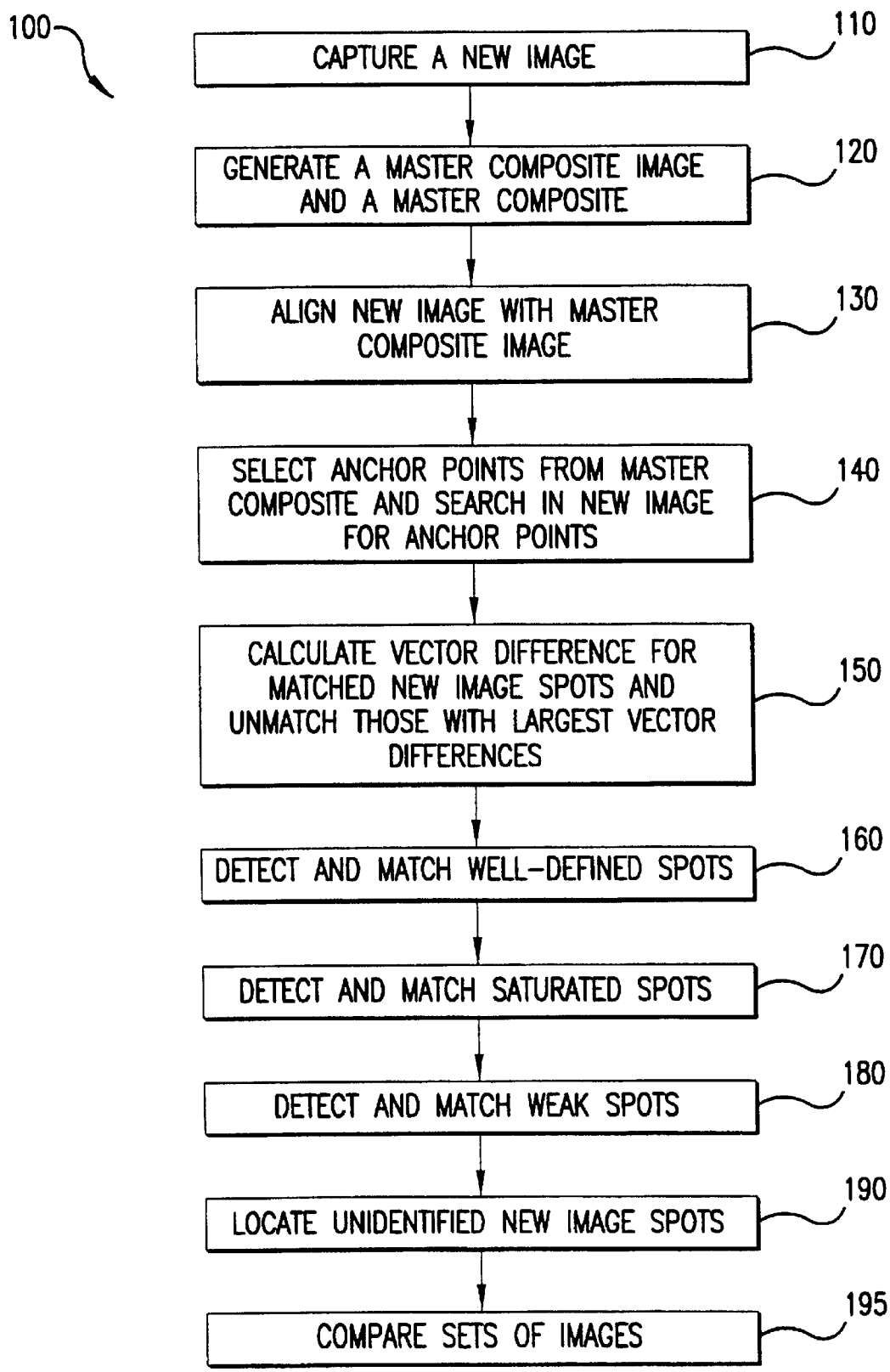
FIG. 1 shows a block diagram illustrating one embodiment of a method of the present invention.

The present invention relates to methods and computer systems for analyzing proteomes of tissues, biopsies, cell lines, and body fluids (sera plasma cerebrospinal fluid, urine, etc.) to characterize cellular and secreted proteins and nucleic acids that are up- or down-regulated in unaffected (e.g., normal) or affected (e.g. treated, diseased, and/or immunologically affected) conditions, for either diagnostic or therapeutic applications. Proteins characterized using such methods or computer systems are also provided in purified or isolated form.

In the context of the present invention, the term "protein" includes proteins, polypeptides, and peptides which are chains of amino acids, including all modifications (e.g., processing and truncations, glycosylations, phosphorylations or any other modification). The term also encompasses natural proteins as well as synthetic or recombinant proteins, polypeptides, and peptides.

The term "affected protein" means a protein that is modified in expression or modified structurally. An affected protein can thus be a protein whose expression is modified due to treatment with one or more compounds, a diseased or pathological state and/or an immunological change in or outside the cell from which the protein is derived. An affected protein can alternatively or additionally also be a protein which exhibits an altered expression as up- or down-regulated, or whose expression is modified in structure in any way that can be detected by a method of the present invention, as compared to the the expression of the same protein (i.e., an "unaffected protein") in the absence of such treatment, disease or immunological change.

The term "protein modification" includes any change in structure (i.e., a qualititive change) of a protein. Such modifications can include, but are not limited to, changes in the amino acid sequence, transcriptional or translational splice variation, pre- or post-translational modifications to the DNA or RNA sequence, addition of macromolecules or small molecules to the DNA, RNA or protein, such as peptides, ions, vitamins, atoms, sugar-containing molecules, lipid-containing molecules, small molecules and the like, as well-known in the art.

One type of protein modification according to the present invention is by one or more changes in the amino acid sequence (substitution, deltion or insertion). Such changes could include, at one or more amino acids, a change from a charged amino acid to a different charged amino acid, a non-charged to a charged amino acid, a charged amino acid to a non-charged amino acid (e.g., giving rise to possible differences in pI or molecular weight). Any other change in amino acid sequence is also included in the invention. The overall positional change in a gel of a modified protein with a changed amino acid sequence also depends on how many overall charges there are in the protein, as known in the art. Changes in the resolution of the gel (e.g., changing the pH or other gradient component) of the gel can allow detection of minor or major amino acid sequence changes. The type of analysis can also affect how changes are detected, e.g., using sequencing, mass spectrometry, labeled antibody binding.

Another type of modification is by change in length, conformation, splicing or orientation in the protein-encoding DNA or RNA that affects the way the open reading frame is read in the cell, which can give large changes in position of the spot on the gel and which could affect the analysis of the protein type and position in the gel.

Another type of protein modification is by changes in processing of the protein in the cell. A non-limiting example is where some proteins have an "address label" specififying where in (or outside of) the cell they should be used. Such a label or tag can be in the form of a peptide, a sugar or a lipid, which when added or removed from the protein, determines where the protein is located in the cell.

A further type of protein modification is due to the attachment of other macromolecules to a protein. This group can include, but is not limited to, any addition/removal of such a macromolecule. These molecules can be of many types and can be either permanent or temporary. Examples include: (i) polyribosylation, (ii) DNA/RNA (single or double stranded); (iii) lipids and phosphlipids (e.g., for membrane attachment); (iv) saccharides/polysaccharides; and (v) glycosylation (addition of a multitude of different types of sugar and sialic acids—in a variety of single and branched structures so that the number of variations possible is large).

Another type of protein modification is due to the attachment of other small molecules to proteins. Examples can include, but are not limited to: (i) phosphorylation; (ii) acetylation; (iii) uridylation; (iv) adenylation; (v) methylation, and (vi) capping (diverse complex modification of the N-terminus of the protein for assorted reasons). Most of these changes are often used to regulate a protein's activity. (v) and (vi) are also used to change the half-life of the protein itself. These protein changes can be detected by 2D using several methods, such as labeling, changes in pI, antibodies or other specific techniques directed to the molecules themselves, as known in the art. Molecular weight changes can be, but may not usually be detectable by 2DGE. MALDI (matrix assisted laser desorption/ionisation time of flight mass spectrometry) is preferred to detect and characterize these modifications.

The term "expression" is meant to include not only the physical expression of a protein, but also as a measure of the activity of an expressed protein. For example, a protein can be expressed as an inactive form, which is activated by phosphorylation. While the actual expression of the protein has not changed, its effective expression (activity) has been modified. On a gel, the change in activity may be measured as the change in expression of a modified form of the protein.

The term "substantially pure," when referring to a polypeptide, means a polypeptide that is at least 60%, by weight, free from the proteins and naturally-occurring organic molecules with which it is naturally associated. A substantially pure protein is at least 75%, more preferably at least 90%, and most preferably at least 99%, by weight, protein. A substantially pure protein can be obtained, by extraction from a natural source; by expression of a recombinant nucleic acid encoding a protein, or by chemically synthesizing the protein. Purity can be measured by any appropriate method, e.g., column chromatography, polyacrylamide gel electrophoresis, or HPLC analysis.

As used herein, "polynucleotide" refers to a nucleic acid sequence of deoxyribonucleotides or ribonucleotides in the form of a separate fragment or a component of a larger construct. DNA encoding portions or all of the polypeptides of the invention can be assembled from cDNA fragments or from oligonucleotides that provide a synthetic gene which can be expressed in a recombinant transcriptional unit. Polynucleotide sequences of the invention include DNA, RNA, and derivatives using modified nucleotides, and can be derived from natural sources or synthetic sequences synthesized by methods known to the art.

As used herein, an "isolated" polynucleotide is a polynucleotide that is not immediately contiguous (i.e., covalently linked) with either of the coding sequences with which it is immediately contiguous (i.e., one at the 5' end and one at the 3' end) in the naturally-occurring genome of the organism from which the polynucleotide is derived. The term therefore includes, for example, a recombinant polynucleotide which is incorporated into a vector, into an autonomously replicating plasmid or virus, or into the genomic DNA of a prokaryote or eukaryote, or which exists as a separate molecule independent of other sequences. It also includes a recombinant DNA which is part of a hybrid gene encoding additional polypeptide sequences.

The isolated and purified polynucleotide sequences of the invention also include polynucleotide sequences that hybridize under stringent conditions to the polynucleotide sequences specified herein. The term "stringent conditions" means hybridization conditions that guarantee specificity between hybridizing polynucleotide sequences. One skilled in the art can select posthybridization washing conditions, including temperature and salt concentrations, which reduce the number of nonspecific hybridizations such that only highly complementary sequences are identified (Sambrook et al. in *Molecular Cloning*, 2d ea.; Cold Spring Harbor Laboratory Press, Cold Spring Harbor, N.Y. (1989), hereby specifically incorporated by reference). For instance, such conditions are hybridization under specified conditions, e.g. involving presoaking in 5×SSC and prehybridizing for 1 h at about 40° C. in a solution of 20% formamide, 5×Denhardt's solution, 50 mM sodium phosphate, pH 6.8, and 50 μg of denatured sonicated calf thymus DNA, followed by hybridization in the same solution supplemented with 100 μM ATP for 18 h at about 40° C. (Sambrook et al. supra (1989)). The isolated and purified polynucleotide sequences of the invention also include sequences complementary to the polynucleotide encoding a diabetesmediating protein (antisense sequences) and ribozymes.

By "altered protein" or "altered protein expression" is meant proteins whose expression is changed quantitatively, as increased ("up regulated"), decreased ("down regulated"), inhibited (i.e., turned off) or induced (i.e., turned on) in response to treatment, disease and/or an immunological change.

Computer Based Methods and Systems for Analyzing Gel Images

The present invention is directed in one aspect toward a computer-based process for analyzing images. The present invention will be described in the context of analyzing two-dimensional gel electrophoresis (2DGE) images. However, it is to be understood that the present invention is not limited to analysis of 2DGE images, and can be used to compare any two similar images, whether black and white or color or in any situation where image interpretation and recognition is involved. This process could include the comparison of "freshly derived images" from any image capture device with an image recovered from a computer memory device. Examples of such images could include but are not restricted to: tissue sections, gel or blot images of proteins, RNA or DNA.

The method of the present invention provides an analysis tool for analyzing and interpreting gel images quickly and efficiently with minimal operator input. The gel images are analyzed and interpreted by computer analysis so that new proteins can be identified. The method of the present invention also provides a comparison tool for comparing gel images to identify changes in proteins, ie., up- or down-regulation, for affected or unaffected proteins.

The method of the present invention uses information from a master composite image to guide the analysis of new gel images. In this manner, information from other gel images of the same cell type can be used to guide the analysis and interpretation of a new gel image. This technique reduces significantly the time required to analyze a new gel image. This technique also reduces significantly the operator effort and interpretation that is required to analyze a new gel image.

To carry out a method of the present invention, a master composite image is generated from images selected by an operator or user. The images selected by the operator for use in generating the master composite image would typically be of the same cell type, and would be relevant to the type of project or experiment being conducted. As used herein, "image" refers to a representation that is composed of pixels, each pixel having a grey level unit-less value assigned to it. For example, each pixel in an 8-bit image would have a grey level assigned to it ranging from zero (white) to 255 (black) and a saturation value (a value which varies from zero to 1, corresponding to the value of the darkest pixel of each spot divided by 255 (for 8 bit images)), and the standard deviation of the X,Y (positional) and Z (quantitation values for each spot when the spot has been matched to more than one gel. An image with a higher number of bits would have a larger range of grey levels with finer steps.

A master composite spot data list is generated that corresponds to the master composite image. As explained in more detail below, the master composite spot data list includes data that represent characteristics of each spot on the master composite image, such as, but not limited to, spot position, the integrated optical density percentage (IOD%), a spot number, and a saturation value. The master composite spot data list provides a compilation of data that can be readily searched to aid in the analysis and interpretation of the new image. When a spot in the new image is located that corresponds to a spot in the master composite spot data list, the located new image spot is "matched" to the spot in the master composite spot data list. Once a master composite spot data list is matched to a new image spot, it is removed from the available pool of master composite spot data list. The method of the present invention iterates through a series of searches to match all of the master composite spot data list to new image spots. Any unmatched spots that are present in the new image after all of the master composite spot data list are matched represent unidentified new image spots. Such unidentified new image spots can represent previously unidentified proteins.

In another application of the present invention, different exposures of the same image of different gels of the same sample can be matched together so that it is possible to "extend the dynamic range" of the medium from which the image is read. This medium is typically, but not restricted to: X-ray film, photographs, video recordings, digital recordings, or any other recording of chemically stained gels, immuno-stained gels or blots thereof, or combinations or variations of these. This procedure is often useful because: the ratio of expression of proteins within a cell is greater than 100,000 (e.g., exceeding the dynamic range of response of X-ray film which is about 100–1,000 or stained gels which have a dynamic range of approximately 10–100); or because the response of the said medium is not linear (which introduces problems in accurate quantitation of the protein spots).

Once the master composite image is generated, a new image can be aligned to it. The method of the present invention aligns the new image to the master composite image through the use of anchor points. The anchor points include common anchor points that correspond to spots present in both the new image and the master composite image, and primary and secondary anchor points that are selected from the master composite spot data list based upon defined criteria. A vector differencing quality control analysis is carried out to ensure that the anchor points are properly matched to new image spots.

The method of the present invention carries out a search in the new image for three different types of spots present in the master composite spot data list that have not already been matched. The first type of spot is a "well-defined" spot. As explained more fully below, a well-defined spot is one having a saturation value "S" that is between about 0.2 and about 0.8. Well-defined spots are those spots that are not weak or saturated. The second type of spot is a "saturated" spot. A saturated spot has a saturation value S that is greater than or equal to 0.8. The third type of spot is a "weak" spot. A weak spot has a saturation value that is less than or equal to 0.2. Spots located in the new image that correspond to the well-defined, saturated, and weak spots are matched, and given the same spot number as the corresponding master composite spot data list.

Once the search for the well-defined, saturated, and weak spots is complete, the new image outside of the matched new image spots is searched to locate unidentified spots. The unidentified spot search is carried out using two different sensitivity levels. The unidentified spots that are located are presented to the operator for further analysis and evaluation.

In another application of the present invention, different exposures of the same image can be matched together using the same procedures outlined above and described in detail below if the user specifies that the new gel and the images selected as the MCI are either of the same gel or of the same sample. Following the combination of two or more images in these categories, the %IOD are recalculated and these values are used for further analysis.

The method of the present invention as described above provides an efficient analysis tool for analyzing and interpreting new images. The method of the present invention provides the additional capability of comparing various images that have previously been interpreted. For example, an operator can identify two or more groups of images to be compared, such as one group of cells treated in a particular manner, and one group of untreated cells. Each spot in the treated-cell group of gel images is compared to the corresponding spot in the untreated-cell group of gel images to see if there is a statistically significant difference. This provides a convenient way for an operator to do statistical comparison between selected images.

Turning now to FIG. 1, a block diagram 100 is shown that illustrates one embodiment of the method of the present invention. As explained more fully below, the invention can be implemented using hardware, software, or a combination thereof, and can be implemented in a computer system or other processing system. In a step 110, a new image is captured. It is to be understood that the present invention is not limited to a new image being a 2DGE gel image, so that the present invention can be used to analyze any suitable type of image. The image can be captured by scanning the image into a computer in a manner known to one of skill in the relevant arts. The image can also be captured by recovering it from a storage device, such as a random access memory (RAM), read only memory (ROM), hard disk drive, flash memory, optical disk, floppy disk, etc. The image can also be captured by downloading it via a communications interface from another computer, camera, from a site via the INTERNET, or from any other source.

In a step 120, a master composite image and a master composite spot data list are generated and the type of analysis is selected (matching of new gel to master composite spot data list, two exposures of the same gel or two gels of the same sample). In a step 130, the new image is aligned with the master composite image.

In a step 140, anchor points are selected from the master composite spot data list. The new image is searched to locate in the new image spots that correspond to the anchor points. If a spot is located in the new image that corresponds to the anchor point, the new image spot is matched to the corresponding anchor point.

In a step 150, a vector difference is calculated for each matched new image spot. The matched new image spots that have the largest vector differences are unmatched.

In a step 160, the new image is searched to detect and match well-defined spots. In a step 170, the new image is searched to detect and match saturated spots. In a step 180, the new image is searched to detect and match weak spots.

In a step 190, the new image is searched to locate unidentified new image spots. The new image is searched outside of the spots that have already been matched.

If, at the beginning of the procedure (step 120) the user has selected that the gels being matched were either two exposures of the same gel or two gels of the same sample, then the computer recalculations the %IOD for all proteins.

Finally, in a step 195, various sets of images can be compared. An operator can select groups of images to be compared, as well as the type of statistical comparison to be done.

From the description of the operation of the present invention contained herein, and the associated flowcharts, it would be readily apparent to a programmer or molecular biologist skilled in the relevant arts how to implement the present invention using a computer program that controls operation of a computer system or processor. A programmer skilled in the relevant arts could, for example, provide a computer program to implement the method of the present invention using, as a non-limiting example, the C++ programming language, or any other suitable language as well known in the art.

In preferred embodiments, computer systems or methods of the present invention are provided where the treated cells have been treated with at least one compound prior to providing the cell sample, irrespective of whether the same is derived from a tissue, biopsy, isolated cells or cell culture; or whether the proteins to be analysed are cellular or secreted. The compound, such as a chemical or a biological molecule, can be a potential diagnostic or therapeutic compound.

Implementation of the Present Invention

Figure 2:
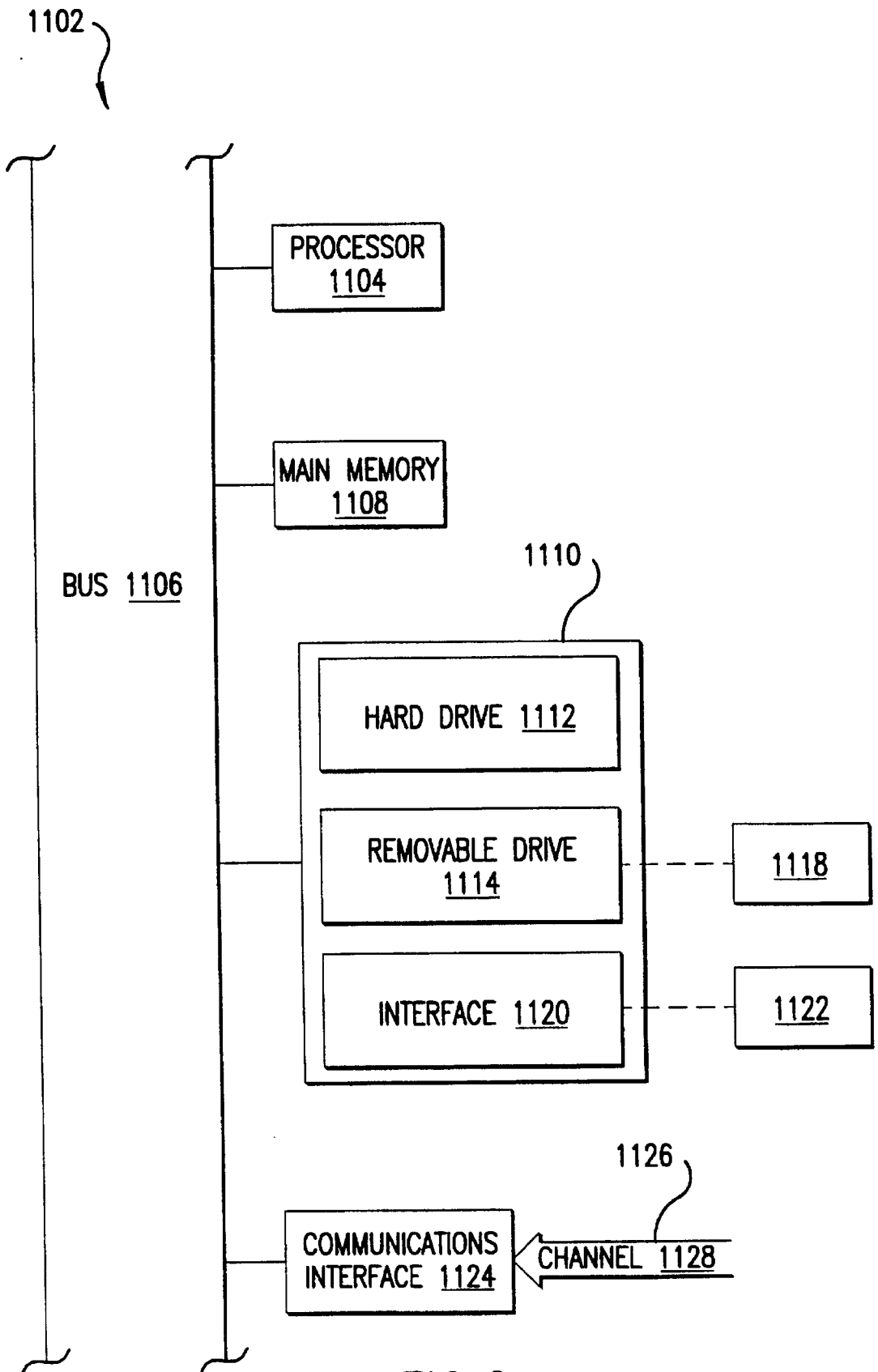
FIG. 2 shows a block diagram for an exemplary computer system suitable for use with the present invention.
Figure 3:
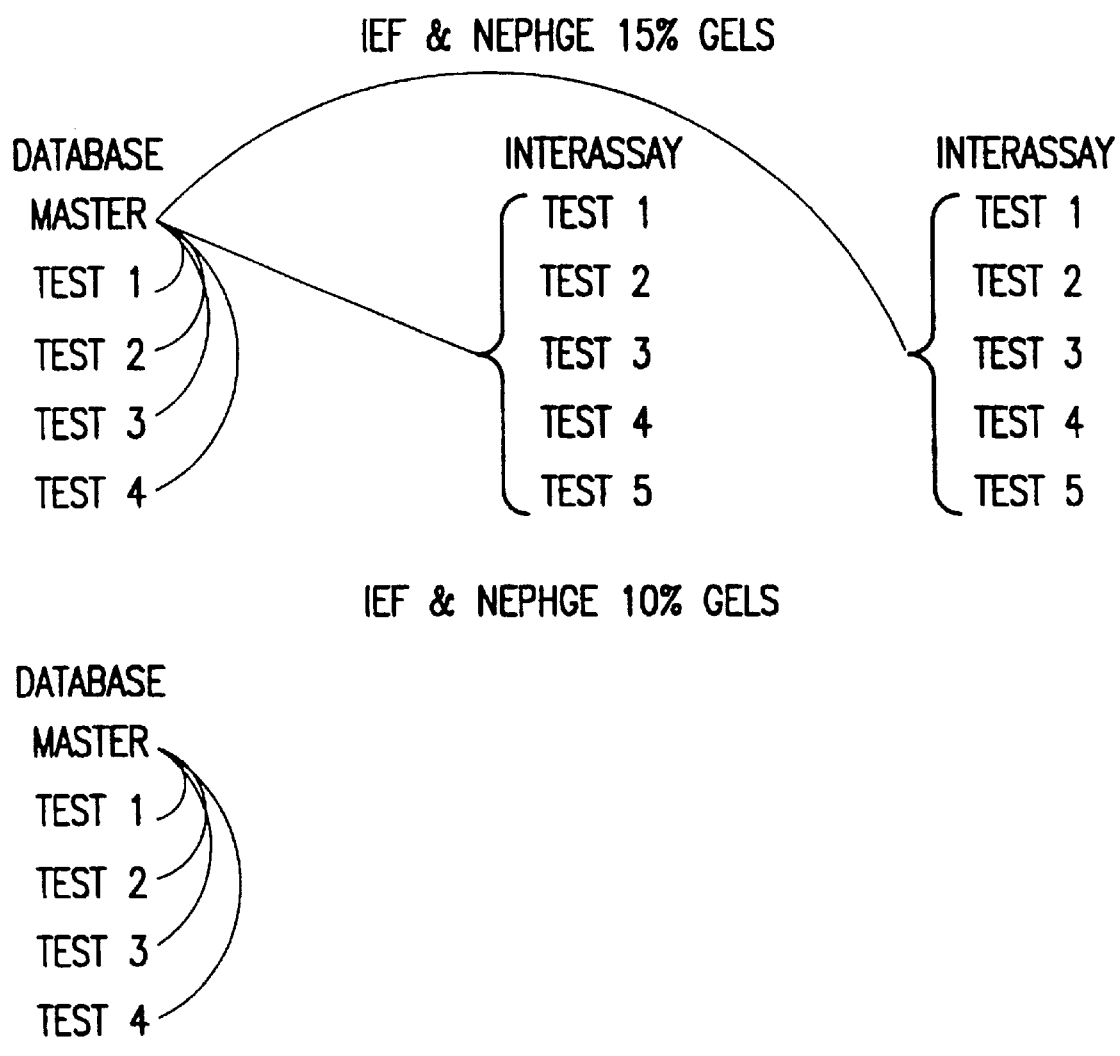
FIG. 3: Design of database, intra- and interassay analysis. Database analysis was performed for each of the 4 subgroups: 10% IEF, 15% IEF, 10% NEPHGE and 15% NEPHGE, while intra- and interassay analysis was only performed for 15% IEF and 15% NEPHGE. Each database consists of 5 different islet isolates, analyzed in one set of gels. Intraassay analysis consists of 5 gels of the same sample analyzed in one set of gels, whereas interassay analysis consists of 5 gels of the same sample analyzed in consecutive sets of gels on different days. Different isolates were used for database, intra and interassay analysis. Before computer analysis, one gel in each subgroup was arbitrarily selected to be the "master gel" used for comparison with the other 4 database gels, the 5 intraassay gels and the 5 interassay gels. The database "master gel" was used as a master for intra- and interassay analysis to ensure that a given spot had the same match number in the three series of analyses. Data from the "master gel" are only included in the database analysis. The "master gel" was from the same isolate in all 4 subgroups, whereas the identity of the isolates producing the 4 other database gels varied slightly from subgroup to subgroup (Table 3).

As noted above, the invention may be implemented using hardware, software or a combination thereof, and may be implemented in a computer system or other processing system. In one embodiment, the invention is directed toward a computer system capable of carrying out the functionality described herein. An exemplary computer system 1102 is shown in FIG. 2. Computer system 1102 includes one or more processors, such as processor 1104. Processor 1104 is connected to a communication bus 1106. Various software embodiments are described in terms of this exemplary computer system. After reading this description, it will become apparent to a person skilled in the relevant art how to implement the invention using other computer systems and/or computer architectures.

Computer system 1102 also includes a main memory 1108, preferably random access memory (RAM), and can also include a secondary memory 1110. Secondary memory 1110 can include, for example, a hard disk drive 1112 and/or a removable storage drive 1114, representing a floppy disk drive, a magnetic tape drive, an optical disk drive, etc. Removable storage drive 1114 reads from and/or writes to a removable storage unit 1118 in a well known manner. Removable storage unit 1118, represents a floppy disk, magnetic tape, optical disk, etc. which is read by and written to by removable storage drive 1114. As will be appreciated, removable storage unit 1118 includes a computer usable storage medium having stored therein computer software and/or data.

In alternative embodiments, secondary memory 1110 may include other similar means or memory devices for allowing computer programs or other instructions to be loaded into computer system 1102. Such memory devices can include, for example, a removable storage unit 1122 and an interface 1120. Examples of such can include a program cartridge and cartridge interface (such as that found in video game devices), a removable memory chip (such as an EPROM, or PROM) and associated socket, and other removable storage units 1122 and interfaces 1120 which allow software and data to be transferred from removable storage unit 1122 to computer system 1102.

Computer system 1102 can also include a communications interface 1124. Communications interface 1124 allows software and data to be transferred between computer system 1124 and external devices (not shown), such as a scanning device for inputting gel images into computer system 1102. Examples of communications interface 1124 can include a modem, a network interface (such as an Ethernet card), a network interface suitable for interfacing with the INTERNET, a communications port, a PCMCIA slot and card, etc. Software and data transferred via communications interface 1124 are in the form of signals 1126 which can be electronic, electromagnetic, optical or other signals capable of being received by communications interface 1124. Signals 1126 are provided to communications interface via a channel 1128. Channel 1128 carries signals 1126 and can be implemented using wire or cable, fiber optics, a phone line, a cellular phone link, an RF link and other communications channels.

In this document, the terms "computer program medium," "computer program product," "program storage device," and "computer usable medium" are used to generally refer to media such as removable storage device 1118, a hard disk installed in hard disk drive 1112, and signals 1126. These computer program products provide software to computer system 1102.

Computer programs (also called computer control logic) are stored in main memory and/or secondary memory 1110. Computer programs can also be received via communications interface 1124. Such computer programs, when executed, enable the computer system 1102 to perform the features of the present invention as discussed herein. In particular, the computer programs, when executed, enable processor 1104 to perform the features of the present invention. Accordingly, such computer programs represent controllers of computer system 1102.

In an embodiment where the invention is implemented using software, the software may be stored in a computer program product and loaded into computer system 1102 using removable storage drive 1114, hard drive 1112 or communications interface 1124. The control logic (software), when executed by processor 1104, causes processor 1104 to perform the functions of the invention as described herein.

In another embodiment, the invention is implemented primarily in hardware using, for example, hardware components such as application specific integrated circuits (ASICs). Implementation of the hardware state machine so as to perform the functions described herein will be apparent to persons skilled in the relevant art(s).

In yet another embodiment, the invention is implemented using a combination of both hardware and software.

Affected and Unaffected Proteins, and Encoding Nucleic Acids, Provided by the Present Invention. Certain up and/or down regulated proteins—corresponding to affected, diseased, treated or immunologically affected peptides of the invention—are now discovered using methods of the present invention. The present invention thus provides affected, diseased or unaffected peptides and/or encoding or complementary nucleic acid, as well as methods of making and using thereof, including recombinant expression, purification and drug screening, utilizing at least one affected or unaffected peptide amino acid sequence or encoding or complementary nucleic acid.

Affected or Unaffected Peptides or Proteins as. An affected or unaffected peptide can refer to any subset of an affected or unaffected peptide, protein or modified peptide or protein, as a fragment, consensus sequence or repeating unit, thereof. An affected or unaffected protein or peptide of the invention can be prepared by:

(a) recombinant DNA methods;

(b) proteolytic digestion of the intact molecule or a fragment thereof, and (c) by any other method capable of producing an affected or unaffected protein or peptide. The affected or unaffected peptide can have biological activity that can be screened according to known screening assays, in vitro, in situ, in silico or in vivo. The minimum peptide sequence to have activity is based on the smallest unit containing or comprising a particular region, domain, consensus sequence, or repeating unit thereof, of at least one affected or unaffected peptide.

According to the invention, an affected or unaffected peptide includes an association of two or more polypeptide domains, such as transmembrane, cytoplasmic, hydrophobic, hydrophilic, ligand binding, or pore lining domains, or fragments thereof, corresponding to an affected or unaffected peptide, such as 1–40 domains or any range or value therein. The peptide can further comprise any modification as defined herein or as known in the art. As would be understood by one of ordinary skill in the art, the above configuration of domains are provided as part of an affected or unaffected peptide of the invention, such that a functional affected or unaffected protein or peptide, when expressed in a suitable cell, is capable of the associated biological activity found in that affected cell type. Such activity, as measured by suitable affected or unaffected protein or peptide activity assays, establishes affected or unaffected protein or peptide activity of one or more affected or unaffected proteins or peptides of the invention.

In one aspect, such an affected or unaffected peptide can maintain affected or unaffected protein or peptide biological activity. It is preferred that an affected or unaffected peptide of the invention is not naturally occurring or is naturally occurring but is in a purified or isolated form which does not occur in nature.

Thus, one of ordinary skill in the art, given the teachings and guidance presented in the present specification, will know how to add, delete or substitute other amino acid residues in other positions of an affected or unaffected protein or peptide to obtain an affected or unaffected peptide, including substituted, deletional or additional variants, as known in the art.

An affected or unaffected protein or peptide of the invention also includes a variant wherein at least one amino acid residue in the peptide has been conservatively replaced, added or deleted by at least one different amino acid. For a detailed description of protein chemistry and structure, See, e.g., Schulz, et al., *Principles of Protein Structure,* Springer-Verlag, New York, 1978, and Creighton, T. E., *Proteins: Structure and Molecular Properties,* W. H. Freeman & Co., San Francisco, 1983, which are hereby incorporated by reference. For a presentation of nucleotide sequence substitutions, such as codon preferences, see Ausubel et al., eds, *Current Protocols in Molecular Biology,* Greene Publishing Assoc., New York, N.Y. (1987, 1992, 1993, 1994, 1995) at §§ A.1.1–A.1.24, and Sambrook et al, *Molecular Cloning: A Laboratory Manual,* Second Edition, Cold Spring Harbor Press, Cold Spring Harbor, N.Y. (1989), at Appendices C and D.

Accordingly, alternative substitutions can be made by routine experimentation, to provide alternative affected or unaffected proteins or peptides of the invention, e.g., by making one or more conservative substitutions of affected or unaffected protein or peptide fragments which provide affected or unaffected protein or peptide activity. However, when the exact effect of the substitution, deletion, or addition is to be confirmed, one skilled in the art will appreciate that the effect of at least one substitution, addition or deletion will be evaluated by at least one activity screening assay, such as, but not limited to, immunoassays or bioassays, to confirm biological activity. The samples of the invention include cells, protein extracts or membrane extracts of cells, or biological fluids. The sample will vary based on the assay format, the detection method and the nature of the tissues, cells or extracts used as the sample.

The cells and/or tissue can include, e.g., normal or pathologic animal cells or tissues and extracts or cell cultures thereof, provided in vivo, in situ or in vitro, as cultured, passaged, non-passaged, transformed, recombinant, or isolated cells and/or tissues.

A variety of methodologies known in the art can be utilized to obtain an isolated affected or unaffected peptide of the invention. In one embodiment, the peptide is purified from tissues or cells which naturally produce the peptide. Alternatively, the above-described isolated nucleic acid fragments could be used to expressed the affected or unaffected peptide protein in any organism.

Any higher eukaryotic organism can be used as a source of at least one affected or unaffected peptide of the invention, as long as the source organism naturally contains such a peptide. As used herein, "source organism" refers to the original organism from which the amino acid sequence of the peptide is derived, regardless of the organism the peptide is expressed in and/or ultimately isolated from. Preferred organisms as sources of at least one affected or unaffected peptide or encoding nucleic acid can be any vertebrate animal, such as a mammal or a bird. Among mammals, the preferred recipients are mammals of the Orders Primata (including humans, apes and monkeys), Arteriodactyla (including horses, goats, cows, sheep, pigs), Rodenta (including mice, rats, rabbits, and hamsters), and Carnivora (including cats, and dogs). The most preferred organisms are humans.

One skilled in the art can readily follow known methods for isolating proteins in order to obtain the peptide free of natural contaminants. These include, but are not limited to: inmnunochromotography, size-exclusion chromatography, HPLC, ion-exchange chromatography, and immunoaffinity chromatography. See, e.g., Ausubel, infra; Sambrook, infra; Colligan, infra.

Isolated Nucleic Acid Molecules Coding for Affected or Unaffected Peptides. In one embodiment, the present invention relates to an isolated nucleic acid molecule coding for a peptide having an amino acid sequence corresponding to novel affected or unaffected proteins or peptides. In another preferred embodiment, the isolated nucleic acid molecule comprises an affected or unaffected peptide nucleotide sequence encoding one or more proteins according to the present invention.

Isolation of Nucleic Acid. In another aspect of the present invention, isolated nucleic acid molecules coding for peptides having amino acid sequences corresponding to affected or unaffected protein or peptide are provided.

The nucleic acid molecule can be isolated from a biological sample containing nucleic acid using known techniques, such as but not limited to, primer amplification or cDNA cloning.

The nucleic acid molecule can be isolated from a biological sample containing genomic DNA or from a genomic library. Suitable biological samples include, but are not limited to, normal or pathologic animal cells or tissues, such as pancreas, liver, lung, spleen, bone marrow, blood or blood components, central nervous system (CNS), glands, skin, hair, testes, ovary, kidney, thyroid, cerebrospinal fluid (CSF), peripheral nervous system (neurons, ganglion) and portions, cells of heart, smooth, skeletal or cardiac muscle, autonomic nervous system, and extracts or cell cultures thereof, provided in vivo, in situ or in vitro, as cultured, passaged, non-passaged, transformed, recombinant, or isolated cells and/or tissues. The method of obtaining the biological sample will vary depending upon the nature of the sample.

One skilled in the art will realize that a mammalian genome can be subject to slight allelic variations between individuals and if these variations lead to differences in protein sequence, they may be detected by proteome analysis (2D gel electrophoresis and/or mass spectrometry). Therefore, isolated nucleic acid molecules are also intended to include allelic variations, so long as the sequence encodes an affected or unaffected peptide. When an affected or unaffected peptide allele does not encode the identical amino acid sequence to that found in one or more proteins of the invention, or at least domain thereof, it can be isolated and identified as affected or unaffected protein or peptide using the same techniques used herein, and especially nucleic acid amplification techniques to amplify the appropriate gene with primers based on the sequences disclosed herein. Such variations are presented, e.g., in Tables 1 and 2.

The cloning of large cDNAs is the same but takes more routine experimentation, than smaller cDNAs. One useful method relies on cDNA bacteriophage library screening (see, e.g., Sambrook, infra, or Ausubel, infra). Probes for the screening are labeled, e.g., with random hexamers and Klenow enzyme (Pharmacia kit). If 5' cDNAs are not obtained with these approaches, a subcDNA library can be prepared in which a specific affected protein encoding primers are used to prime the reverse tanscript reaction in place of oligo dT or random primers. The CDNA sublibrary is then cloned into standard vectors such as lambda zap and screened using conventional techniques. The construction of a full-length CDNA is performed by subcloning overlapping fragments into an expression vector (either prokaryotic or eukaryotic). This task is more difficult with large cDNAs because of the paucity of unique restriction sites, but routine restriction, cloning or PCR is used to join the fragments.

Methods for Detecting the Presence of an Affected or Unaffected Peptide-Encoding Nucleic Acid in a Biological Sample. In another embodiment, the present invention relates to methods for detecting the presence of affected or unaffected protein or peptide encoding nucleic acid in a sample. Such methods can comprise (a) contacting the sample with the above-described nucleic acid probe, under conditions such that hybridization occurs, and (b) detecting the presence of a labeled probe bound to the nucleic acid probe. One skilled in the art can select a suitable, labeled nucleic acid probe according to techniques known in the art as described above. Samples to be tested include, but are not limited to, RNA samples of mammalian tissue.

Affected peptides or proteins are found expressed in any specific cell type associated with a particular pathology. Accordingly, affected or unaffected protein or peptide probes can be used detect the presence of RNA from cells in such a biological sample. Further, altered expression levels of affected or unaffected protein or peptide RNA in an individual, as compared to normal levels, can indicate the presence of disease. The affected or unaffected protein or peptide probes can further be used to assay cellular activity in general and specifically in the affected tissue. Fragments of the affected protein or the whole protein may be also detected in body fluids (including but not limited to blood, cerebrospinal fluid and urine).

DNA Constructs Encoding an Affected or Unaffected Peptide Nucleic Acid Molecules and Hosts Containing These Constructs. A nucleic acid sequence encoding an affected or unaffected peptide of the invention can be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, e.g., by Ausubel et al., infra, and are well known in the art.

The invention accordingly encompasses the expression of an affected or unaffected peptide, in either prokaryotic or eukaryotic cells, although eukaryotic expression is preferred.

Preferred hosts are bacterial or eukaryotic hosts including bacteria, yeast, insects, fungi, bird and mammalian cells either in vivo, or in situ, or host cells of mammalian, insect, bird or yeast origin. It is preferred that the mammalian cell or tissue is of human, primate, hamster, rabbit, rodent, cow, pig, sheep, horse, goat, dog or cat origin, but any other mammalian cell can be used.

Eukaryotic hosts can include yeast, insects, fungi, and mammalian cells either in vivo, in tissues, in biopsies or in tissue culture. Preferred eukaryotic hosts can also include, but are not limited to insect cells, mammalian cells either in vivo, or in tissue culture. Preferred mammalian cells include *Xenopus oocytes,* HeLa cells, cells of fibroblast origin such as VERO or CHO-K1, or cells of lymphoid origin and their derivatives.

Mammalian cells provide post-translational modifications to protein molecules including correct folding or glycosylation at correct sites. Mammalian cells which can be useful as hosts include cells of fibroblast origin such as, but not limited to, NIH 3T3, VERO or CHO, or cells of lymphoid origin, such as, but not limited to, the hybridoma SP2/O-Ag14 or the murine myeloma P3-X63Ag8, hamster cell lines (e.g., CHO-K1 and progenitors, e.g., CHO-DUXB11) and their derivatives. One preferred type of mammalian cells are cells which are intended to replace the function of the genetically deficient cells in vivo.

For a mammalian cell host, many possible vector systems are available for the expression of at least one affected or unaffected protein or peptide. A wide variety of transcriptional and translational regulatory sequences can be employed, depending upon the nature of the host. The transcriptional and translational regulatory signals can be derived from viral sources, such as, but not limited to, adenovirus, bovine papilloma virus, Simian virus, or the like, where the regulatory signals are associated with a particular gene which has a high level of expression. Alternatively, promoters from mammalian expression products, such as, but not limited to, actin, collagen, myosin, protein production. See, Ausubel, infra; Sambrook, infra.

When live insects are to be used, silk moth caterpillars and baculoviral vectors are presently preferred hosts for large scale affected or unaffected protein or peptide production according to the invention. Production of affected or unaffected proteins or peptides in insects can be achieved, for example, by infecting the insect host with a baculovirus engineered to express at least one affected or unaffected protein or peptide by methods known to those skilled in the related arts. See Ausubel et al, eds. *Current Protocols in Molecular Biology*, Wiley Interscience, §§16.8–16.11 (1987–1996).

In a preferred embodiment, the introduced nucleotide sequence will be incorporated into a plasmid or viral vector capable of autonomous replication in the recipient host. Any of a wide variety of vectors can be employed for this purpose. See, e.g., Ausubel et al., infra, §§1.5, 1.10, 7.1, 7.3, 8.1, 9.6, 9.7, 13.4, 16.2, 16.6, and 16.8–16.11. Factors of importance in selecting a particular plasmid or viral vector include: the ease with which recipient cells that contain the vector can be recognized and selected from those recipient cells which do not contain the vector; the number of copies of the vector which are desired in a particular host; and whether it is desirable to be able to "shuttle" the vector between host cells of different species.

Different host cells have characteristic and specific mechanisms for the translational and post-translational processing and modification (e.g., glycosylation, cleavage) of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of the heterologous affected or unaffected protein or peptide protein. Furthermore, different vector/host expression systems can effect processing reactions such as proteolytic cleavages to different extents.

As discussed above, expression of affected or unaffected protein or peptide in eukaryotic hosts requires the use of eukaryotic regulatory regions. Such regions will, in general, include a promoter region sufficient to direct the initiation of RNA synthesis. See, e.g., Ausubel, infra; Sambrook, infra.

Isolation of an Affected or Unaffected Peptide. The affected or unaffected protein or peptide proteins or fragments of this invention can be obtained by expression from recombinant DNA as described above. Alternatively, an affected or unaffected peptide can be purified from biological material. If so desired, the expressed at least one affected or unaffected protein or peptide can be isolated and purified in accordance with conventional method step s, such as extraction, precipitation, chromatography, affinity chromatography, electrophoresis, or the like. For example, cells expressing at least one affected or unaffected protein or peptide in suitable levels can be collected by centrifugation, or with suitable buffers, lysed, and the protein isolated by column chromatography, for example, on DEAE-cellulose, phosphocellulose, polyribocytidylic acid-agarose, hydroxyapatite or by electrophoresis or immunoprecipitation. Alternatively, affected or unaffected proteins or peptides can be isolated by the use of specific antibodies, such as, but not limited to, an affected or unaffected peptide or affected or unaffected protein or peptide antibody. Such antibodies can be obtained by known method steps (see, e.g. Colligan, infra; Ausubel, infra.

However, other methods, known to those of skill in the art can be used to effectively separate molecules based on size. A fourth step in a purification protocol for an affected or unaffected peptide can include analyzing the immunoreactive peaks by sodium dodecyl sulfate-polyacrylamide gel electrophoresis (SDS-PAGE), a further gel chromatographic purification step , and staining, such as, for example, silver staining. A fifth step in a purification method can include subjecting the affected or unaffected protein or peptide obtained after SDS-PAGE to affinity chromatography, or any other procedure based upon affinity between a substance to be isolated and a molecule to which it can specifically bind. For further purification of an affected or unaffected peptide, affinity chromatography on SEPHAROSE conjugated to anti-affected peptide mAbs (specific mABs generated against substantially pure affected or unaffected protein or peptide) can be used. Alternative methods, such as reverse-phase HPLC, or any other method characterized by rapid separation with good peak resolution are useful.

It will be appreciated that other purification step s can be substituted for the preferred method described above. Those of skill in the art will be able to devise alternate purification schemes without undue experimentation.

An Antibody Having Binding Affinity to an Affected or Unaffected Peptide and a Hybridoma Containing the Antibody. In another embodiment, the invention relates to an antibody having binding affinity specifically to an affected or unaffected peptide as described above or fragment thereof. Those which bind selectively to affected or unaffected protein or peptide would be chosen for use in methods which could include, but should not be limited to, the analysis of altered-affected or unaffected protein or peptide expression in tissue containing affected or unaffected protein or peptide.

The affected or unaffected protein or peptide of the invention can be used in a variety of procedures and methods, such as for the generation of antibodies, for use in identifying pharmaceutical compositions, and for studying DNA/protein interaction.

The affected or unaffected protein or peptide of the invention can be used to produce antibodies or hybridomas. One skilled in the art will recognize that if an antibody is desired, such a peptide would be generated as described herein and used as an immunogen.

The antibodies of the invention include monoclonal and polyclonal antibodies, as well as fragments of these antibodies. The invention further includes single chain antibodies. Antibody fragments which contain the idiotype of the molecule can be generated by known techniques.

The term "antibody" is meant to include polyclonal antibodies, monoclonal antibodies (mAbs), chimeric antibodies, anti-idiotypic (anti-Id) antibodies to antibodies that can be labeled in soluble or bound form, as well as fragments thereof provided by any known technique, such as, but not limited to enzymatic cleavage, peptide synthesis or recombinant techniques. Polyclonal antibodies are heterogeneous populations of antibody molecules derived from the sera of animals immunized with an antigen. A monoclonal antibody contains a substantially homogeneous population of antibodies specific to antigens, which population contains substantially similar epitope binding sites. MAbs can be obtained by methods known to those skilled in the art. See, e.g., Kohler and Milstein, Nature 256:495–497 (1975); U.S. Pat. No. 4,376,110; Ausubel et al, eds., CURRENT PROTOCOLS IN MOLECULAR BIOLOGY, Greene Publishing Assoc. and Wiley Interscience, N.Y., (1987–1996); and Harlow and Lane ANTIBODIES: A LABORATORY MANUAL Cold Spring Harbor Laboratory (1988); Colligan et al., eds., Current Protocols in Immunology, Greene Publishing Assoc. and Wiley Interscience, N.Y., (1992–1996), the contents of which references are incorporated entirely herein by reference. Such antibodies can be of any inmnunoglobulin class including IgG, IgM, IgE, IgA, GILD and any subclass thereof. A hybridoma producing a mAb of the invention can be cultivated in vitro, in situ or in vivo. Production of high titers of mAbs in vivo or in situ makes this the presently preferred method of production.

Chimeric antibodies are molecules different portions of which are derived from different animal species, such as those having variable region derived from a murine mAb and a human immunoglobulin constant region, which are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (Cabilly et al, Proc. Natl. Acad. Sci. USA 81:3273–3277 (1984); Morrison et al., Proc. Natl. Acad. Sci. USA 81:6851–6855 (1984); Boulianne et al., Nature 312:643–646 (1984); Cabilly et al., European Patent Application 125023; Neuberger et al., Nature 314:268–270 (1985); Taniguchi et al., European Patent Application 171 496; Morrison et al., European Patent Application 173 494; Neuberger et al., PCT Application WO 86/01533; Kudo et al., European Patent Application 184 187; Morrison et al., European Patent Application 173 494; Sahagan et al., J. Immunol. 137:1066–1074 (1986); Robinson et al., International Patent Publication No. PCT/US86/02269; Liu et al., Proc. Natl. Acad. Sci. USA 84:3439–3443 (1987); Sun et al., Proc. Natl. Acad. Sci. USA 84:214–218 (1987); Better et al., Science 240:1041–1043 (1988); and Harlow, infra. These references are entirely incorporated herein by reference.

An anti-idiotypic (anti-Id) antibody is an antibody which recognizes unique determinants generally associated with the antigen-binding site of an antibody. An Id antibody can be prepared by immunizing an animal of the same species and genetic type (e.g., mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference.

The anti-Id antibody can also be used as an "immunogen" to induce an immune response in yet another animal, producing a so-called anti-anti-Id antibody. The anti-anti-Id can be epitopically identical to the original mAb which induced the anti-Id. Thus, by using antibodies to the idiotypic determinants of a mAb, it is possible to identify other clones expressing antibodies of identical specificity.

Accordingly, mAbs generated against an affected or unaffected peptide of the invention can be used to induce anti-Id antibodies in suitable animals, such as BALB/c mice. Spleen cells from such immunized mice are used to produce anti-Id hybridomas secreting anti-Id mAbs. Further, the anti-Id mAbs can be coupled to a carrier such as keyhole limpet hemocyanin (KLH) and used to immunize additional BALB/c mice. Sera from these mice will contain anti-anti-Id antibodies that have the binding properties of the original mAb specific for an affected or unaffected peptide specific epitope. The anti-Id mAbs thus have their own idiotypic epitopes, or "idiotopes" structurally similar to the epitope being evaluated.

The term "antibody" is also meant to include both intact molecules as well as fragments thereof, such as, for example, Fab and F(ab')2, which are capable of binding antigen. Fab and F(ab')2 fragments lack the Fc fragment of intact antibody, clear more rapidly from the circulation, and can have less non-specific tissue binding than an intact antibody (Wahl et al., J. Nucl. Med. 24:316–325 (1983)). It will be appreciated that Fab and F(ab')2 and other fragments of the antibodies useful in the invention can be used for the detection and/or quantitation of an affected or unaffected peptide according to the methods disclosed herein for intact antibody molecules. Such fragments are typically produced by proteolytic cleavage, using enzymes such as papain (to produce Fab fragments) or pepsin (to produce F(ab')2 fragments). An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen can have one, or more than one epitope. The specific reaction referred to above is meant to indicate that the antigen will react, in a highly selective manner, with its corresponding antibody and not with the multitude of other antibodies which can be evoked by other antigens.

Immunoassays. Antibodies of the invention, directed against an affected or unaffected peptide, can be used to detect or diagnose an affected or unaffected peptide or an affected or unaffected peptide- related pathologies. Screening methods are provided by the invention can include, e.g., immunoassays employing radioimmunoassay (RIA) or enzyme-linked immunosorbant assay (ELISA) methodologies, based on the production of specific antibodies (monoclonal or polyclonal) to an affected or unaffected peptide. For these assays, biological samples are obtained by biopsy, or other tissue sampling. For example, in one form of RIA, the substance under test is mixed with diluted antiserum in the presence of radiolabeled antigen. In this method, the concentration of the test substance will be inversely proportional to the amount of labeled antigen bound to the specific antibody and directly related to the amount of free labeled antigen. Other suitable screening methods will be readily apparent to those of skill in the art.

Furthermore, one skilled in the art can readily adapt currently available procedures, as well as the techniques, methods and kits disclosed above with regard to antibodies, to generate peptides capable of binding to a specific peptide sequence in order to generate rationally designed antipeptide peptides, for example see Hurby et al., "Application of Synthetic Peptides: Antisense Peptides", In: Synthetic Peptides, A User's Guide, W. H. Freeman, NY, pp. 289–307 (1992), and Kaspczak et al., Biochemistry 28:9230–8 (1989).

One embodiment for carrying out the diagnostic assay of the invention on a biological sample containing an affected or unaffected peptide, comprises:

(a) contacting a detectably labeled affected or unaffected protein or peptide-specific antibody with a solid support to effect immobilization of said affected or unaffected protein or peptide-specific antibody or a fragment thereof;

(b) contacting a sample suspected of containing an affected or unaffected peptide with said solid support;

(c) incubating said detectably labeled affected or unaffected protein or peptide-specific antibody with said support for a time sufficient to allow the immobilized affected or unaffected protein or peptide-specific antibody to bind to the affected or unaffected protein or peptide;

(d) separating the solid phase support from the incubation mixture obtained in step (c); and (e) detecting the bound label and thereby detecting and quantifying affected or unaffected protein or peptide.

The specific concentrations of detectably labeled antibody and affected or unaffected protein or peptide, the temperature and time of incubation, as well as other assay conditions can be varied, depending on various factors including the concentration of an affected or unaffected peptide in the sample, the nature of the sample, and the like. The binding activity of a given lot of anti-affected peptide antibody can be determined according to well known methods. Those skilled in the art will be able to determine operative and optimal assay conditions for each determination by employing routine experimentation. Other such step s as washing, stirring, shaking, filtering and the like can be added to the assays as is customary or necessary for the particular situation.

Detection can be accomplished using any of a variety of assays. For example, by radioactively labeling the affected or unaffected protein or peptide-specific antibodies or antibody fragments, it is possible to detect affected or unaffected protein or peptide through the use of radioimmune assays. A good description of a radioimmune assay can be found in Colligan, infra, and Ausubel, infra, entirely incorporated by reference herein. Preferably, the detection of cells which express an affected or unaffected peptide can be accomplished by in vivo imaging techniques, in which the labeled antibodies (or fragments thereof) are provided to a subject, and the presence of the affected or unaffected protein or peptide is detected without the prior removal of any tissue sample. Such in vivo detection procedures have the advantage of being less invasive than other detection methods, and are, moreover, capable of detecting the presence of affected or unaffected protein or peptide in tissue which cannot be easily removed from the patient, such as brain tissue.

There are many different in vivo labels and methods of labeling known to those of ordinary skill in the art. Examples of the types of labels which can be used in the invention include radioactive isotopes and paramagnetic isotopes. Those of ordinary skill in the art will know of other suitable labels for binding to the antibodies used in the invention, or will be able to ascertain such, using routine experimentation. Furthermore, the binding of these labels to the antibodies can be done using standard techniques common to those of ordinary skill in the art.

For diagnostic in vivo imaging, the type of detection instrument available is a major factor in selecting a given radionuclide. The radionucleotide chosen must have a type of decay which is detectable for a given type of instrument. In general, any conventional method for visualizing diagnostic imaging can be utilized in accordance with this invention. For example, positron emission tomography (PET), gamma, beta, and magnetic resonance imaging (MRI) detectors can be used to visualize diagnostic imagining.

The antibodies useful in the invention can also be labeled with paramagnetic isotopes for purposes of in vivo diagnosis. Elements which are particularly useful, as in Magnetic Resonance Imaging (MRI), include 157Gd, 55Mn, 162Dy, and 56Fe. The antibodies (or fragments thereof) useful in the invention are also particularly suited for use in in vitro immunoassays to detect the presence of an affected or unaffected peptide in body tissue, fluids (such as CSF), or cellular extracts. In such immunoassays, the antibodies (or antibody fragments) can be utilized in liquid phase or, preferably, bound to a solid-phase carrier, as described above.

In situ detection can be accomplished by removing a histological specimen from a patient, and providing the combination of labeled antibodies of the invention to such a specimen. The antibody (or fragment) is preferably provided by applying or by overlaying the labeled antibody (or fragment) to a biological sample. Through the use of such a procedure, it is possible to determine not only the presence of an affected or unaffected peptide, but also the distribution of an affected or unaffected peptide on the examined tissue. Using the invention, those of ordinary skill will readily perceive that any of a wide variety of histological methods (such as staining procedures) can be modified in order to achieve such in situ detection. As used herein, an effective amount of a diagnostic reagent (such as an antibody or antibody fragment) is one capable of achieving the desired diagnostic discrimination and will vary depending on such factors as age, condition, sex, the extent of disease of the subject, counter-indications, if any, and other variables to be adjusted by the physician. The amount of such materials which are typically used in a diagnostic test are generally between 0.01 to 5 mg, and preferably between 0.1 to 0.5 mg. The assay of the invention is also ideally suited for the preparation of a kit. Such a kit can comprise a carrier means being compartmentalized to receive in close confinement therewith one or more container means such as vials, tubes and the like, each of said container means comprising the separate elements of the immunoassay.

For example, there can be a container means containing a first antibody immobilized on a solid phase support, and a further container means containing a second detectably labeled antibody in solution. Further container means can contain standard solutions comprising serial dilutions of the affected or unaffected protein or peptide to be detected. The standard solutions of an affected or unaffected peptide can be used to prepare a standard curve with the concentration of affected or unaffected protein or peptide plotted on the abscissa and the detection signal on the ordinate. The results obtained from a sample containing an affected or unaffected peptide can be interpolated from such a plot to give the concentration of the affected or unaffected protein or peptide.

The assay of the invention is also ideally suited for the preparation of a kit. Such a kit can comprise a carrier means being compartmentalized to receive in close confinement therewith one or more container means such as vials, tubes and the like, each of said container means comprising the separate elements of the immunoassay.

For example, there can be a container means containing a first antibody immobilized on a solid phase support, and a further container means containing a second detectably labeled antibody in solution. Further container means can contain standard solutions comprising serial dilutions of the affected or unaffected protein or peptide to be detected. The standard solutions of an affected or unaffected peptide can be used to prepare a standard curve with the concentration of affected or unaffected protein or peptide plotted on the abscissa and the detection signal on the ordinate. The results obtained from a sample containing an affected or unaffected peptide can be interpolated from such a plot to give the concentration of the affected or unaffected protein or peptide.

Diagnostic Screening. It is to be understood that although the following discussion is specifically directed to human patients, the teachings are also applicable to any animal that expresses at least one affected or unaffected peptide. The diagnostic and screening methods of the invention are especially useful for a patient suspected of being at risk for developing a disease associated with an altered expression level of affected or unaffected protein or peptide based on family history, or a patient in which it is desired to diagnose an affected or unaffected peptide-related disease.

According to the invention, presymptomatic screening of an individual in need of such screening is now possible using DNA encoding the affected or unaffected protein or peptide protein of the invention. The screening method of the invention allows a presymptomatic diagnosis, including prenatal diagnosis, of the presence of a missing or aberrant affected or unaffected peptide gene in individuals, and thus an opinion concerning the likelihood that such individual would develop or has developed an affected or unaffected peptide-associated disease. This is especially valuable for the identification of carriers of altered or missing affected or unaffected peptide genes, for example, from individuals with a family history of an affected or unaffected peptide-related pathology. Early diagnosis is also desired to maximize appropriate timely intervention.

In one preferred embodiment of the method of screening, a tissue sample would be taken from such individual, and screened for (1) the presence of the "normal" affected or unaffected protein or peptide gene; (2) the presence of affected or unaffected protein or peptide mRNA and/or (3) the presence of affected or unaffected protein or peptide protein. The normal human gene can be characterized based upon, for example, detection of restriction digestion patterns in "normal" versus the patient's DNA, including RFLP analysis, using DNA probes prepared against the affected or unaffected protein or peptide sequence (or a functional fragment thereof) taught in the invention. Similarly, affected or unaffected protein or peptide mRNA can be characterized and compared to normal affected or unaffected protein or peptide mRNA (a) levels and/or (b) size as found in a human population not at risk of developing affected or unaffected protein or peptide-associated disease using similar probes. Lastly, affected or unaffected protein or peptide protein can be (a) detected and/or (b) quantitated using a biological assay for affected or unaffected protein or peptide activity or using an immunological assay and affected or unaffected protein or peptide antibodies. When assaying affected or unaffected protein or peptide protein, the immunological assay is preferred for its speed. An (1) aberrant affected or unaffected protein or peptide DNA size pattern, and/or (2) aberrant affected or unaffected protein or peptide MnRNA sizes or levels and/or (3) aberrant affected or unaffected protein or peptide protein levels would indicate that the patient is at risk for developing an affected or unaffected peptide-associated disease.

The screening and diagnostic methods of the invention do not require that the entire affected or unaffected protein or peptide DNA coding sequence be used for the probe. Rather, it is only necessary to use a fragment or length of nucleic acid that is sufficient to detect the presence of the affected or unaffected protein or peptide gene in a DNA preparation from a normal or affected individual, the absence of such gene, or an altered physical property of such gene (such as a change in electrophoretic migration pattern).

Prenatal diagnosis can be performed when desired, using any known method to obtain fetal cells, including amniocentesis, chorionic villous sampling (CVS), and fetoscopy. Prenatal chromosome analysis can be used to determine if the portion of the chromosome possessing the normal affected or unaffected protein or peptide gene is present in a heterozygous state.

Drug Screening Using Identified Proteins and Relation to Diagnostic and/or Therapeutic Agents. A diagnostic or therapeutic affected or unaffected protein or peptide modulating agent or ligand of the present invention can be, but is not limited to, at least one selected from a nucleic acid, a compound, a protein, an element, a lipid, an antibody, a saccharide, an isotope, a carbohydrate, an imaging agent, a lipoprotein, a glycoprotein, an enzyme, a detectable probe, and antibody or fragment thereof, or any combination thereof, which can be detectably labeled as for labeling antibodies, as described herein. Such labels include, but are not limited to, enzymatic labels, radioisotope or radioactive compounds or elements, fluorescent compounds or metals, chemiluminescent compounds and bioluminescent compounds. Alternatively, any other known diagnostic or therapeutic agent can be used in a method of the invention.

A therapeutic agent used in the invention can have a therapeutic effect on the target cell as a specific cell type, groups of cells (which are not necessarily adjacent) or circulating protein complexes, the effect selected from, but not limited to: correcting a defective gene or protein, a drug action, a toxic effect, a growth stimulating effect, a growth inhibiting effect, a metabolic effect, a catabolic affect, an anabolic effect, a neurohumoral effect, a cell differentiation stimulatory effect, a cell differentiation inhibitory effect, a neuromodulatory effect, a pluripotent stem cell stimulating effect, and any other known therapeutic effects that modulates at least one affected or unaffected protein or peptide in a cell of a specific cell type can be provided by a therapeutic agent delivered to a target cell via pharmaceutical administration or via a delivery vector according to the invention.

A therapeutic nucleic acid as a therapeutic agent can have, but is not limited to, at least one of the following therapeutic effects on a target cell: inhibiting transcription of a DNA sequence; inhibiting translation of an RNA sequence; inhibiting reverse transcription of an RNA or DNA sequence; inhibiting a post-translational modification of a protein; inducing transcription of a DNA sequence; inducing translation of an RNA sequence; inducing reverse transcription of an RNA or DNA sequence; inducing a post-translational modification of a protein; transcription of the nucleic acid as an RNA; translation of the nucleic acid as a protein or enzyme; and incorporating the nucleic acid into a chromosome of a target cell for constitutive or transient expression of the therapeutic nucleic acid.

Therapeutic effects of therapeutic nucleic acids can include, but are not limited to: turning off a defective gene or processing the expression thereof, such as antisense RNA or DNA; inhibiting viral replication or synthesis; gene therapy as expressing a heterologous nucleic acid encoding a therapeutic protein or correcting a defective protein; modifying a defective or underexpression of an RNA such as an hnRNA, an mRNA, a tRNA, or an rRNA; encoding a drug or prodrug, or an enzyme that generates a compound as a drug or prodrug in pathological or normal cells expressing the affected protein or peptide; and any other known therapeutic effects.

A therapeutic nucleic acid of the invention which encodes, or provides the therapeutic effect any known toxin, prodrug or gene drug for delivery to pathogenic cells can also include genes under the control of a tissue specific transcriptional regulatory sequence (TRSs) specific for pathogenic affected or unaffected protein or peptide containing cells. Such TRSs would further limit the expression of the therapeutic agent in the target cell, according to known methods.

Non-limiting examples of such affected or unaffected protein or peptide modulating agents or ligands of the present invention and methods thereof include antibodies or anti-diotype antibodies to the affected or unaffected proteins or peptides, sense or antisense nucleic acids, and the like.

Affected peptide antagonists can be used to treat a pathology involving a specific cell type or organ, or pathologies related to the abnormally high levels of expression of at least one naturally occurring affected or unaffected peptide, where an affected or unaffected peptide antagonist also inhibits at least one affected or unaffected peptide, or where the pathology is mediated to some extent by an affected or unaffected peptide. Such pathologies, include, but are not limited to; inflammatory diseases, neurodegenerative diseases, and immune system related diseases, as well as other diseases as known in the art or as described herein.

Inflammatory diseases can include, but are not limited to, chronic inflammatory pathologies and vascular inflammatory pathologies. Chronic inflammatory pathologies include, but are not limited to sarcoidosis, chronic inflammatory bowel disease, ulcerative colitis, and Crohn's pathology and vascular inflammatory pathologies, such as, but not limited to, disseminated intravascular coagulation, atherosclerosis, and Kawasaki's pathology.

Neurodegenerative diseases can include, but are not limited to, demyelinating diseases, such as multiple sclerosis and acute transverse myelitis; hyperkinetic movement disorders, such as Huntington's Chorea and senile chorea; hypokinetic movement disorders, such as Parkinson's disease; progressive supranucleo palsy; spinocerebellar degenerations, such as spinal ataxia, Friedreich's ataxia; multiple systems degenerations (Mencel, Dejerine-Thomas, Shi-Drager, and Machado-Joseph); and systemic disorders (Refsum's disease, abetalipoprotemia, ataxia, telangiectasia, and mitochondrial multi-system disorder); demyelinating core disorders, such as multiple sclerosis, acute transverse myelitis; disorders of the motor unit, such as neurogenic muscular atrophies (anterior horn cell degeneration, such as amyotrophic lateral sclerosis, infantile spinal muscular atrophy and juvenile spinal muscular atrophy); or any subset thereof.

Affected protein or peptide agonists or antagonists can be used to treat pathologies related to the abnormally low or high levels of expression of at least one affected peptide, where the affected peptide agonist or antagonist also enhances or inhibits, respectively, at least one affected peptide. Such pathologies, include, but are not limited to, neurodegenerative diseases, diseases of the gastrointestinal tract due to dysfunction of the enteric nervous system (e.g., colitis, ileitis, inflammatory bowel syndrome); diseases of the cardiovascular system (e.g., hypertension and congestive heart failure); diseases of the genitourinary tract involving sympathetic and parasympathetic innervation (e.g., benign prostrate hyperplasia, impotence); diseases of the neuromuscular system (e.g., muscular dystrophy, multiple sclerosis, epilepsy), and diseases of the endocrine system (e.g. diabetes).

Having now generally described the invention, the same will be more readily understood through reference to the following Examples which are provided by way of illustration, and are not intended to be limiting of the invention, unless specified.

EXAMPLES

Example 1

Gel Image Analysis

Example 1A

By way of example, it can be desired to identify why three different animals, such as three individual rats, had three different blood pressures. A 2-DGE gel image for artery cells from the three different animals are compared. The gels are compared to look for proteins that varied in their expression, and that could be statistically correlated with blood pressure in the animal. The type of statistical analysis would be a linear regression. The linear regression of the expression of every spot compared to the blood pressure of the animal would be carried out.

Example 1B

As another example, one group of gel images can relate to normal or untreated cells, such as islets. A second group of gel images can relate to treated cells, such as cells treated with interleukin (IL)-1β. The statistical average of each spot in each set of gel images is computed. The statistical average of each spot in the first set of gel images is compared to the statistical average of each spot in the second set of gel images to determine if they are statistically different. In this manner, the operator is able to quickly and easily determine what proteins are changed (either up- or downregulated) by the IL-1β treatment.

Example 1C

As yet another example, one group of images can relate to normal rats and another group of images to diabetic rats. The objective is to find the difference between the two groups. The gel images are divided into two sets: a first set of gel images for the normal rats; and a second set of gel images for the diabetic rats. The analysis is carried out in a similar fashion to that described above for treated and untreated islets to determine differences in protein expression between normal and diabetic rats.

Example 2

Interleukin-1DF Induced Changes in the Protein Expression of Rat Islets: A Computerized Database Summary Two-dimensional (2-D) gel electrophoresis of pancreatic islet proteins can be an important tool facilitating studies of the molecular pathogenesis of insulin-dependent diabetes mellitus. Insulin-dependent diabetes mellitus is caused by an autoimmune destruction of the β-cells in the islets of Langerhans. The cytokine interleukin 1β inhibits insulin release and is selectively cytotoxic to β-cells in isolated pancreatic rat islets. The antigen(s) triggering the inmmune response as well as the intracellular mechanisms of action of interleukin 1β-mediated β-cell cytotoxicity are unknown. However, previous studies have found an association with alterations in protein synthesis. Thus, 2-D gel electrophoresis of islet proteins can lead to 1) the identification of primary antigen(s) initiating the immune destruction of the β-cells 2) the determination of qualitative and quantitative changes in specific islet proteins induced by cytokines and 3) the determination of the effects of agents modulating cytokine action. Therefore, the aim of this study was to create databases of all reproducibly detectable protein spots on 10% and 15% acrylamide 2-D gels of neonatal rat islets (10% & 15% DB), labelled under standardized culture conditions. 1792 spots were present in 5 of 5 gels in the 15% DB, whereas 1373 spots were present in 5 of 5 gels in the 10% DB, yielding a qualitative reproducibility between 75.2% and 91.7%. In both DBs, the average coefficient of variation of the percentage of integrated optical density (CV% of %IOD) for spots present in all gel was between 42.4% and 45.7%. When the same sample was analyzed in consecutive sets of gels on different days (interassay analysis), the average CV% of %IOD was 35.5%–36.1%. When the same sample was analyzed repeatedly in one set of gels (intraassay analysis), the average CV% of %IOD was 30.2% in the IEF gels, while the average CV% of %IOD was unchanged (45.7%) in the NEPHGE gels. Applying the 10% DB to distinguish proteins altered in expression by IL-1β, 105 currently unidentified protein spots were found to be up-/down-regulated or synthesized de novo by IL-1β. In conclusion, we present the first 10% and 15% acrylamide 2-D gel protein databases of neonatal rat islets of Langerhans and demonstrate its usage to identify proteins altered in expression by IL-1β.

Introduction

The cytokine interleukin 1β inhibits insulin release and is selectively cytotoxic to β-cells in isolated pancreatic rat islets (Mandrup-Poulsen, T, *Diabetologia*, in press (1996)). Active protein synthesis is a crucial part of β-cell destruction, defense and repair after insults such as cytokines. The free radical nitric oxide (NO) has been demonstrated to be an important mediator of the deleterious effects of cytokines on islet α-cells (Southern, et al., *FEBS. Lett.* 276:42–44 (1990); Welsh, et al., *Endocrinol.* 129:3167–3173 (1991); Corbett, et al., *J. Biol. Chem.* 266:21351–21354 (1991)). Thus, analogues of L-arginine, the substrate for NO production, prevent the deleterious effects of interleukin 1β (IL-1β) (Southern, et al., *FEBS. Lett.* 276:42–44 (1990); Welsh, et al., *Endocrinol.* 129:3167–3173 (1991); Corbett, et al., *J. Biol. Chem.* 266:21351–21354 (1991)) and nMRNA for the cytokine-inducible isoform of NO synthase (iNOS) is induced by IL-1β in β-, but not α-cells (Corbett, et al., *J. Clin. Invest.* 90:2384–2391 (1992)). We have recently cloned iNOS from neonatal rat islets and have demonstrated the expression of the recombinant iNOS as a series of spots on two-dimensional (2-D) gels, most likely as phosphorylated isoforms, with the expected molecular mass of 131 kDa and pI values in the range of 6.8 to 7.0 (Karlsen, et al., *Diabetes* 44:753–758 (1995)).

Further, inhibitors of protein synthesis block the inhibitory effect of IL-1β on islet function (Hughes, et al., *J. Clin. Invest.* 86:856–863 (1990)), indicating that de novo protein synthesis is necessary for the deleterious effect of IL-1β.

IL-1β also induces the synthesis of the heat shock proteins (HSP) HSP32 (heme oxygenase) and HSP70 (Helqvist, et al., *Acta Endocrinol. (Copenh.)* 121:136–140(1989); Helqvist, et al., *Diabetologia* 34:150–156 (1991); Welsh, et al., *Autoimmunity* 9:33–40 (1991)), known to play a role in protection against cellular stress and in cell repair (Kaufmann, *Immunol. Today* 11:129–136 (1990)). Further, IL-1β inhibits the synthesis of a number of unknown proteins with molecular weights of 45, 50 (Hughes, et al., *J. Clin. Invest.* 86:856–863 (1990)), 75, 85, 95 and 120 kDa (Welsh, et al., *Autoimmunity* 9:33–40 (1991)) in islets. Using 2-D gel electrophoresis, we recently demonstrated that IL-1β up- and downregulated 29 and 3 proteins, respectively, in neonatal rat islets.

Endocrine islet cells can play an important role in β-cell destruction and, possibly, survival. Dispersion and sorting of islet cells is a potentially harmful procedure that could influence the protein synthesis pattern. The disadvantage of the chosen islet cell material is that any change in protein expression in one cell type will appear smaller because it is diluted by synthesis from other cells.

Thus, the aims of this study were to determine the spot detection reproducibility and to calculate the coefficient of variation of the percentage of integrated optical density (CV% of %IOD) for all ($^{35}$S)-methionine-labelled islet protein database spots. Additionally, we wanted to investigate the contribution of the intra- and interassay variation of the gel preparation to the total CV% of %IOD of the spots. Finally, we wanted to define the number of IL-1β-induced changes in the islet protein pattern by computer analysis.

Materials and Methods

Reagents. DMEM, RPMI 1640 and Hanks' balanced salt solution (HBSS) were purchased from Gibco, Paisley, Scotland. RPMI 1640 was supplemented with 20 mM HEPES buffer, 100,000 IU/l penicillin and 100 mg/L streptomycin. Authentic recombinant human IL-1β was provided by Novo Nordisk Ltd. (Bagsvaerd, Denmark). The specific activity was 400 U/ng (Moelvig, et al., *Scand. J. Immunol.* 31:225–235 (1990). The following other reagents were used: 2-mercaptoethanol, bovine serum albumin (BSA), Tris HCl, Tris base, glycine, (Sigma, St. Louis, USA); trichloracetic acid (TCA), phosphoric acid, NaOH, glycerol, n-butanol, bromophenol blue (Merck, Darmstadt, Germany); ($^{35}$S)-methionine (SJ 204, specific activity: >1.000 Ci/mmol, containing 0.1% 2-mercaptoethanol), Amplify® (Amersham International, Amersham, UK); filters (HAWP 0.25 μm pore size) (Millipore, Boston, USA); RNA'se A, DNA'se I (Worthington, Freehold, N.J., USA); urea (ultra pure) (Schwarz/Mann, Cambridge, Mass., USA); acrylamide, bisacrylamide, TEMED, ammonium persulphate (BioRad, Richmond, Calif., USA); ampholytes: pH 5–7, pH 3.5–10, pH 7–9, pH 8–9.5 (Pharmacia, Uppsala, Sweden); Nonidet P40 (BDH, Poole, UK); ampholytes: pH 5–7 and sodium dodecyl sulphate (Serva, Heidelberg, Germany); agarose (Litex, Copenhagen, Denmark); ethanol (absolute 96%) (Danish Distillers, Aalborg, Denmark); methanol (Prolabo, Brione Le Blanc, France); acetic acid (technical quality, 99% glacial) (Bie & Bemtsen, Arhus, Denmark) and X-ray film (Curix RP-2) (AGFA).

Islet isolation and culture. For the database and assay variation experiments, 12 different islet isolations were performed, 10 for the databases, 1 for intraassay and 1 for interassay analysis. For the studies involving IL-1β, 3 additional islet isolations were performed.

Islets from pancreata of 4 day old inbred Wistar Furth rats (Mollegard, Lille Skensved, Denmark) were isolated after collagenase digestion (Brunstedt, In: Lamer, J., Polh, S. L.

(Eds.), *Methods In Diabetes Research, Vol. 1 (Laboratory methods, Part C)*. Wiley & Sons, New York, pp. 254–288 (1984)). After a preculture period of 4 days in RPMI 1640+10% fetal calf serum, 150 islets were incubated for 24 h in 300 µl RPMI 1640+0.5% normal human serum (NHS). In a separate series of experiments, 150 islets were incubated for 24 h in 300 µl RPMI 1640+0.5% NHS with or without the addition of 150 pg/ml IL-1β.

Islet labelling. After 24 h in culture, the 150 islets were harvested, washed twice in HBSS and labelled for 4 h in 200 µl methionine-free Dulbecco's modified Eagle's medium (DMEM) with 10% NHS dialysed for amino acids, and 200 µCi ($^{35}$S)-methionine. To eliminate 2-mercaptoethanol ($^{35}$S)-methionine was freeze-dried for at least 4 h before labelling. After labelling, islets were washed thrice in HBSS, pelleted and frozen at -80° C.

Sample preparation. The frozen islets were resuspended in 100 µl DNAse I/RNAse A solution and lysed by freeze-thawing twice. After the second thawing they were left on ice for 30 min for the digestion of nucleic acids. The lysed sample was then freeze dried overnight. The samples were dissolved by shaking in 120 µl lysis buffer (8.5 M urea, 2% Nonidet P-40, 5% 2-mercaptoethanol and 2% ampholytes pH range 7–9) for a minimum of 4 h.

Determination of ($^{35}$S)-methionine incorporation. The amount of ($^{35}$S)-methionine incorporation was quantitated in duplicate by adding 10 µg BSA (0.2 µg/ml $H_2O$) as a carrier to 5 µl of a 1:10 dilution of each sample, followed by 0.5 ml of 10% TCA. This was left to precipitate for 30 min at 40° C. before being filtered through 0.25 µm filters. The HAWP filters were dried and placed into scintillation liquid for counting.

2-D gel electrophoresis. The procedure was essentially as described by O'Farrell et al., *Cell* 12:1133–1142 (1977) and Fey, S. J. et al., *The protein variation in basal cells and certain basal cell related benign and malignant diseases*, Faculty of Natural Science, University of Aarhus, Denmark (1984). Briefly, first dimension gels contained 4% acrylamide, 0.25% bisacrylamide and ampholytes (the actual ratio depending upon the batch) and were 175 mm long and 1.55 mm in diameter. Equal numbers of counts ($10^6$ cpm) of each sample were applied to the gels. In case of lower amounts of radioactivity it was necessary to regulate the exposure time of the gel so that comparable total optical densities were obtained. The samples were analyzed on both isoelectric focusing (IEF; pH 3.5–7) and non-equilibrium pH-gradient electrophoresis (NEPHGE; pH 6.5–10.5) gels. IEF gels were prefocused for approximately 4 h at 140 µA/gel (limiting current), the sample was then applied and focused for 18 h at 1200 V (limiting voltage). NEPHGE gels were focused for approximately 6.5 h using 140 µA/gel and 1200 V as the limiting parameters.

Second dimension gels, 1 mm thick, 200 mm long and 185 mm wide contained either 15% acrylamide and 0.075% bisacrylamide or 10% acrylamide and 0.05% bisacrylamide and were run overnight. After electrophoresis, the gels were fixed in 45% methanol and 7.5% acetic acid for 45 min and treated for fluorography with Amplify® for 45 min before being dried. The gels were placed in contact with X-ray films and exposed at -70° C. for 1 to 40 days. Each gel was exposed for at least 3 time periods to compensate for the lack of dynamic range of X-ray films.

Determination of MW and pI. Molecular weights of the proteins were determined by comparison with standard gels (Fey, S. J. et al., *The protein variation in basal cells and certain basal cell related benign and malignant diseases*, Faculty of Natural Science, University of Aarhus, Denmark (1984)). pI for the individual proteins on the gels was determined by the use of pI calibration kits. Landmark proteins were identified on gels by one or several of the following techniques: immunoblotting, immunoprecipitation, microsequencing or peptide mapping.

Experimental design. The study comprised three different series of analyses: database, intra- and interassay analysis. For each analysis, IEF and NEPHGE gels were run using 10% and 15% acrylamide in the second dimension. This gave us four subgroups: 10% IEF; 15% IEF; 10% NEPHGE; 15% NEPHGE. On 10% acrylamide gels, the approximate MW range of detection were between 20 and 250 kDa, while the approximate range of detection was between 6 and 125 kDa on 15% acrylamide gels. Consequently, proteins with a MW between 20 and 125 kDa were included in both databases, whereas proteins with lower and higher MW were particular to 15% and 10% DBs, respectively. Comparison of 10% and 15% DBs revealed a lower number of detectable spots in both 10% IEF and NEPHGE subgroups (see Results). Consequently, intra- and interassay analysis (see below) were only performed on 15% IEF and NEPHGE gels.

The databases were based on 10 different isolates analyzed in one set of gels. After 2-D gel electrophoresis, 5 gels with the best technical quality and with comparable optical densities were chosen for computer analysis. Before computer analysis, one gel in each subgroup was arbitrarily selected to be the "master gel" used for comparison with the other 4 database gels, the 5 intraassay gels and the 5 interassay gels (FIG. 4). The database "master gel" was used as a master for intra- and interassay analysis to ensure that a given spot had the same match number in the three series of analyses. Data from the "master gel" are only included in the database analysis. The "master gel" was from the same isolate in all 4 subgroups, whereas the identity of the isolates producing the 4 other database gels varied slightly from subgroup to subgroup (Table 3).

For intraassay analysis, 10 gels of the same sample were analyzed in one set of gels. After 2-D gel electrophoresis, 5 gels with the best technical quality and with comparable optical densities were chosen for computer analysis (Table 3).

For interassay analysis, the same sample was analyzed in 10 consecutive sets of gels on different days. After 2-D gel electrophoresis, 5 gels with the best technical quality and with comparable optical densities were chosen for computer analysis (Table 3).

For identification of proteins altered in expression by IL-1β, 10% IEF and NEPHGE gels of IL-1β exposed islets, previously analyzed visually (Andersen, et al., *Diabetes* 44:400–407 (1995)), were matched to the 10% IEF and NEPHGE DBs.

Computer analysis of fluorographs. Computer analysis was performed using the BioImage® program (version 4.6 M) on a Sunsparc workstation. First, the fluorographs were scanned and spots were identified and quantitated by the BioImage® program BioImage, Ann Arbor, Mass., USA. Next, each non-master gel was compared to the "master gel" and manually edited to ensure identification and quantitation of spots not found initially by the computer program. This comparison was performed by the same observer (H.U.A.) using the BioImage® program. Following this, the gels were matched by the BioImage® program and the accuracy of the match inspected and corrected by the same observer. Finally, data were extracted for calculations in the Quattro Pro® spreadsheet (Borland version 4.0).

To avoid the presence of duplicate spots in the IEF and NEPHGE subgroups, overlapping spots in either the basic part of IEF gels or in the acidic part of NEPHGE gels were omitted from analysis in the databases and the assay analyses.

Statistical analysis. Two different analyses were applied to distinguish the proteins altered in expression by IL-1β. In the first analysis, an alteration was considered significant if the average %IOD of a spot in IL-1β-exposed gels was higher or lower than the average %IOD±2 SD of the same spot in the DB. In the second comparison between the two groups, Student's t test was applied and P<0.01 was chosen as level of significance.

Figure 5A:
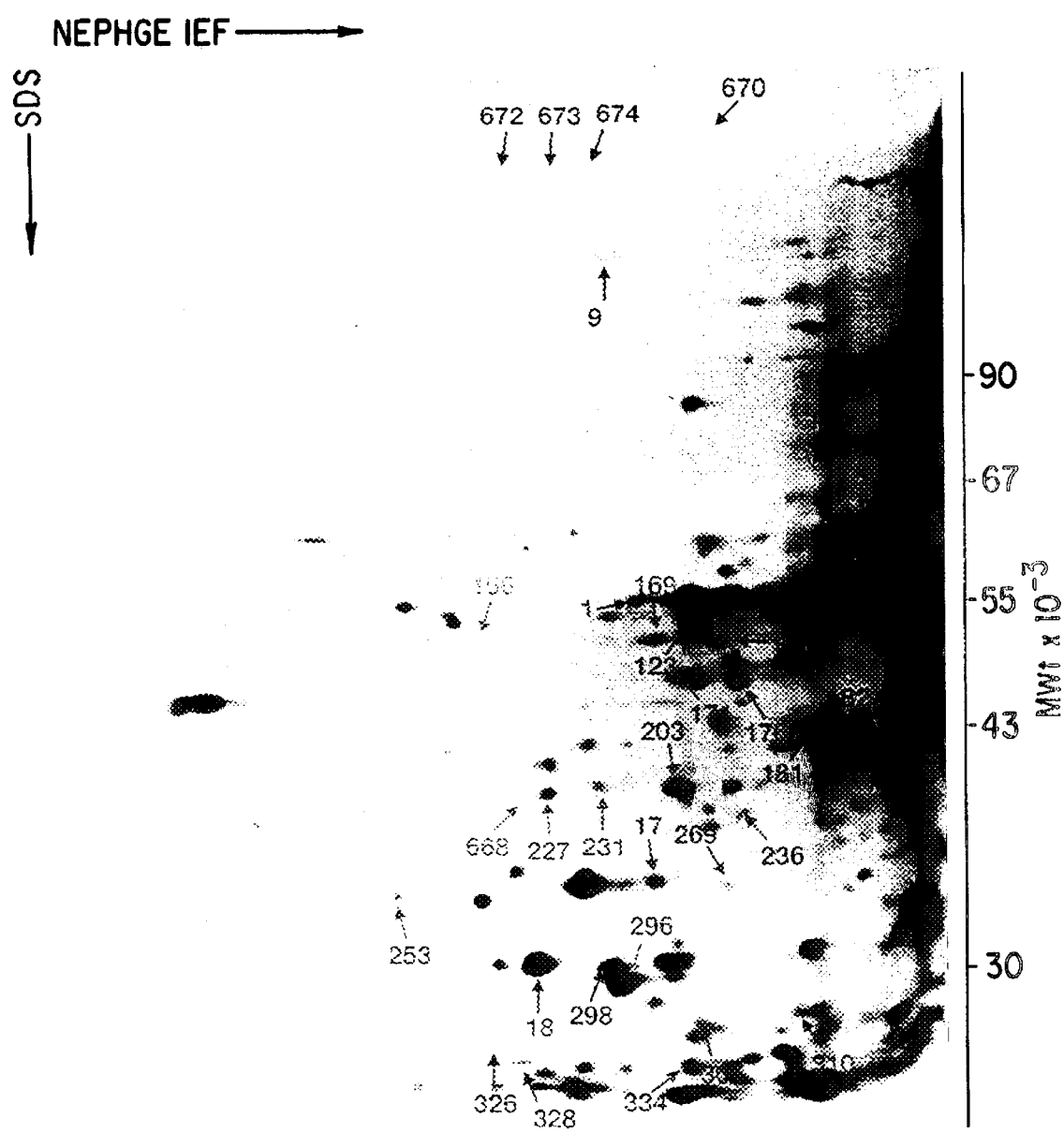
FIGS. 5A–B shows a fluorograph of the "master gel" of the 10% 2-D DB of neonatal rat islets of Langerhans incubated for 24 h in RPMI 1640+0.5% normal human serum, followed by a 4 h labelling with ($^{35}$S)-methionine. 5B an isoelectric focusing (IEF; pH 3.5–7) gel, 5A a non-equilibrium pH-gradient electrophoresis (NEPHGE; pH 6.5–10.5) gel. The arrows mark the 105 spots altered in expression by IL-1β. The numbers correspond to the match numbers of the 10% IEF and NEPHGE DB.
Figure 5B:
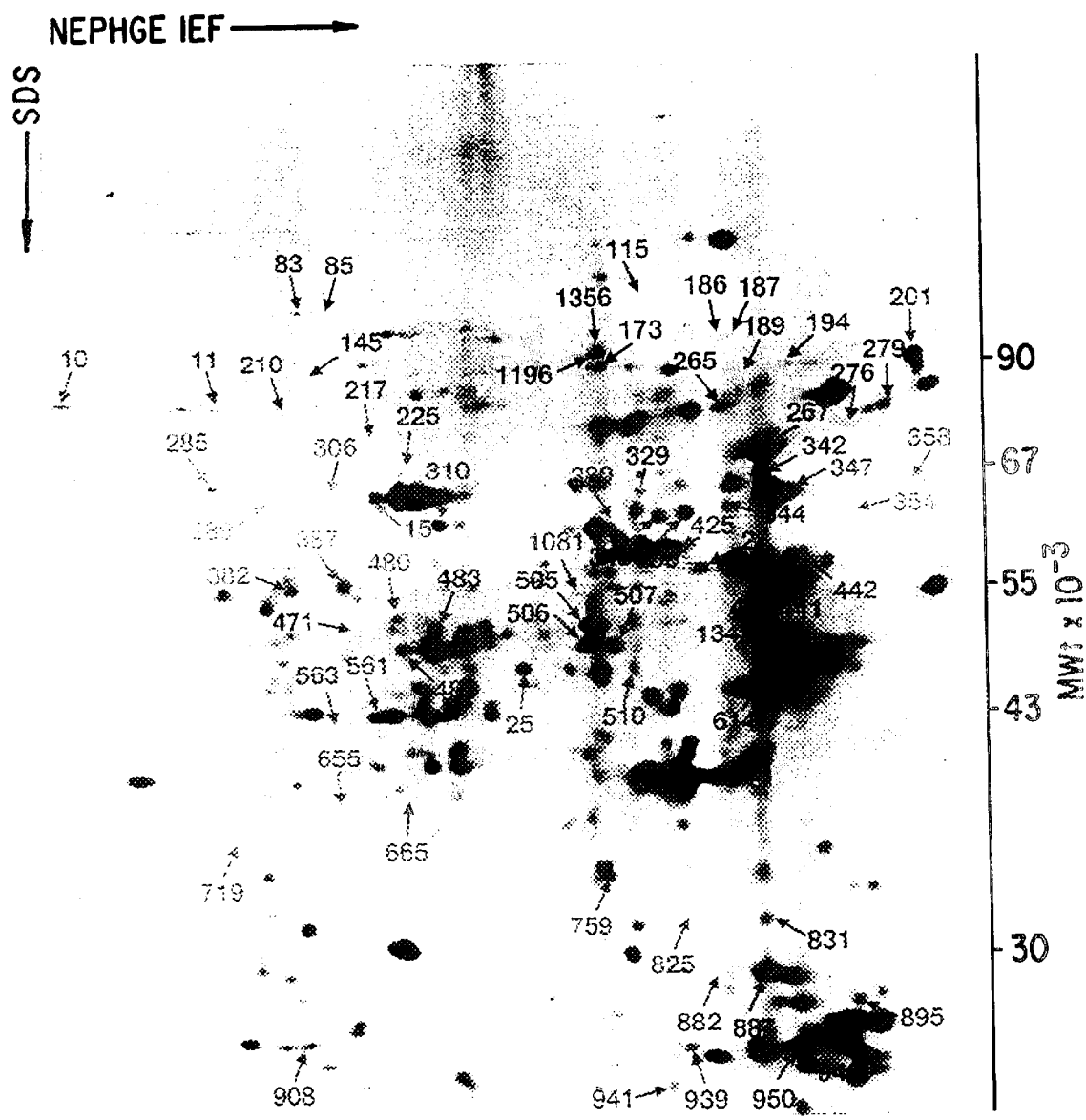
Figure 6A:
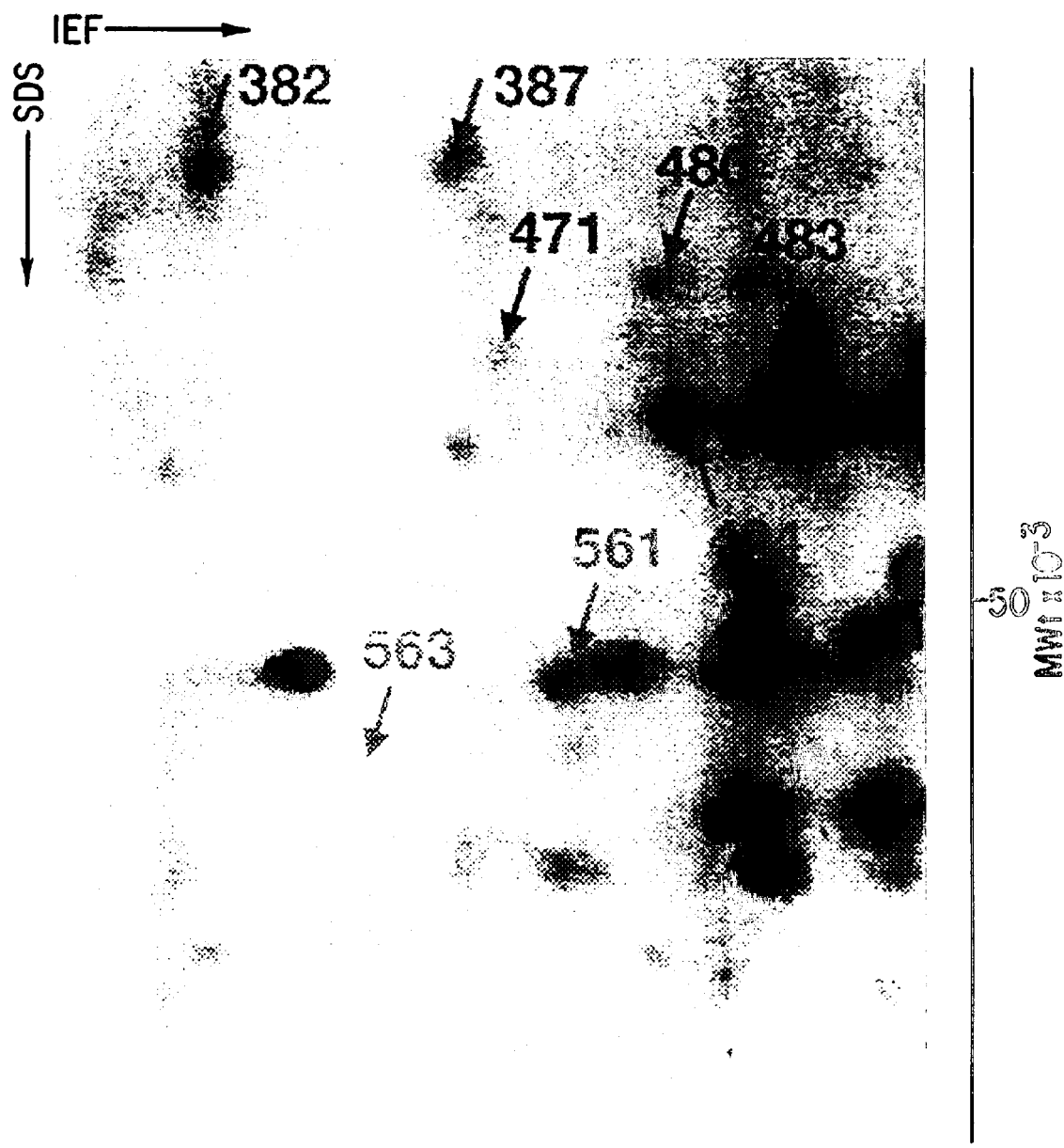
FIGS. 6A–H shows enlarged regions of the 2-D gels of the 10% IEF DB of neonatal rat islet proteins (6A–6E) and corresponding regions of gels of IL-1β-exposed islets (6F–6H). 6A: gel DB3, 6B: gel DB6, 6C: gel DB8, 6D: gel DB9, 6E: gel DB 10 ("master gel"), 6F: gel IL1A, 6G: gel IL1B and 6H: gel IL1C. The spot numbers corresponds to the numbers of the database. In the 10% IEF DB, the CV% of %IOD of the spots were as follows: 382:16.7%; 387:17.6%; 471:60.2%; 480:13.9%; 483:14.6%; 484:15.4%; 561:18.9% and 563:47.1%.
Figure 6B:
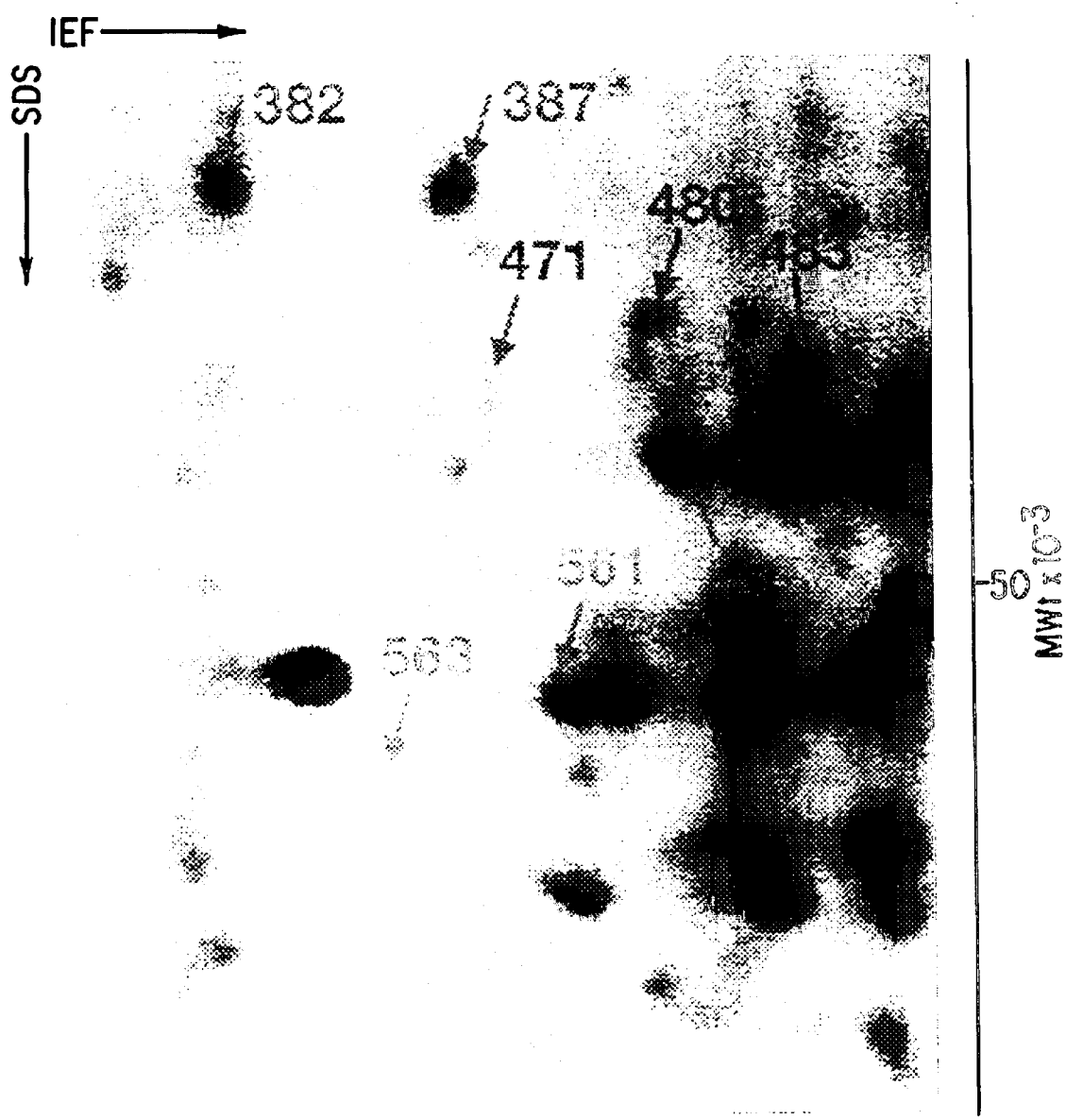
Figure 6C:
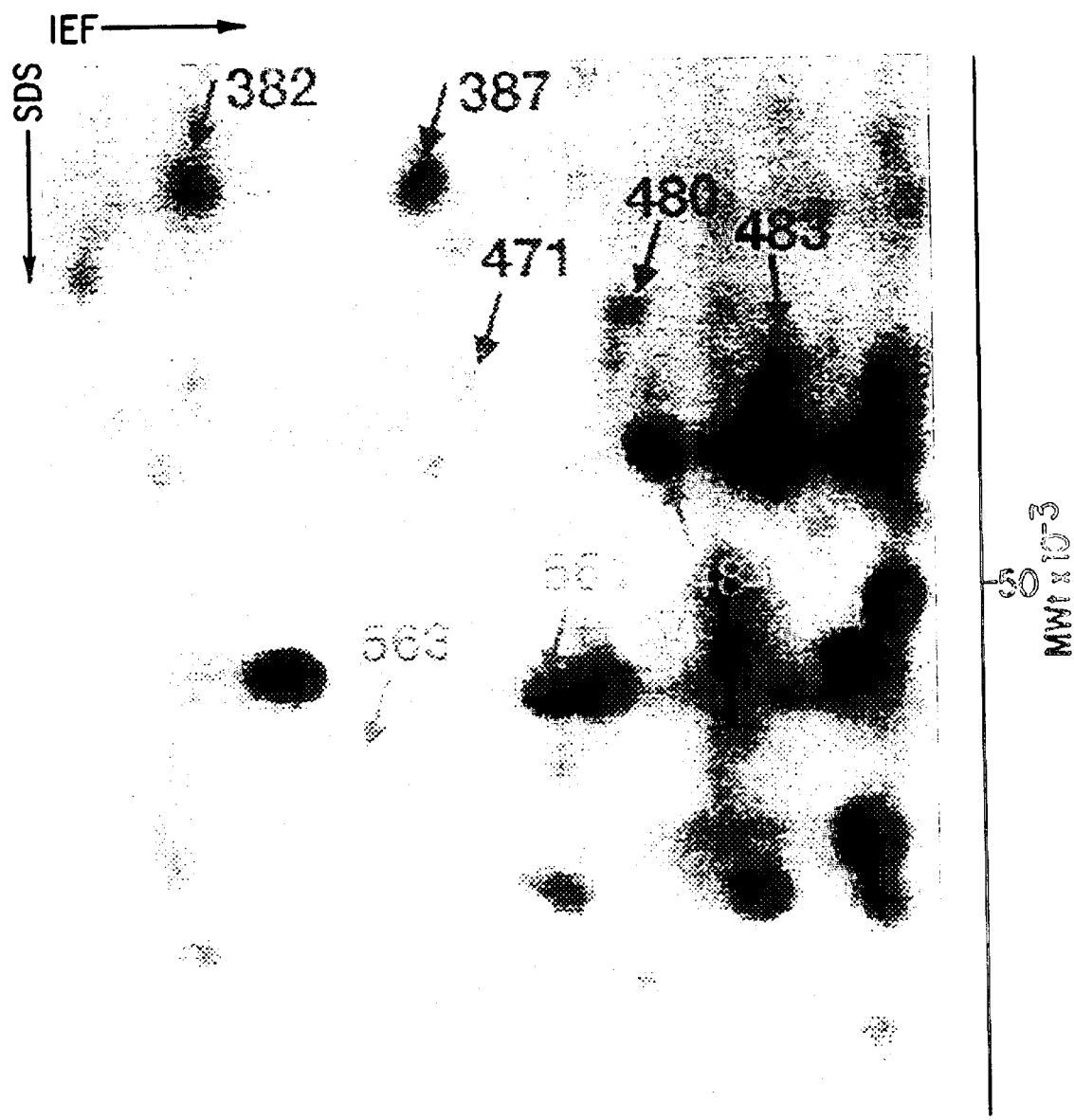
Figure 6D:
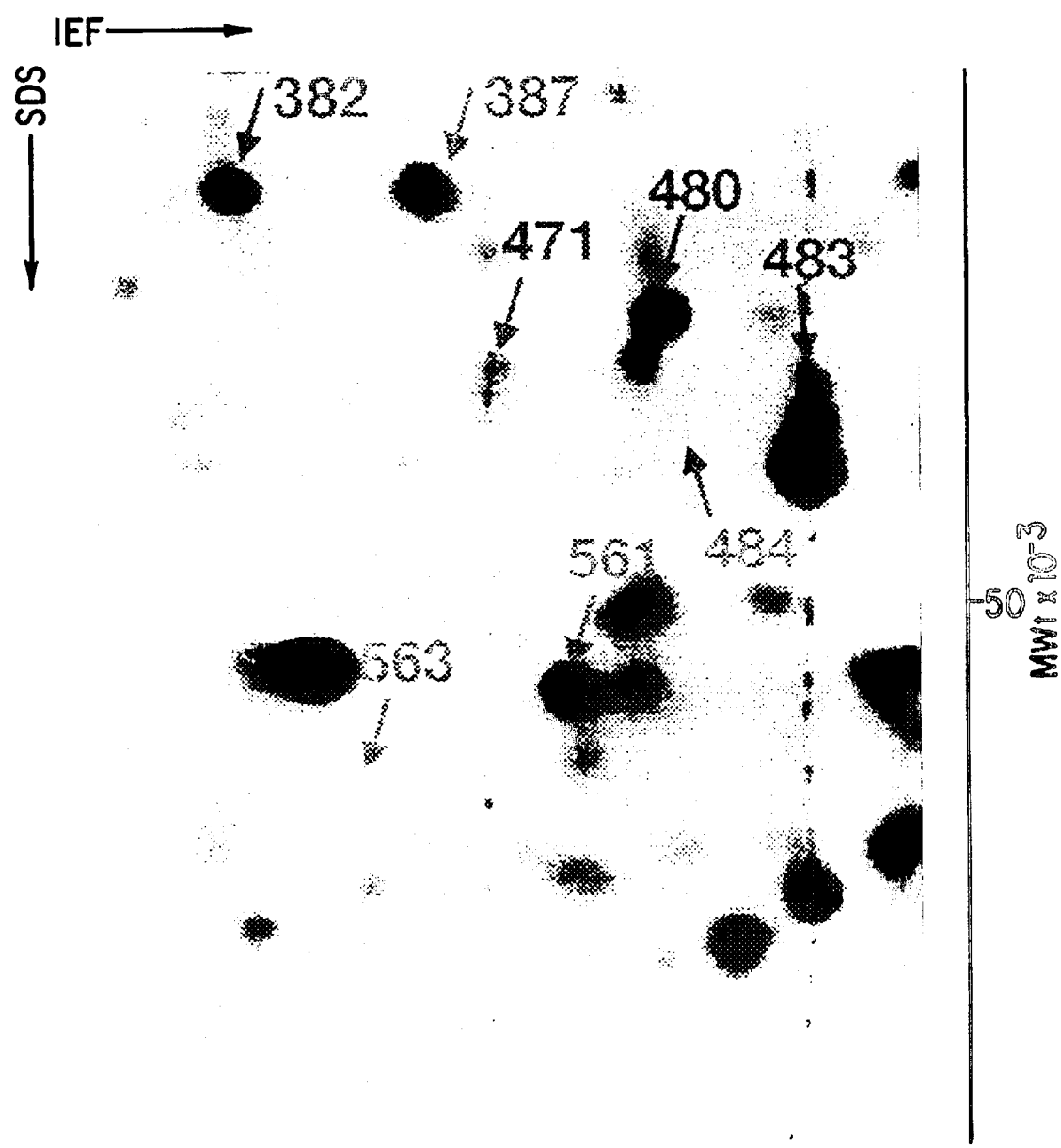
Figure 6E:
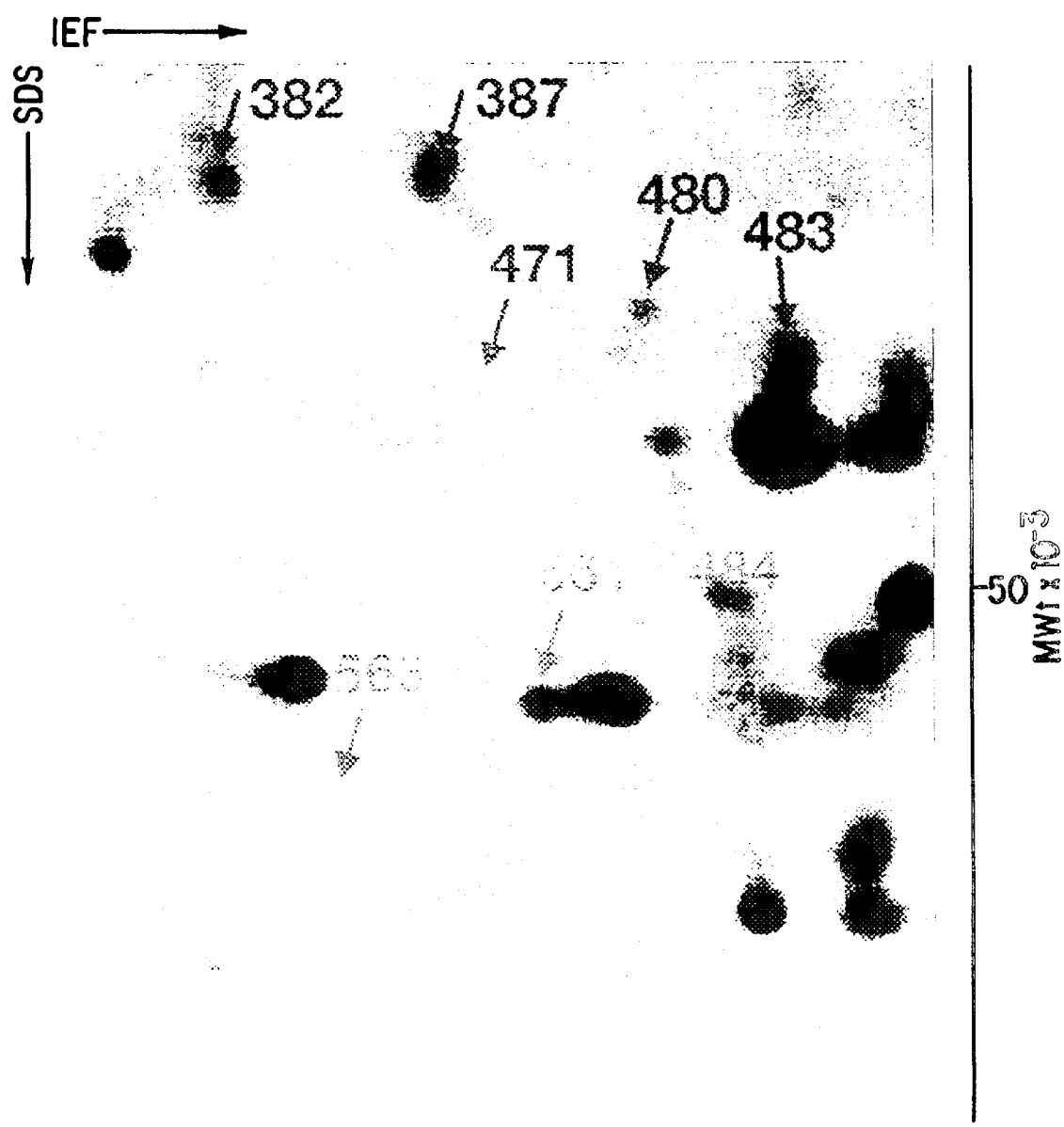
Figure 6F:
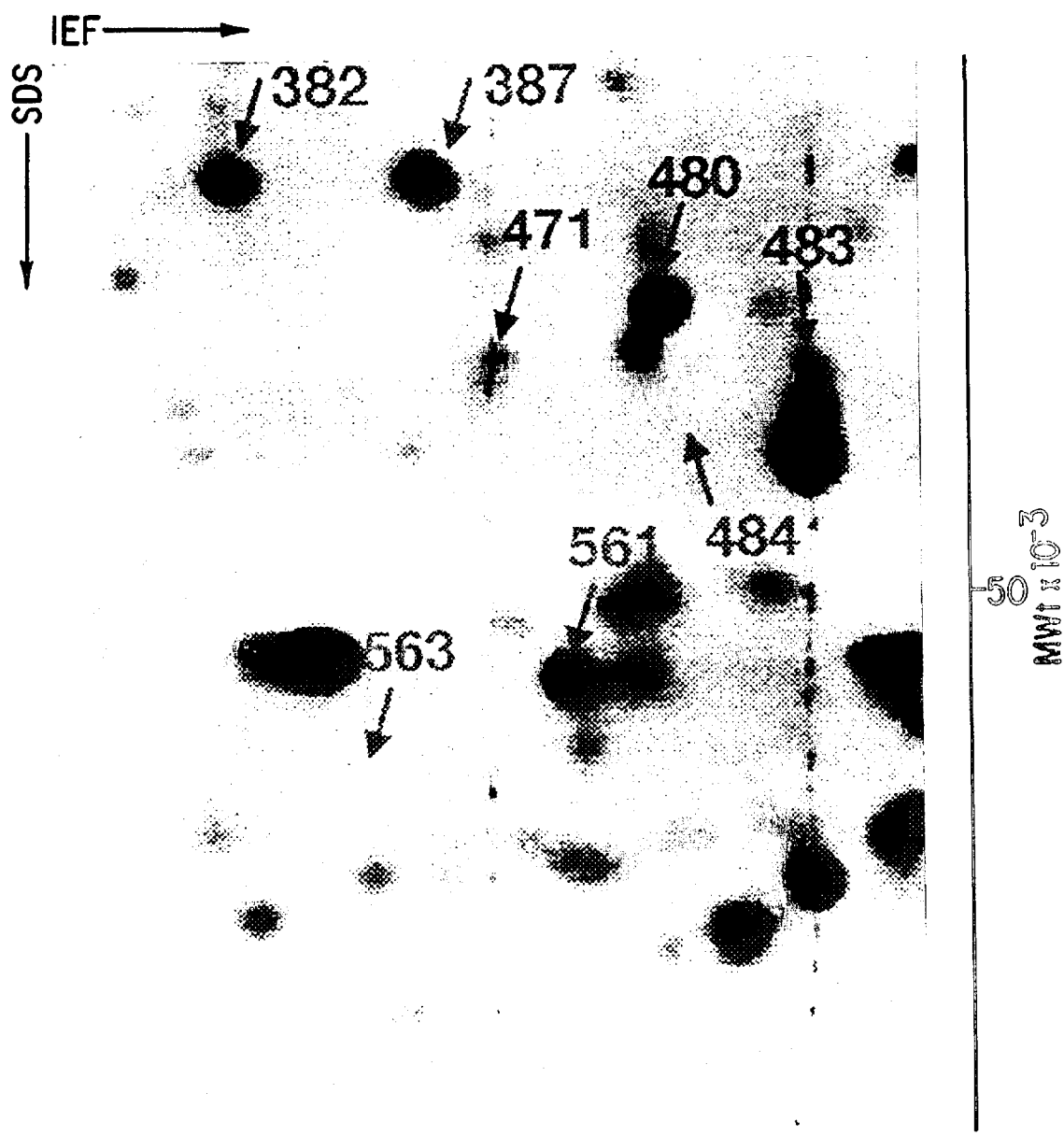
Figure 6G:
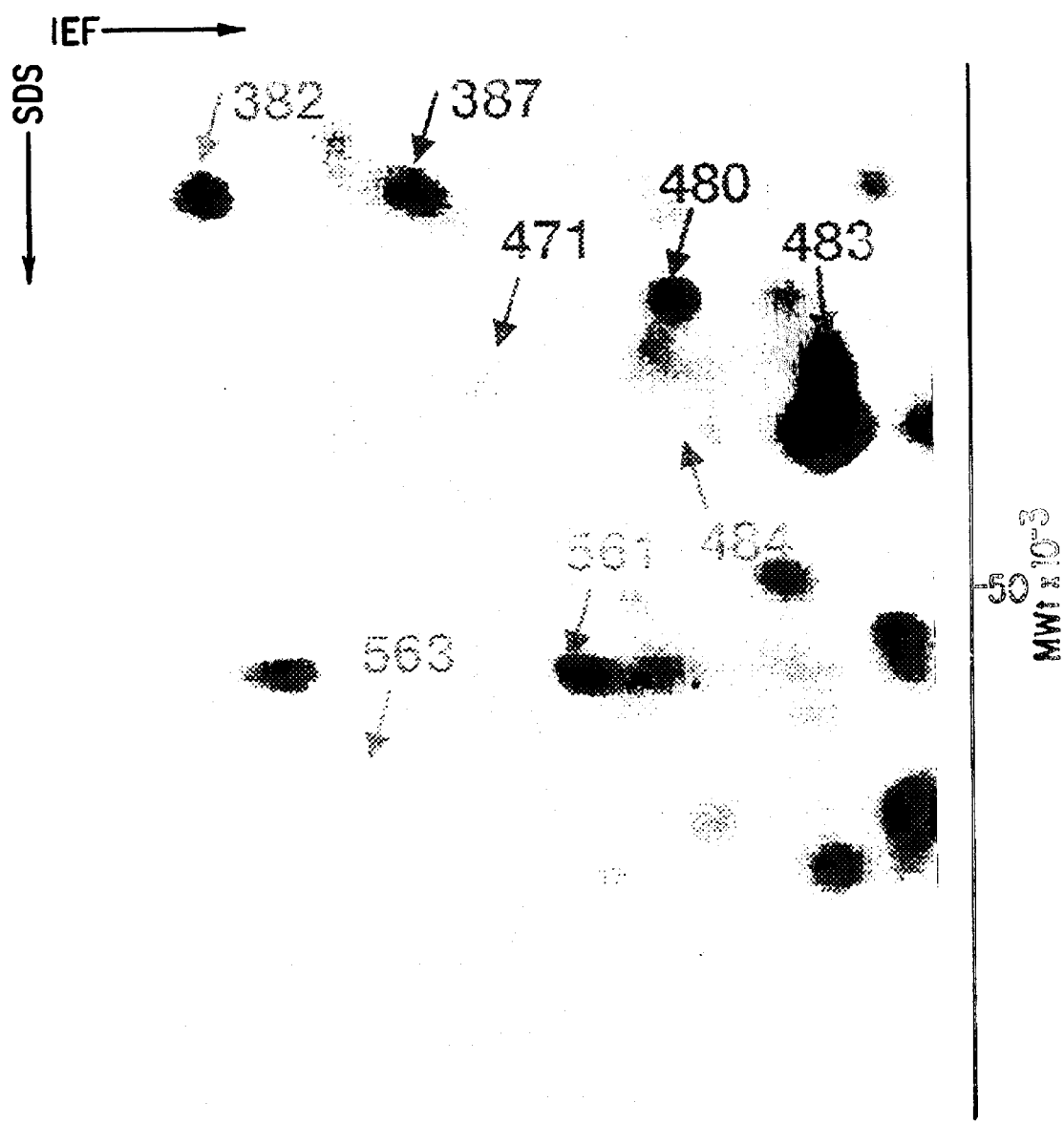
Figure 6H:
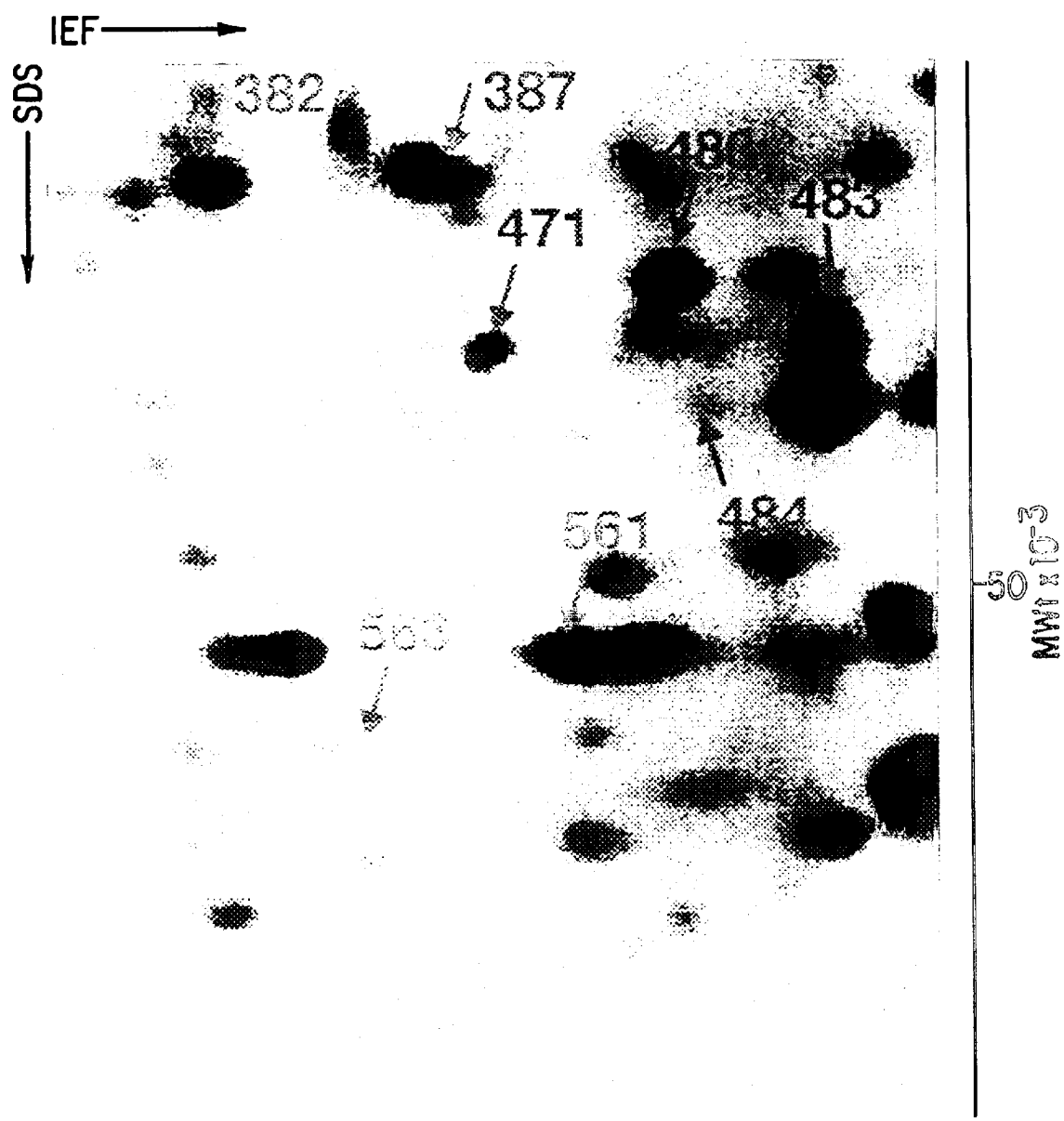
Figure 7A:
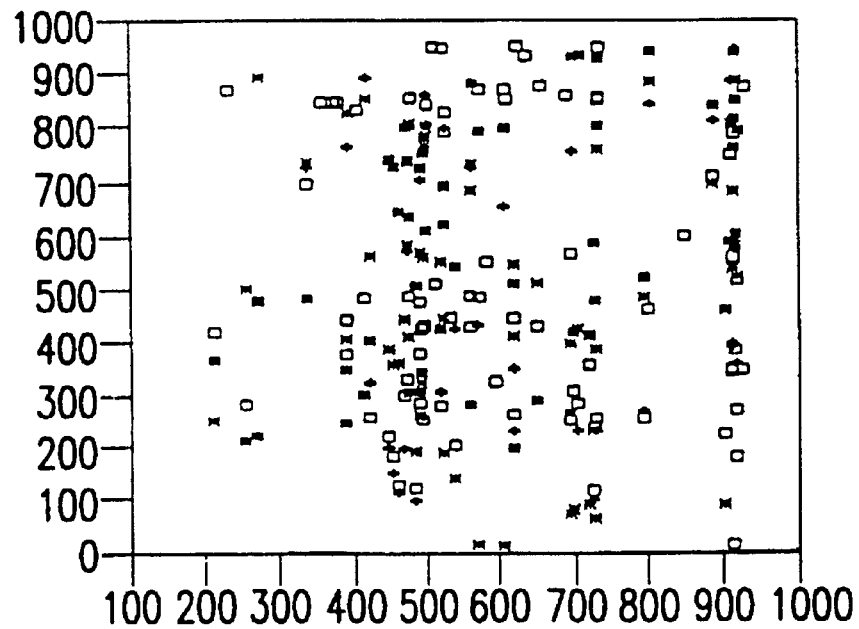
FIGS. 7A–D demonstrates that, for each DB subgroup of analysis (7A:NEPHGE 15%; 7B:NEPHGE 10%; 7C:IEF 15%; 7D:IEF 10%), the spatial location of the spots present in 1 (open square), 2 (*), 3 (+) or 4 (closed square) of 5 gels are shown. When a spot is present in more than 1 gel, the coordinates of the master image is used. When the spot is present in only 1 of the coordinates of the given gel is used.
Figure 7B:
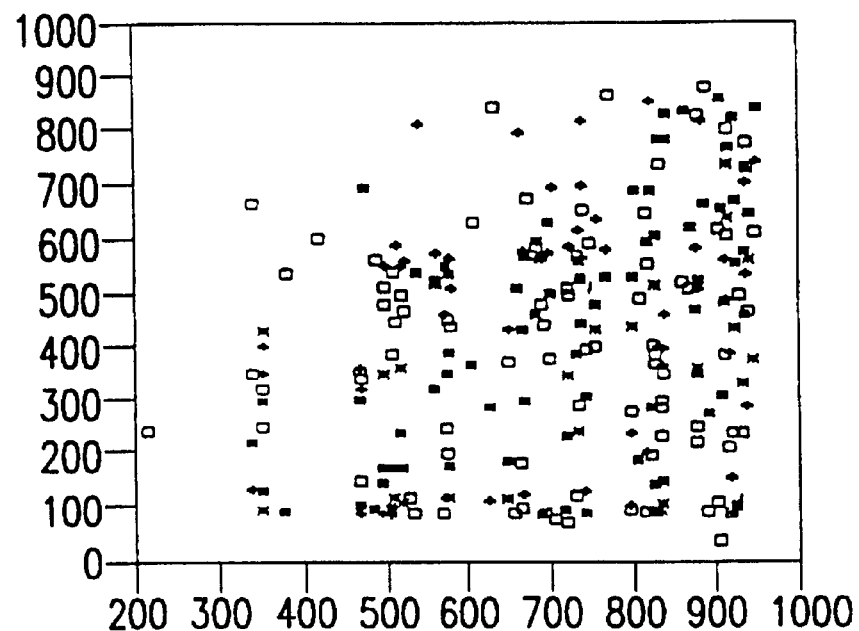
Figure 7C:
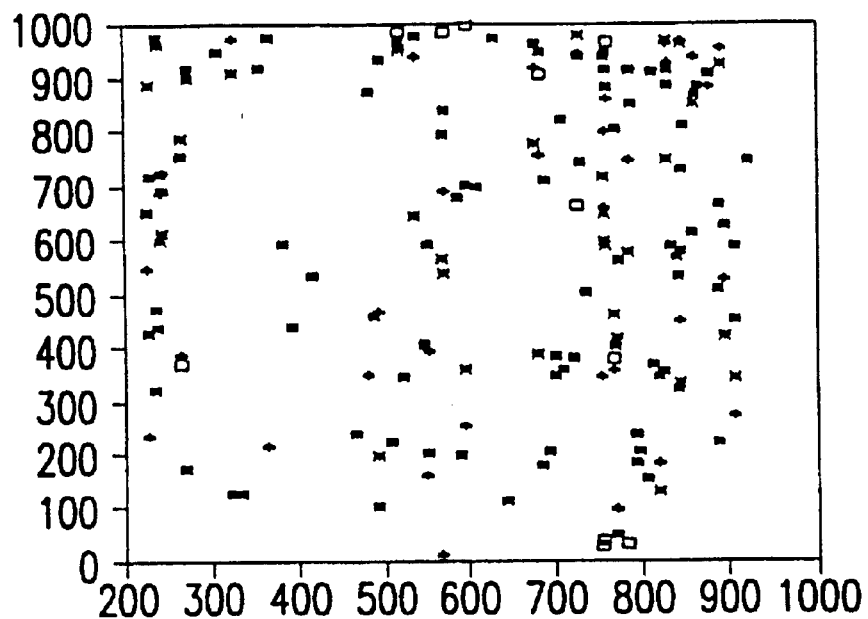
Figure 7D:
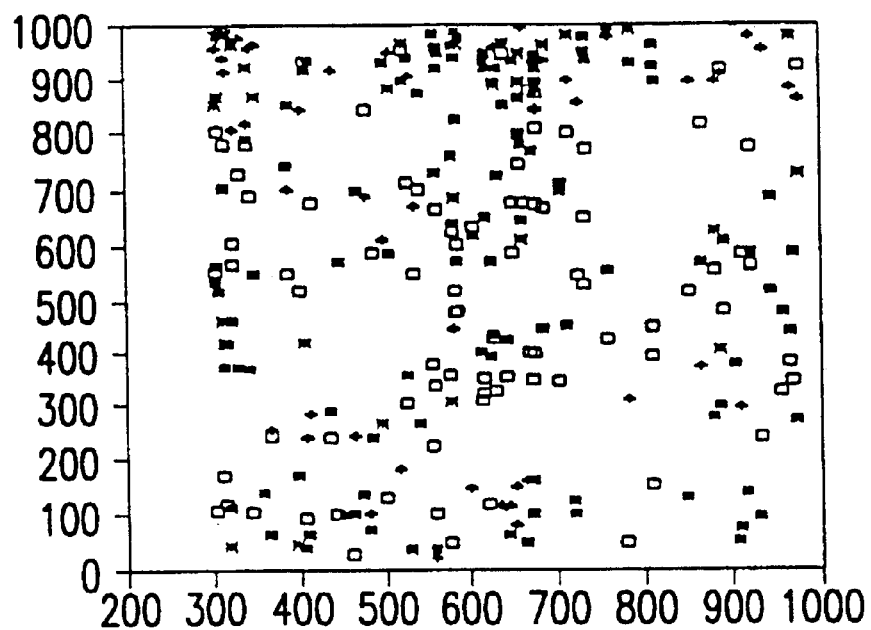
Figure 8A:
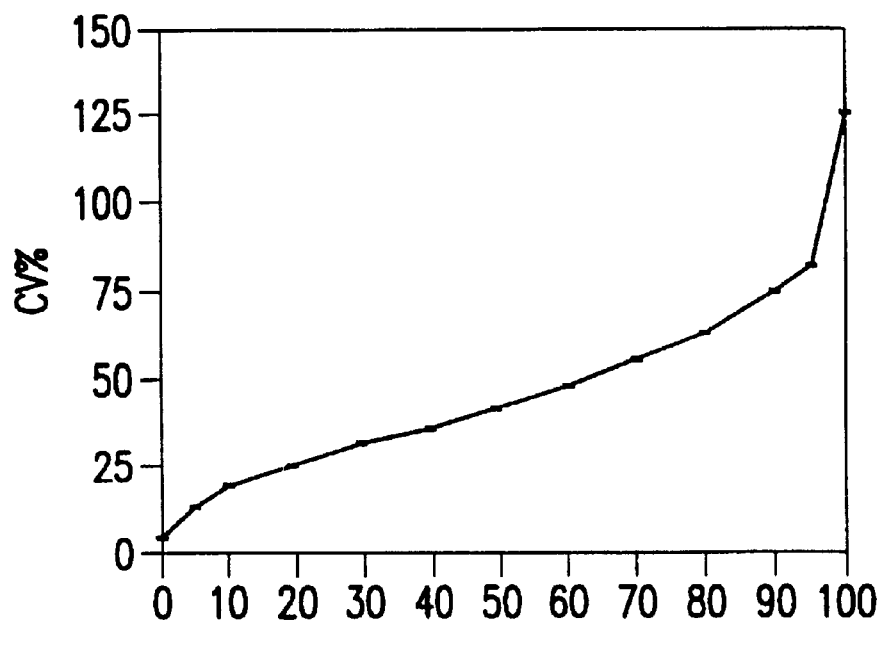
FIGS. 8A–D shows graphical data for each subgroup of analysis (8A:NEPHGE 15%; 8B:NEPHGE 10%; 8C:IEF 15%; 8D:IEF 10%), where the spots present in 5 of 5 gels were ordered after increasing coefficients of variance (CV%) of %IOD. The symbols on the graphs for "0" and "100" are the CV%'s of the spot with the lowest and highest CV% of %IOD of each subgroup, respectively. The CV% for a given percentile is the CV% of the actual spot with the 5%, 10%, 20% etc. lowest CV%.
Figure 8B:
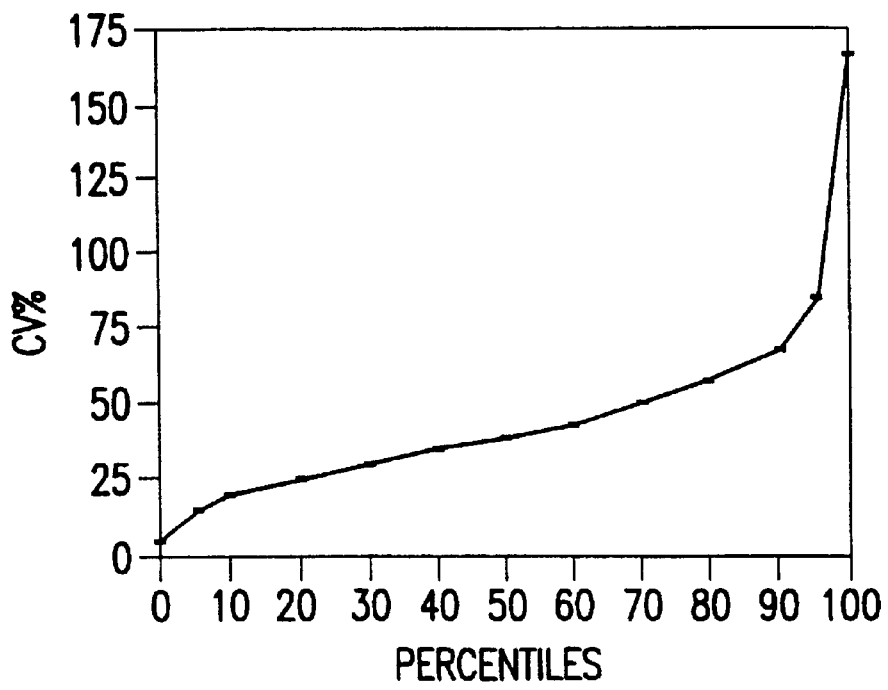
Figure 8C:
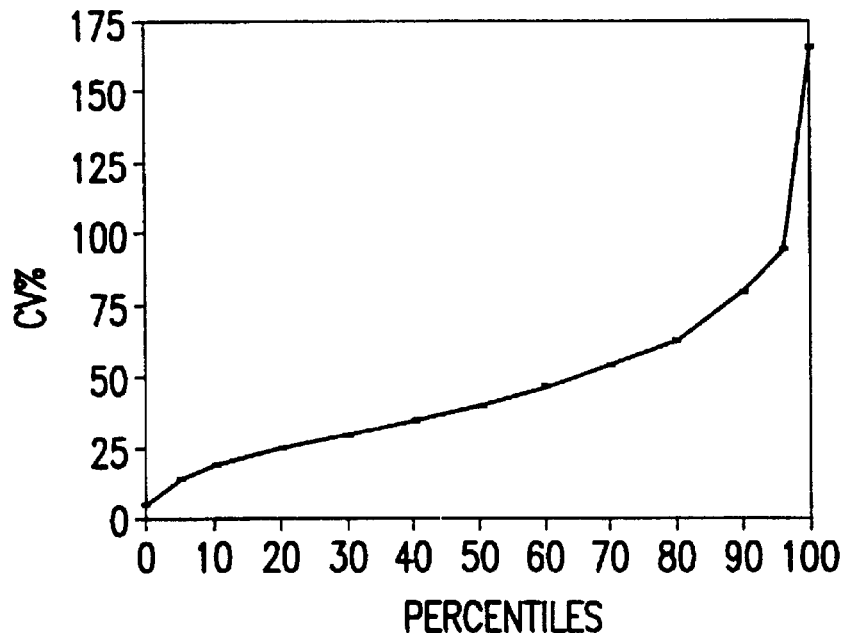
Figure 8D:
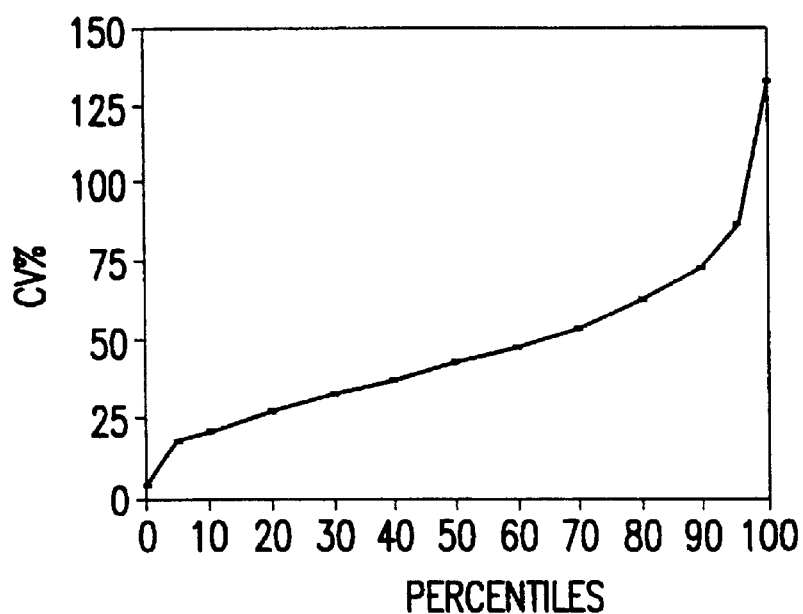
Figure 9A:
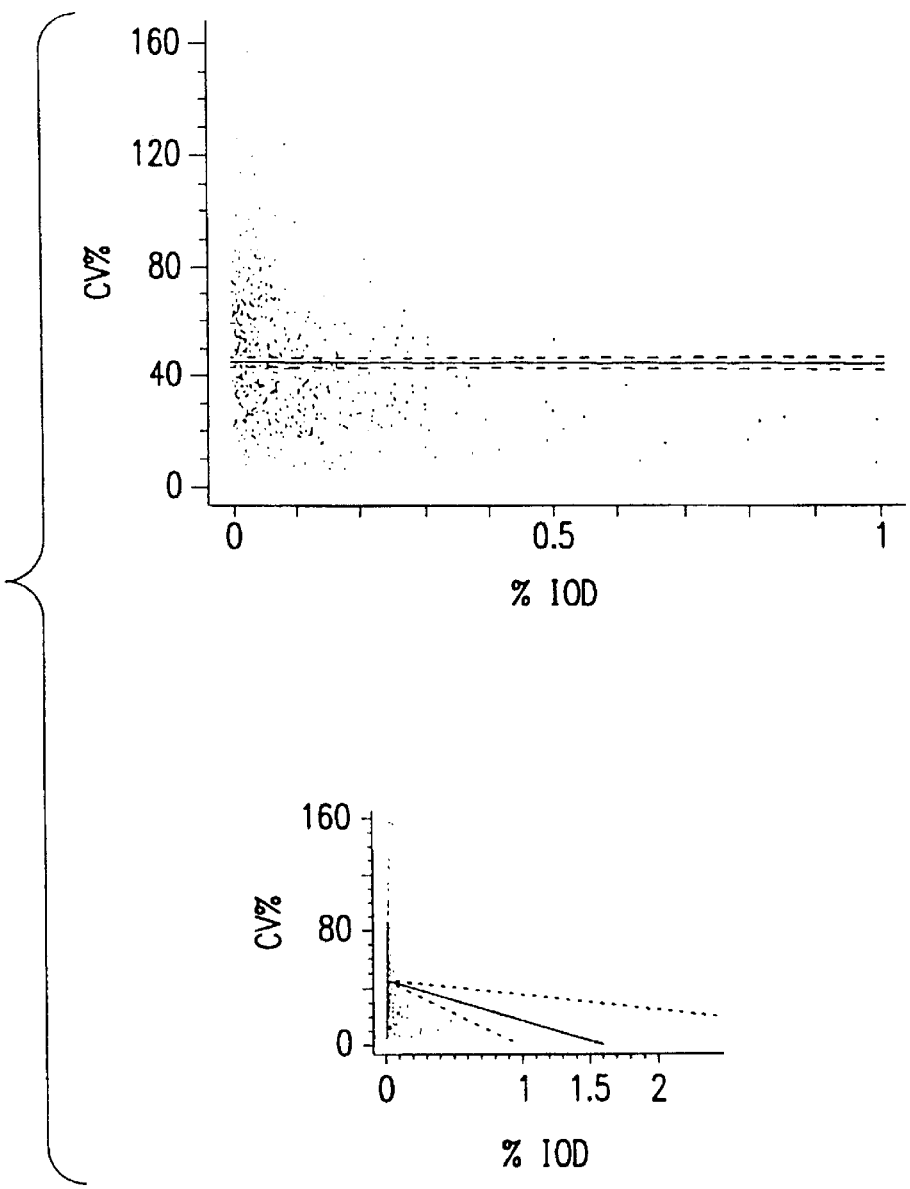
FIGS. 9A–D shows graphical data for each spot present in 5 of 5 gels in 10% and 15% IEF and NEPHGE DBs (9A:NEPHGE 15%; 9B:NEPHGE 10%; 9C:IEF 15%; 9D:IEF 10%), the average percentage of the total integrated optical density (% IOD) was calculated. For each subgroup of analysis, the spots were ordered after increasing average %IOD. The figure shows regression lines and 95% confidence intervals for all spots (insert) and for spots with a %IOD≦1 (main figure). The main figures included the following fractions of the total number of spots: IEF 15% DB: 1224/1235 (99.1%); NEPHGE 15% DB: 547/557 (98.2%); IEF 10% DB: 981/995 (98.6%); NEPHGE 10% DB:366/378 (96.8%). The results of the regression analyses were: IEF 15% DB: y=46.1−0.093x, $R^2$=0.0072, p=0.00288; NEPHGE 15% DB: y=44.7−0.028x, $R^2$=0.0160, p=0.00282; IEF 10% DB:Y=47.3−0.165x, $R^2$=0.0317, p=0.00 (t=−5.69); NEPHGE 10% DB:y=43.9−0.060x, $R^2$=0.0273, p=0.00127.
Figure 9B:
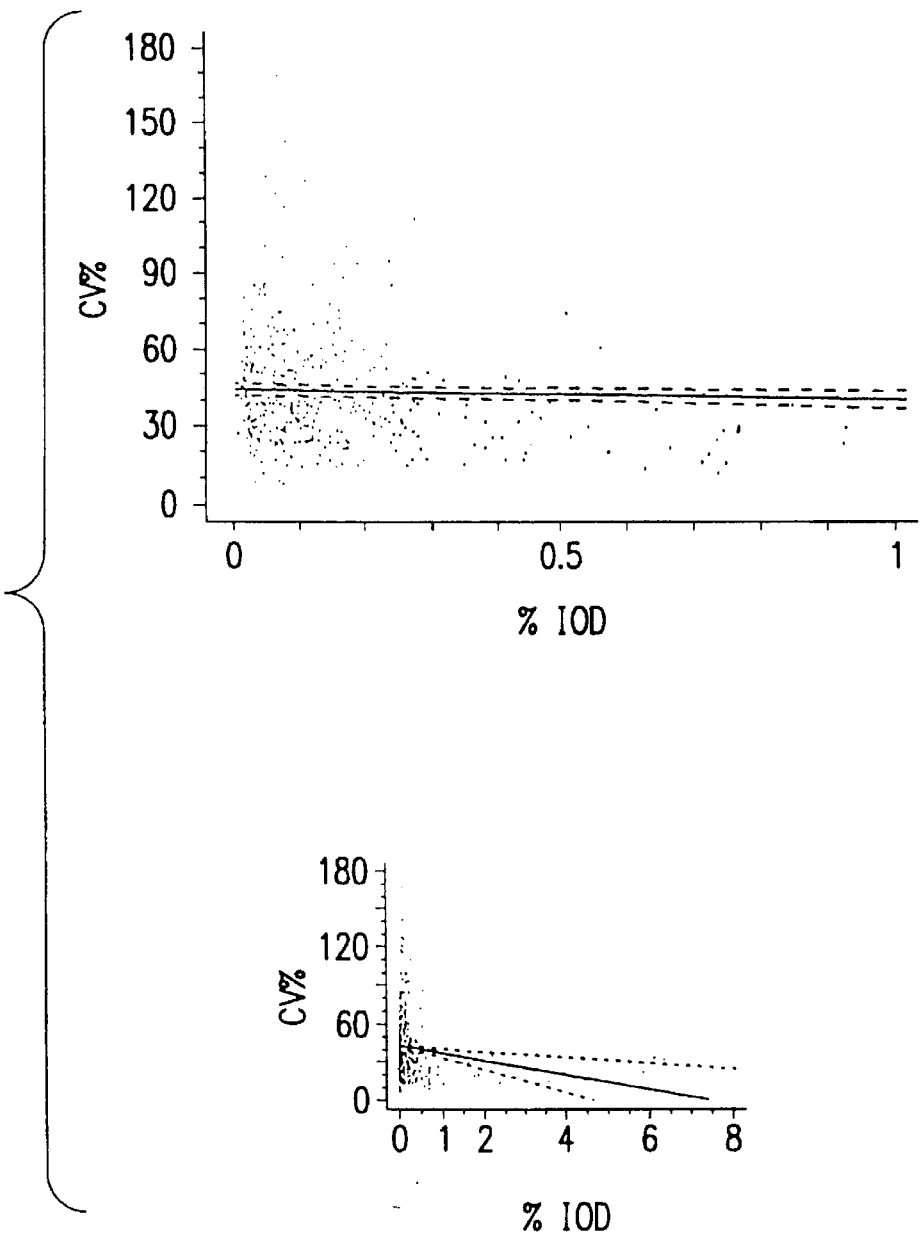
Figure 9C:
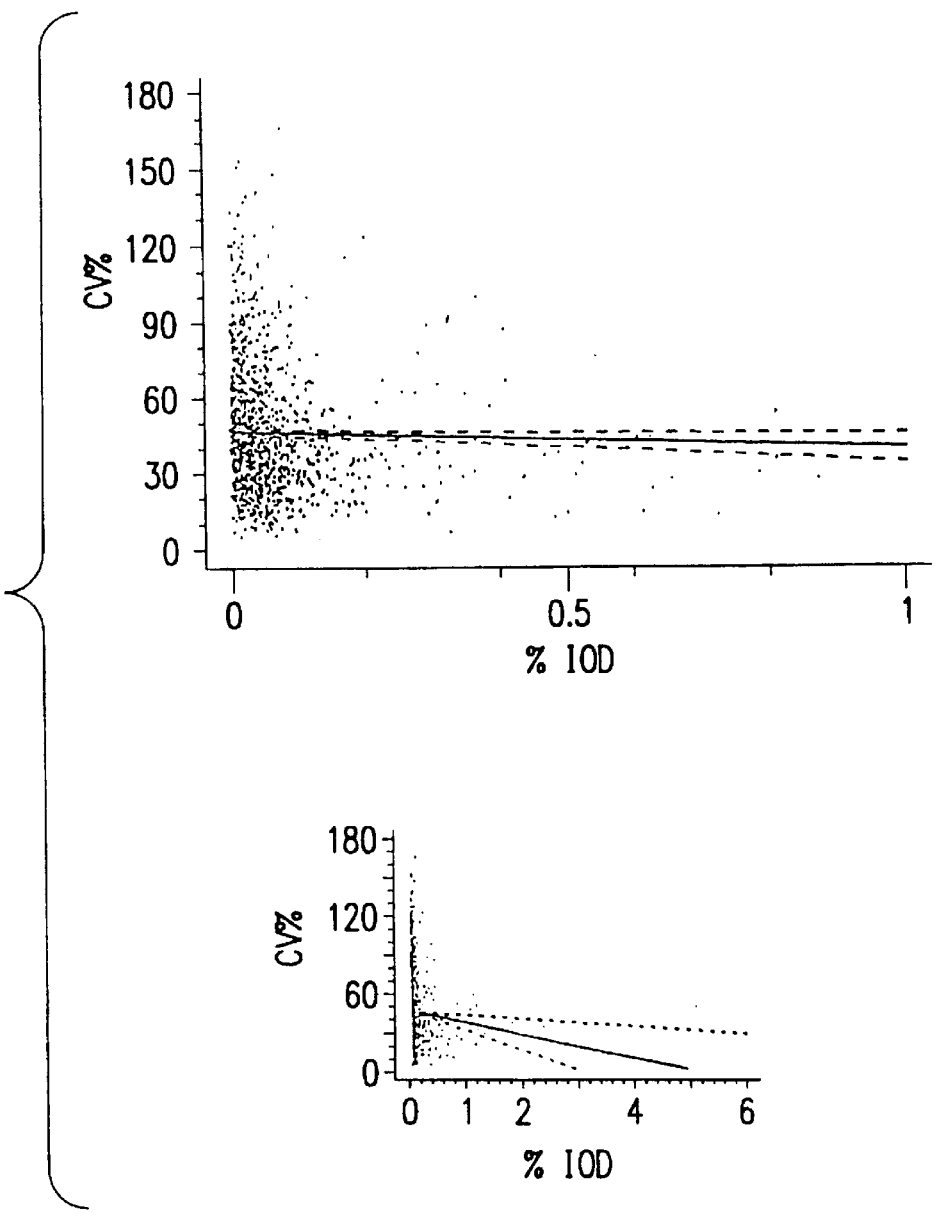
Figure 9D:
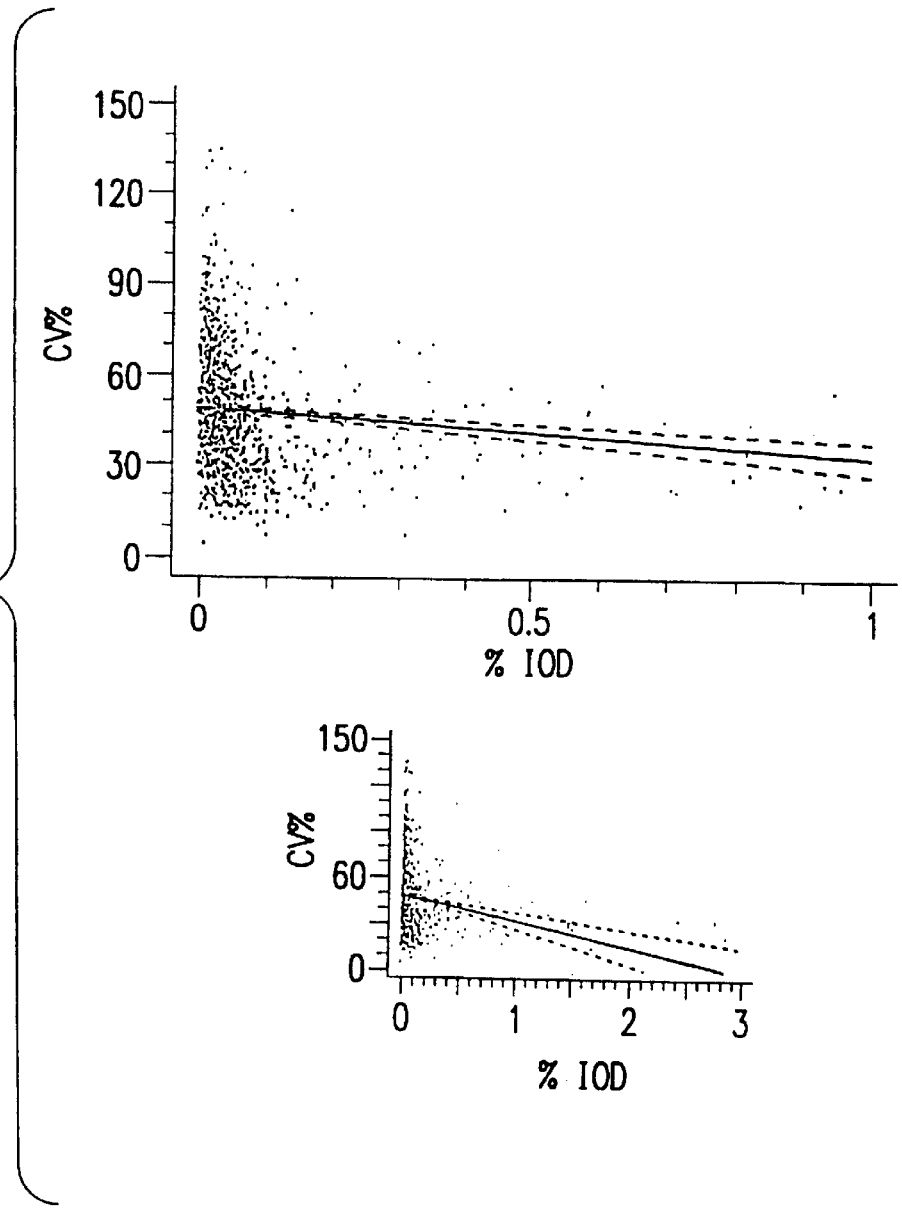

Qualitative reproducibility of the neonatal rat islet protein databases and assay analyses. 1293 to 1411 (IEF) and 605 to 764 (NEPHGE) spots were found in the individual gels used to construct the 15% DB, whereas 1101 to 1200 (IEF) and 462 to 577 (NEPHGE) spots were found in the gels used for the 10% DB (Tables 4 and 5). FIG. 5 shows the "master gels" of the 10% IEF and NEPHGE DB. In total, 1792 spots were present in 5 of 5 gels in the 15% DB, whereas 1373 spots were present in 5 of 5 gels in the 10% DB, yielding a qualitative reproducibility (the average of the percentage of spots found in 5 of 5 gels) in the subgroups between 75.2% (NEPHGE 10%) and 91.7% (IEF 15%) (Tables 4 and 5) (For each spot present in 5 of 5 gels, the databases consist of spot match number, %IOD for the 5 individual spots, average %IOD, standard deviation of %IOD, CV% of %IOD, MW and pI.). The reproducibility of the gels is illustrated in FIG. 6A–H, showing enlarged regions of the 5 gels in the IEF 10% DB.

As demonstrated in Tables 4 and 5, the total number of spots in the individual gels as well as the number and percentage of spots present in 5 of 5 gels were fewer in the 10% DB than in the 15% DB. However, if the databases were extended to include spots present in at least 3 of 5 gels, no differences in the percentage of spots present were found between the two databases (IEF: 15%: 98.8±1.2; 10%: 97.4±1.5; NEPHGE: 15%: 94.8±5.7; 10%: 94.1±3.5, Tables 4 and 5). In both databases, the percentage of spots present in 5, 4, 3 or 2 of 5 gels were lower in NEPHGE gels than in IEF gels (Tables 4 and 5). The spatial location of the spots present in less than 5 gels was investigated in FIGS. 7A–D, demonstrating that the spots were not grouped in specific areas of the gels depending on whether the spot was present in 1, 2, 3 or 4 gels.

Intra- and interassay analyses were only performed on 15% gels, since the number of detectable spots was higher in this database. In both analyses, the number of spots in the individual gels as well as the number and percentage of spots present in 5 of 5 gels were slightly (9%–19%) reduced compared to the 15% DB (compare Tables 4 and 6).

Quantitative reproducibility of the neonatal rat islet protein databases and assay analyses. The quantitative reproducibility was defined as the average of the CV% of %IOD for each spot present in 5 of 5 gels. For the databases, the average CV% was at a comparable level (42.4%–45.7%) in both 10% and 15% IEF and NEPHGE subgroups of gels (Table 7). For all DB subgroups the CV% ranged between 3.0% and 167.9% (Table 7). 10% IEF DB spots with low, intermediate and high CV% are shown in FIGS. 8A–D. For interassay analyses, the average CV% were 35.5%–36.1% for both IEF and NEPHGE gels, whereas the average CV% was 30.2% for the intraassay analysis of IEF gels and 45.7% for NEPHGE gels.

Subsequently, the database spots present in all gels were ranked in increasing order of CV% of %IOD, resulting in similar sigmoid-shaped curves for spots in all four database subgroups (FIGS. 9A–D). Thus, 30% of the spots had a CV% that was lower than 29.7%–32.5%, 50% of the spots had a CV% that was lower than 37.8%–42.8%, 90% of the spots had a CV% that was lower than 68.4%–80.6%. (FIGS. 9A–D). The slopes of the curves indicate that the 5%–10% spots with the highest CV% contribute significantly to the average CV% of %IOD (FIGS. 9A–D). This is supported by the fact that the median values of the database subgroups are 2.3% to 5.5% lower than the mean values of the subgroups (Table 7).

Regression analyses between the average %IOD and CV% of %IOD for each spot in the database subgroups. In the NEPHGE 10% and 15% DB subgroups, 2 and 6, respectively, of the 10 spots with the highest average IOD% were found in the percentile with the lowest CV% (see above). Although none of the 10 spots with the highest average IOD% were found in this percentile in the IEF DB subgroups, regression analyses were performed to investigate whether a correlation existed between spot average %IOD and CV%. Regression analyses demonstrated that a significant negative correlation existed between these two parameters (range: p=0 (IEF 10%)–p=0.00288 (IEF 15%), FIGS. 9A–D). However, since the $R^2$-values were very low for all subgroups (range: $R^2$=0.0072 (IEF 15%) $R^2$=0.0317 (IEF 10%), FIGS. 9A–D), the majority of the variability-of CV% is not explained by variation in average %IOD. In FIGS. 9A–D, the regression line for all spots in a given subgroup is shown as inserts, while the main figures show the regression lines in the interval between 0 and 1% IOD, including 96.8%–99.1% of all spots, demonstrating that the regression lines are almost horizontal in the interval of %IOD containing most spots.

Application of the 10% IEF and NEPHGE DB to distinguish proteins altered in expression by IL-1β. In a recent paper, we demonstrated that IL-1βB up and downregulated 29 and 4 proteins, respectively in 2-D gels of neonatal rat islet proteins (Andersen, et al., *Diabetes* 44:400–407 (1991)). 10% gels were prepared from (35S)-methionine labelled Wistar Furth neonatal rat islets cultured under similar conditions as the present study. Consequently, the rat islet 10% IEF and NEPHGE DB was used for comparison with the computer analyzed gels of IL1β-exposed islets, analyzed visually in the previous paper (Andersen, et al., *Diabetes* 44:400407 (199 1)). Using ±2 SD of IOD% of each DB spot as a cutoff level (comparable to the criterion for significant up- or down regulation in the visual analysis), comparison with the 10% DB confirmed 32 of these alterations and as expected identified several new protein changes. Thus, a total of 183 spots were upregulated, 113 downregulated and 34 synthesized de novo by IL-1β (results not shown). When using p<0.01 as a cutoff level in a Student's t test, the final analysis showed that 52 spots were upregulated, 47 downregulated- and 6 synthesized de novo by IL-1β, 13 of these included in the 33 spots selected by visual analysis.

Discussion

In this study, we present a 10% and 15% acrylamide 2-D gel protein DB of neonatal rat islets of Langerhans, comprising the first protein databases of islets or insulin secreting cells in any species. 1792 spots were present in 5 of 5 gels in the 15% DB, whereas 1373 spots were present in 5 of 5 gels in the 10% DB, yielding a qualitative reproducibility between 75.2% and 91.7%. In both databases, the average CV% of %IOD was between 42.4% and 45.7%. Applying the 10% DB to distinguish proteins altered in expression by IL-1β, 105 currently unidentified protein spots were found to be up-/down-regulated or synthesized de novo by IL-1β.

Characteristics of neonatal Wistar Furth rat islets. To reduce variability, the inbred Wistar Furth strain of rats was chosen as an islet donor for our databases. This strain is the inbred variant of the outbred Wistar routinely used for islet experiments in our lab (Andersen, et al., *Diabetes* 43:770–777 (1994)). We have previously determined that the function of Wistar Furth neonatal rat islets cultured with or without IL-1β is comparable to that of Wistar neonatal rat islets (Andersen, et al. *Diabetes* 44:400–407 (1995); Andersen, et al., *Acta Endocrinol.* 120:92–98 (1989)) and have determined the effects of IL-1β on the 2-D gel protein pattern of Wistar Furth islets (Andersen, et al. *Diabetes* 44:400–407 (1995)). Since the present databases are based on neonatal, and not adult rat islets, we can not exclude that the protein pattern of adult islets will be different. However, adult and neonatal islets from outbred Wistar rats are equally sensitive to the deleterious effect of IL-1. (Mandrup-Poulsen, et al., *Diabetes* 36:641–647 (1987)).

Each litter of newborn rats used for islet isolation typically consists of 8–12 pups with a varying frequency of males and females. Since comparison of Coomassie Blue-stained gels of liver proteins from male and female outbred Wistar rats revealed quantitative differences in 7 of 250 analyzed spots and since six proteins were found exclusively in males and one protein exclusively in females (Steiner, et at., *Electrophoresis* 16:1969–1976 (1995)), it is likely that some of the proteins in our database are gender-specific or gender-regulated. Consequently, it is possible that the high variation of some of the spots in our databases could be reduced if we had chosen to construct separate databases of islets from male and female rats. However, the gels of liver proteins were performed on non-cultured cells which could mean that the sex-determined protein variability could be induced by circulating sex steroids and not an inherent trait of the liver cells per se. Circulating hormones are not likely to interfere in our protein pattern since I) we preculture our islets for 4 days before experiments and II) no differences in serum concentrations of sex steroids are found before puberty. Further, we have previously demonstrated that islets from male and female outbred Wistar rats are equally sensitive to the deleterious effect of IL-1 (Steiner, et al., *Electrophoresis* 16:1969–1976 (1995)).

Detection of islet proteins. Not all spots detected in our databases will represent different protein entities, since some spots can represent modifications (e.g. acetylation, methylation, phosphorylation or carbamylation) of other proteins. However, the detected number of spots is an underestimation of the total number of islet proteins, since the protein database does not include proteins below the limit of sensitivity, proteins not containing methionine, proteins with a molecular weight below 6 kDa or above 250 kDa or proteins with a pH below 3.5 or above 10.5. Further, about 40% of the spots with IODs above limits of detection have previously been estimated to be missed because they are obscured by other spots (Garrels, *J. Biol. Chem.* 264:5269–5282 (1989)). Finally, the 4 h labelling period favours the labelling of proteins with high synthesis rates, whereas longer labelling periods could be required to produce databases where all proteins are in steady-state.

Qualitative reproducibility. Previous reports of the qualitative reproducibility of 2-D gel protein databases are few and the results variable: In a mouse liver protein database of Coomassie Blue-stained 2-D gels, 826 spots were present in the master image and on the average 500 spots were matched in 85% of the other mouse liver patterns (Giometti, et al., *Electrophoresis* 13:970–991 (1992)). In protein databases of ($^{35}$S)-methionine labelled mouse embryos over 80% of spots in each of the four gel images were automatically matched to the standard image (Shi, et al., *Molec. Reprod. Develop.* 37:34–47 (1994)). In our study, 1792 spots (75.2%–91.7%) were present in 5 of 5 gels in the 15% DB, whereas the average percentage of spots present in 5 of 5 gels was 5–10% lower in the 10% DB. This is presumably due to the fact that fewer proteins exist in the high molecular weight region only analyzable on the 10% gels than in the low molecular weight region only analyzable on the 15% gels. In all groups analyzed, the qualitative reproducibility of NEPHGE gels was lower than IEF gels. Since NEPHGE gels, contrary to EF gels, are non-equilibrium gels the risk that identical spots have a slightly different horizontal location is increased. However, our manual editing have ascertained that this problem has been eliminated as much as possible.

Quantitative reproducibility. Regarding the quantitative reproducibility, comparisons with other studies are difficult, since the methods used for spot identification are not identical. Further, the spots included in calculations of CV% of %IOD in most of the previously published databases are selected from the total number of matched spots according to varying criteria. In ten Coomassie Blue-stained gels of male and female Wistar rat liver proteins, 250 of more than 1,000 spots present in the "master gel" were selected according to good shape, size and resolution and the presence and good quality in previous experiments (Steiner, et al., *Electrophoresis* 16:1969–1976 (1995)). Using these criteria, one third of the spots had a CV% below 20%, more than half had a CV% below 30% and three quarters had a CV% below 40% (Steiner, et al., *Electrophoresis* 16:1969–1976 (1995)). In ($^{35}$S)-methionine labelled protein databases consisting of 5 gels of compacted eight-cell (CEC) mouse embryos and 4 gels of blastocyst-stage (BS) mouse embryos, 1,674 and 1,653 spots, respectively, were matched in all gels (Shi, et al, *Molec. Reprod. Develop.* 37:34–47 (1994)). Calculated on the basis of all matched spots, the percentage error (defined as SEM×100/average) of 74% (CEC) or 79% (BS) of these spots was below 50%, and 45% (CEC) or 47% (BS) of the spots had a percentage error below 30% (Shi, et al., *Molec. Reprod. Develop.* 37:34–47 (1994)). For comparison, conversion of SD's to SEM's (SEM=SD/$\sqrt{n}$) would give an average CV% of 20.3% in the islet IEF 15% DB, and 97.7% and 83.2% of the spots would have a percentage error below 50% and 30%, respectively.

Although the quantitative reproducibility of our study is comparable to or even better than the study in mouse embryos (Shi, et al., *Molec. Reprod. Develop.* 37:3447 (1994)), the average CV% of %IOD in our databases are still relatively high. As previously mentioned, the heterogeneous cell population of islets and the different male/female ratio of the islet isolations could contribute to gel variability. Although we have attempted to use gels with comparable total optical densities (the largest difference within each subgroup was by a factor of 3.5 (gel DB10 vs. gel DB3, IEF 15% DB, Table 3)), the non-linear saturation of X-ray film will contribute to the size of the CV% for all database spots. The application of phosphoimaging, a technique not available in our laboratory when this study was initiated, would reduce the contribution of this phenomenon to the magnitude of the CV%. Finally, electronic noise and differences in spot boundary definition in the computer analysis can contribute to the magnitude of the CV%. Contrary to some other gel analysis programs, the BioImage( program uses the local, and not the total background for boundary definition, reducing the contribution of the latter factor to the CV%.

Studies of replicate gels. In a study of 10 replicate gels of ($^{35}$S)-methionine labeled REF 52 cells, Garrels selected 1109 of the most prominent spots out of a total of approximately 2,000 spots and found an average CV% of 26.5%, with a range between <5% and >100% and a modal value between 10% and 15% (Garrels, *J. Biol. Chem.* 264:5269–5282 (1989)). It is unclear whether the samples were analyzed in consecutive or the same set of gels. When grouping the spots according to spot quality (fitting to Gaussian shapes, overlapping of neighboring spots) and omitting spots with low density in all gels, the 19.1% spots of the highest quality had an average CV% of 13.0% (Garrels, *J. Biol. Chem.* 264:5269–5282 (1989)). As expected, the average CV% of %IOD was reduced when the 15% IEF and NEPHGE interassay analyses were compared to the 15% IEF DB, the reduction being by approximately 9%. Since the day-to-day variation of gel preparation was eliminated in the intraassay analyses, the average CV% was expected to decrease even more. In the 15% IEF subgroup, CV% was decreased by ≈15% compared to the database, whereas no decrease was found in the 15% NEPHGE subgroup. The reason for the high average CV% in the 15% NEPHGE intraassay subgroup, which also has the lowest qualitative reproducibility of all subgroups (Tables 4–6), is unknown. As the database gels were also analyzed in one set of gels, the fraction of the CV% that is attributable to biological variation should be given by the difference in CV% between database and intraassay analysis for a given spot. Thus, if the result of the 15% NEPHGE intraassay analysis is disregarded, approximately one third of the average CV% of %IOD is due to biological variation.

Effects of IL-1β on islet protein expression. IL-1β altered the expression of 105 so far unidentified proteins. IL-1β mechanism of action on islet cells is not fully clarified, but three distinct groups of proteins might play important roles: proteins participating in signal-transduction and proteins encoded by so-called early response and late response genes (Eizirik, et al., *Diabetologia* 39:875–890 (1996)). IL-1β-induced signal transduction in target cells is thought to involve four major signalling pathways: nuclear factor-κb, the stress-activated protein kinases (SAPK/JNK), protein kinase C and tyrosine kinase (Mandrup-Poulsen, T., *Diabetologia* 39:1005–1029 (1996); Eizirik, et al., *Diabetologia* 39:875–890 (1996)). The three pathways lead to a rapid and transient induction of the early response genes of which c-fos, c-jun and interferon response factor-1 have been implicated in cytokine action on islet cells. The early response genes activate specific genes with possible deleterious (iNOS, cycloxygenase-2 and lipoxygenase) and protective (HSP72, haem oxygenase, Mn superoxide dismustase) action on islets (Mandrup-Poulsen, T., *Diabetologia,* 39:1005–1029 (1996); Eizirik, et al., *Diabetologia* 39:875–890 (1996)). Thus, the information about IL-1β mechanism of action in islet cells is still limited and the identification of the 105 proteins altered in expression by IL-1β might lead to new knowledge about signal transduction and proteins with protective and deleterious actions.

Conclusion

We have established a protein database of neonatal rat islets of Langerhans with a high qualitative reproducibility and a quantitative reproducibility that improves on previously published databases on other cells and tissues. Further, we have determined intra- and interassay variations of the neonatal rat islet protein database. The database has further been applied to identify proteins altered in expression by IL-1β, which might have important roles in an IL-1β mechanism of action. Since IL-1β is cytotoxic to the insulin producing rat B cells, identification of these proteins, currently being performed by mass spectrometry and microsequencing, is expected to result in significant knowledge about the pathogenesis of insulin dependent diabetes mellitus.

TABLE 3

Correction factors between the total optical densities of master and non-master gels in DB, intra-and interassay analyses of 2-D gels of neonatal rat islet proteins.

| | IEF | | | | |
|---|---|---|---|---|---|
| DB | | Interassay | | Intraassay | |
| 15% gels | | | | | |
| gel DB10 (master): | 1 | gel IE3: | 1 | gel IA2: | 1 |
| gel DB3: | 0.293 | gel IE4: | 1.096 | gel IA3: | 0.620 |
| gel DB6: | 0.303 | gel IE8: | 1.129 | gel IA4: | 0.738 |
| gel DB8: | 0.840 | gel IE9: | 0.784 | gel IA6: | 1.014 |
| gel DB9: | 0.284 | gel IE10: | 0.804 | gel IA10: | 0.747 |

| | NEPHGE | | | | |
|---|---|---|---|---|---|
| DB | | Interassay | | Intraassay | |
| gel DB10 (master): | 1 | gel IE3: | 1 | gel IA1: | 1 |
| gel DB3: | 0.542 | gel IE4: | 1.901 | gel IA2: | 1.599 |
| gel DB6: | 1.067 | gel IE8: | 1.761 | gel IA3: | 0.841 |
| gel DB8: | 0.986 | gel IE9: | 1.408 | gel IA4: | 0.908 |
| gel DB9: | 0.831 | gel IE10: | 1.599 | gel IA5: | 1.135 |

| IEF DB | | NEPHGE DB | |
|---|---|---|---|
| 10% gels | | | |
| gel DB10 (master): | 1 | gel DB10 (master): | 1 |
| gel DB1: | 0.947 | gel DB1: | 1.660 |
| gel DB4: | 0.358 | gel DB7: | 3.215 |
| gel DB6: | 1.167 | gel DB8: | 2.959 |
| gel DB8: | 1.145 | gel DB9: | 1.197 |

The databases were based on 10 different isolates analyzed in one set of gels, while interassay analysis consisted of 10 gels of the same sample analyzed in one set of gels and interassay analysis was based on the analysis of the same sample run in 10 consecutive sets of gels on different days. Before computer analysis, one gel in each database subgroup was arbitrarily selected to be the "master gel" used for comparison with the other 4 database gels, the 5 intraassay gels and the 5 interassay gels. The numbers (1–10) of the isolates/replicates chosen are indicated in the Table. The correction factors between the total optical densities of the master and non-master gels were calculated in the BioImage® program following analysis. Gels with a correction factor <1 have a higher total optical density than the "master gel", e.g. in the 15% IEF DB, the total optical density of gel DB10=0.293×gel DB3. For the intra- and interassay analyses, correction factors were calculated between an arbitrarily selected gel and the 4 other gels. Comparison cannot be made between subgroups because gels with a correction factor of 1 not necessarily have the same intensity.

TABLE 4

Reproducibility of spot detection in 15% IEF and NEPHGE 2-DGE DB of neonatal rat islet proteins.

| | total no. of spots | spots in 5 of 5 gels | | spots in 4–5 of 5 gels | | spots in 3–5 of 5 gels | | spots in 2–5 of 5 gels | |
|---|---|---|---|---|---|---|---|---|---|
| | | no. | % | no. | % | no. | % | no. | % |
| IEF | | | | | | | | | |
| gel DB3 | 1325 | 1235 | 93.2 | 1299 | 98.0 | 1320 | 99.6 | 1325 | 100 |
| gel DB6 | 1352 | 1235 | 91.3 | 1322 | 97.8 | 1346 | 99.6 | 1352 | 100 |
| gel DB8 | 1293 | 1235 | 95.5 | 1276 | 98.7 | 1287 | 99.5 | 1292 | 99.9 |
| gel DB9 | 1355 | 1235 | 91.1 | 1319 | 97.3 | 1339 | 98.8 | 1355 | 100 |
| gel DB10 | 1411 | 1235 | 87.5 | 1327 | 94.0 | 1365 | 96.7 | 1398 | 99.1 |
| avg ± SD | | | 91.7 ± 3.0 | | 97.2 ± 1.8 | | 98.8 ± 1.2 | | 99.8 ± 0.4 |
| NEPHGE | | | | | | | | | |
| gel DB3 | 663 | 557 | 84.0 | 604 | 91.1 | 633 | 95.5 | 658 | 99.2 |
| gel DB6 | 605 | 557 | 92.1 | 584 | 96.5 | 598 | 98.8 | 604 | 99.8 |
| gel DB8 | 629 | 557 | 88.6 | 597 | 94.9 | 614 | 97.6 | 623 | 99.0 |
| gel DB9 | 634 | 557 | 87.9 | 601 | 94.8 | 617 | 97.3 | 630 | 99.4 |
| gel DB10 | 764 | 557 | 72.9 | 610 | 79.8 | 648 | 84.4 | 701 | 91.8 |
| avg ± SD | | | 85.1 ± 7.4 | | 91.4 ± 6.8 | | 94.8 ± 5.7 | | 97.8 ± 3.4 |

Construction of the 2-D gel database: neonatal rat islets from 5 different isolates were cultured for 24 h in RPMI 1640+ 0.5% HS, washed twice and labelled for 4 h with ($^{35}$S)-methionine. Following 2-DGE (see Materials and Methods) in one set of gels, the fluorographs were scanned and spots were identified and quantitated by the BioImage® program. Each gel was compared and matched to the arbitrarily selected "master gel" (gel DB10). For each gel, the table indicates the number and percentage of spots present in (from left to right) all gels, at least 4 of 5 gels, and at least 3 of 5 gels and at least 2 of 5 gels.

TABLE 5

Reproducibility of spot detection in 10% IEF and NEPHGE 2-DGE DB of neonatal rat islet proteins.

| | total no. of spots | spots in 5 of 5 gels | | spots in 4–5 of 5 gels | | spots in 3–5 of 5 gels | | spots in 2–5 of 5 gels | |
|---|---|---|---|---|---|---|---|---|---|
| | | no. | % | no. | % | no. | % | no. | % |
| IEF | | | | | | | | | |
| gel DB1 | 1101 | 995 | 90.4 | 1060 | 96.3 | 1070 | 97.2 | 1072 | 97.4 |
| gel DB4 | 1200 | 995 | 82.9 | 1094 | 91.2 | 1143 | 95.3 | 1163 | 96.9 |
| gel DB6 | 1120 | 995 | 88.8 | 1075 | 96.0 | 1106 | 98.8 | 1108 | 98.9 |
| gel DB8 | 1119 | 995 | 88.9 | 1084 | 96.9 | 1106 | 98.8 | 1113 | 99.5 |
| gel DB10 | 1198 | 995 | 83.1 | 1106 | 92.3 | 1162 | 97.0 | 1193 | 99.6 |
| avg ± SD | | | 86.8 ± 3.5 | | 94.5 ± 2.6 | | 97.4 ± 1.5 | | 98.5 ± 1.2 |
| NEPHGE | | | | | | | | | |
| gel DB1 | 516 | 378 | 73.3 | 438 | 84.9 | 475 | 92.1 | 489 | 94.8 |
| gel DB7 | 462 | 378 | 81.8 | 424 | 91.8 | 442 | 95.7 | 445 | 96.3 |
| gel DB8 | 480 | 378 | 78.8 | 440 | 91.7 | 468 | 97.5 | 472 | 98.3 |
| gel DB9 | 492 | 378 | 76.8 | 441 | 89.6 | 474 | 96.3 | 482 | 98.0 |
| gel DB10 | 577 | 378 | 65.5 | 455 | 78.9 | 513 | 88.9 | 539 | 93.4 |
| avg ± SD | | | 75.2 ± 6.3 | | 87.4 ± 5.5 | | 94.1 ± 3.5 | | 96.2 ± 2.1 |

Construction of the 2-D gel database: neonatal rat islets form 5 different isolates were cultured for 24 h in RPMI 1640+ 0.5% HS, washed twice and labelled for 4 with ($^{35}$S)-methionine. Following 2-DGE (see Materials and Methods) in one set of gels, the fluorographs were scanned and spots were indentified and quantitated by the BioImage® program. Each gel was compared and matched to the arbitrarily selected "master gel" (gel DB10). For each gel, the table indicates the number and percentage of spots present in (from left to right) all gels, at least 4 of 5 gels, at least 3 of 5 gels and at least 2 of 5 gels.

TABLE 6

Reproducibility of spot detection in replicate 15% IEF and NEPHGE 2-D gels of neonatal rat islet proteins.

| Intraassay analysis | total no. of spots | spots in 5 of 5 gels no. | % | Interassay analysis | total no. of spots | spots in 5 of 5 gels no. | % |
|---|---|---|---|---|---|---|---|
| IEF | | | | IEF | | | |
| gel IA2 | 1289 | 1085 | 84.2 | gel IE3 | 1319 | 1082 | 82.0 |
| gel IA3 | 1337 | 1085 | 81.2 | gel IE4 | 1348 | 1082 | 80.3 |
| gel IA4 | 1289 | 1085 | 84.2 | gel IE8 | 1333 | 1082 | 81.2 |
| gel IA6 | 1303 | 1085 | 83.3 | gel IE9 | 1342 | 1082 | 83.2 |
| gel IA10 | 1326 | 1085 | 81.8 | gel IE10 | 1300 | 1082 | 80.6 |
| avg ± SD | | | 82.9 ± 1.4 | avg ± SD | | | 81.5 ± 1.2 |
| NEPHGE | | | | | | | |
| gel IA1 | 526 | 345 | 65.6 | gel IE3 | 574 | 421 | 75.0 |
| gel IA2 | 542 | 345 | 63.7 | gel IE4 | 589 | 421 | 73.3 |
| gel IA3 | 538 | 345 | 64.1 | gel IE8 | 566 | 421 | 71.5 |
| gel IA4 | 565 | 345 | 61.1 | gel IE9 | 590 | 421 | 74.4 |
| gel IA5 | 450 | 345 | 76.7 | gel IE10 | 561 | 421 | 71.4 |
| avg ± SD | | | 66.2 ± 6.1 | avg ± SD | | | 73.1 ± 1.6 |

For intraassay analysis, 5 independent gels of the same islet cell lysate were analyzed in one set of gels. For interassay analysis, 5 independent gels of the same islet cell lysate were analyzed in consecutive sets of gels on different days. Different islet isolates were used for database, intra- and interassay analysis. When analyzed in the BioImage® program, the fluorographs were compared and matched to the 15% IEF of the NEPHGE "master gel" of Table 2.

TABLE 7

Average coefficients of variance of % integrated optical density of spots detectable in 5 of 5 gels in databases and replicate 2-D gels of neonatal rat islet proteins.

| Analysis | Average CV% | Median (Range) CV% |
|---|---|---|
| IEF 15% DB | 45.4 ± 25.0 | 39.9 (5.0–165.3) |
| IEF 15% Interassay | 36.1 ± 19.8 | 32.6 (2.7–190.6) |
| IEF 15% Intraassay | 30.2 ± 17.1 | 27.3 (0.0–130.4) |
| NEPHGE 15% DB | 44.3 ± 22.5 | 42.0 (3.9–155.1) |
| NEPHGE 15% Interassay | 35.5 ± 19.7 | 33.1 (2.2–118.5) |
| NEPHGE 15% Intraassay | 45.7 ± 22.8 | 43.9 (4.3–130.9) |
| IEF 10% DB | 45.7 ± 21.3 | 42.7 (3.0–133.4) |
| NEPHGE 10% DB | 42.4 ± 22.4 | 37.7 (7.3–167.9) |

The average coefficient of variance (CV%) was calculated from the CV% of %IOD of all spots present in 5 of 5 gels in each subgroup of analysis. Results are presented as means±SD (left column) and as medians (ranges). The number of spots in 5 of 5 gels in each subgroup is shown in Tables 2–4. For details of design databases and replicate analyses, please see Materials and Methods.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which this invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method step s, conventional methods step s, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A computer-implemented method for identifying or characterizing qualitative or quantitative changes in affected proteins and for distinguishing unaffected cells and proteins expressed by unaffected cells from affected cells and proteins expressed by said affected cells wherein said unaffected and/or affected cells have either been treated or immunologically or pathologically affected, in vitro or in vivo, and wherein said unaffected and/or affected cells are derived from a sample of a specific cell type, cell line, tissue or physiological sample, said sample subjected to two dimensional gel electrophoresis (2DGE) to provide a 2DGE gel comprising unaffected and/or affected proteins, said method comprising (1) capturing a new image of said electrophoresis gel containing at least one protein, wherein said new image contains an undetermined position and integrated optical density percentage (IOD%) corresponding to each said protein;

(2) generating a master composite image which is used to analyze the new image, wherein the master composite image contains a plurality of master composite spots, each master composite spot being defined by at least an IOD% and a position;

(3) generating a master composite spot data list, wherein the master composite spot data list comprises at least a position, an IOD%, a unique spot identifier, and the variability of the spot for the position and IOD%, for each of the plurality of master composite spots;

(4) aligning the new image with the master composite image;

(5) determining the position and IOD% of new image spots corresponding to proteins using the spot data information from the master composite image to guide the search for and identification of new image spots that have a position that is within a position tolerance of the position of the corresponding master composite spots and that have an IOD% that is within an IOD% tolerance of the IOD% of corresponding master composite spots to form a set of matched new image spots corresponding to unaffected proteins;

(6) determining the position and IOD% of new image spots corresponding to proteins using the spot data information from the master composite image to guide the search for and identification of new image spots that have a position that is within a position tolerance of the position of the corresponding master composite spots but that have an IOD% that is outside the IOD% tolerance of the IOD% of corresponding master composite spots, to form a set of matched new image spots corresponding to affected proteins; and (7) searching the image outside of the set of matched new image spots to determine the position and IOD% of unidentified new image spots corresponding to proteins, wherein the spots detected in steps 6 and 7 represent affected proteins.

2. A method according to claim 1, further comprising:
generating a database which contains information selected from the group consisting of the type of sample analysed; the type of cells; the type of organism; the type of condition, disease or infection and the extent thereof; the type and amount of treatment of the organism; the type of proteins in the database; the characteristics or identity of said proteins; the manner in which the sample has been collected and treated; the type of experimentation done on the sample or the proteins; and the type of information already present in the database.

3. A method according to claim 1, wherein said aligning comprises: (i) selecting a set of anchor points from the master composite spot data list; and (ii) detecting new image spots that have a position that is within a position tolerance of the position of corresponding anchor points and that have an IOD% that is within an IOD% tolerance of the IOD% of corresponding anchor points, and matching the detected new image spots to the corresponding anchor points to form a set of matched new image spots.

4. A method according to claim 3, further comprising:
calculating a set of vectors linking spots of the same number in the master composite image and in the new gel image; and determining for each vector the length and angle.

5. A method according to claim 4, further comprising:
calculating a vector difference for each of the set of matched new image spots to form a set of vector differences, and removing from the set of matched new image spots those matched new image spots for which the vector difference falls within a predetermined percentage of largest vector differences within the set of vector differences to form a set of unmatched new image spots.

6. A method according to claim 5, further comprising:
selecting a set of well-defined spots from the master composite spot data list, detecting new image spots that have a position that is within a position tolerance of the position of corresponding well-defined spots, matching the detected new image spots to the corresponding well-defined spots, and adding the matched new image spots to the set of matched new image spots.

7. A method according to claim 6, further comprising:
selecting a set of saturated spots from the master composite spot data list, detecting new image spots that have a position that is within a position tolerance of the position of corresponding saturated spots, matching the detected new image spots to the corresponding saturated spots, and adding the matched new image spots to the set of matched new image spots.

8. A method according to claim 7, further comprising:
selecting a set of weak spots from the master composite spot data list, detecting new image spots that have a position that is within a position tolerance of the position of corresponding weak spots, matching the detected new image spots to the corresponding weak spots, and adding the matched new image spots to the set of matched new image spots.

9. The method of claim 1, wherein step (2) comprises:
(1) determining a set of selected images, wherein each selected image in the set has a plurality of spots that correspond to corresponding spots in the other selected images, and
(2) averaging the set of selected images, wherein the averaging comprises
　(i) subtracting the local background from each spot of the set of selected images,
　(ii) averaging the IOD% of corresponding spots in the set of selected images to form an average composite IOD% for each master composite spot data list,
　(iii) averaging a physical shape of corresponding spots in the set of selected images to form an average physical shape for each master composite spot data list,
　(iv) averaging the spot position of corresponding spots in the set of selected images to form an average spot position for each master composite spot data list,
　(v) computing a standard deviation for the average composite IOD% for each master composite spot data list, and
　(vi) computing a standard deviation for the average spot position for each master composite spot data list.

10. The method of claim 1, wherein step (4) comprises:
(a) identifying a common anchor point, wherein the common anchor point corresponds to a new image and to a master composite spot data list common anchor spot;

(b) determining the position of the master composite spot data list common anchor spot;

(c) determining the position of the new image common anchor spot; and (d) applying a position correction so that the position of the new image common anchor spot is aligned with the position of the master composite spot data list common anchor spot.

11. The method of claim 10, further comprising:

(e) determining a spot identifier for the master composite spot data list common anchor spot; and (f) assigning the new image common anchor spot a spot number that is the same as the spot identifier for the master composite spot data list common anchor spot.

12. The method of claim 2, further comprising comparing in a set of images, the IOD% for each spot against a value, or values, entered into the database and comparing a first set of images to a second set of images.

13. The method of claim 12, wherein the step of comparing a first set of images to a second set of images comprises:

(a) computing a statistical average of IOD% for each spot in the first set;

(b) computing a statistical average of IOD% for each spot in the second set; and (c) determining if each spot in the first set is statistically different from each spot in the second set.

14. A method according to claim 1, wherein said qualitative changes are changes in the structure of at least one of said proteins in said 2DGE gel.

15. A method according to claim 1, wherein said quantitative changes are changes in the amount of at least one of said proteins in said 2DGE gel.

16. A method according to claim 2, wherein said at least one characteristic is selected from the group consisting of pI, molecular weight, %IOD, amino acid sequence, mass spectra protein identity and a protein modification.

17. A method according to claim 1, wherein said cell type or cell line is derived from a prokaryotic or eukaryotic cell.

18. A method according to claim 17, wherein said eukaryotic cell is a mammalian cell, an insect cell or bird cell.

19. A method according to claim 1, wherein said treated cells have been treated with at least one compound prior to providing said cell sample.

20. A method according to claim 19, wherein said compound is selected from the group consisting of a protein, a nucleic acid and a chemical compound.

21. A method according to claim 19, wherein said compound is a potential drug.

22. A method according to claim 1, wherein said cells are derived from an organ, tissue, biopsy, or cell culture.

23. A computer-based system for identifying or characterizing unaffected proteins and for identifying or characterizing qualitative or quantitative changes in affected proteins which are either up regulated or down regulated and for distinguishing unaffected cells and proteins expressed by said unaffected cells from affected cells and proteins expressed by said affected cells wherein said unaffected and/or affected cells have either been treated or pathologically affected, in vitro or in vivo, and wherein said unaffected and/or affected cells are derived from a sample of a specific cell type, cell line, tissue or physiological sample, said sample subjected to two-dimensional gel electrophoresis (2DGE) to provide a 2DGE gel comprising said unaffected and/or affected proteins, said system comprising:

(a) a computer readable medium having stored thereon at least one image or composite image of at least a portion of said 2DGE gel comprising said unaffected and/or affected proteins, said proteins being resolvable as spots in said image or composite image;

(b) at least one computing subroutine which, when executed on a computer, causes the computer to analyze said image or composite image according to the computer-implemented method of claim 1, to provide output data representing at least one of said unaffected or affected proteins, wherein said image or composite image, when used to compare images or composite images of said unaffected proteins and affected proteins, identifies (i) qualitative or quantitative changes in at least one of said affected proteins; or (ii) at least one identifying characteristic of at least one of said affected proteins;

(c) retrieval means for recording said output data comprising said image or composite image, wherein the output data comprises at least one image or composite image selected from the group consisting of:

(1) an unaffected partial image or unaffected composite image corresponding to at least one of said unaffected proteins in said gel, said unaffected partial image or unaffected composite image comprising images of at least one of the unaffected proteins having the corresponding molecular weights and pIs; or data tables, graphs, histograms, dendrograms or other means of representation of the data, or part of the data shown in (i) or (ii) above; and (2) an affected partial image or affected composite image corresponding to at least one of said affected proteins in said gel, said affected partial image or affected composite image comprising images of at least one of the affected proteins having the corresponding molecular weights and pIs; and wherein said at least one characteristic of at least one of said proteins is selected from the group consisting of pI, molecular weight, reliability coefficients for the positional and quantitative data for each spot, shape information, local background level, amino acid sequence, IOD%, mass spectra and a protein modification, protein identity or other information selected from the database.

24. A computer system according to claim 23, wherein said analyzing utilizes at least one computing subroutine selected from the group consisting of data processing and reduction, optical density processing and integration, intensity scaling, intensity merging, positional anchoring and refinement, background analysis, protein coordinate analysis, protein spot identification using boundary or shape characterization with normal, low or high sensitivity, protein spot matching, auto-indexing, statistical analysis, rubber sheeting and vector analysis.

25. A computer system according to claim 23, wherein said qualitative or quantitative changes are changes in the structure of at least one of said proteins in said 2DGE gel.

26. A computer system according to claim 23, wherein said quantitative changes are changes in the amount of at least one of said proteins in said 2DGE gel.

27. A computer system according to claim 23, wherein said at least one characteristic is selected from the group consisting of pI, molecular weight, amino acid sequence, mass spectra and a protein modification.

28. A computer system according to claim 23, wherein said treated cells have been treated with at least one compound prior to providing said cell sample.

29. A computer system according to claim 28, wherein said compound is selected from the group consisting of a protein, a nucleic acid and a chemical compound.

30. A computer system according to claim 23, wherein said pathologically affected cells have been obtained from organs, tissues, biopsies, body fluids, primary secondary or established cell lines, and includes their secreted proteins.

31. A computer system according to claim 28, wherein said compound is a potential drug.

32. A computer system according to claim 31, wherein said potential drug is selected from the group consisting of an antagonist, an agonist, an antibody, a protein and a chemical compound.

33. A method for identifying or characterizing unaffected proteins and for identifying or characterizing qualitative or quantitative changes in affected proteins which are either up regulated or down regulated and for distinguishing unaffected cells and proteins expressed by said unaffected cells from affected cells and proteins expressed by said affected cells wherein said unaffected and/or affected cells have either been treated or pathologically affected, in vitro or in vivo, and wherein said unaffected and/or affected cells are derived from a sample of a specific cell type, cell line, tissue or physiological sample, said sample subjected to two-dimensional gel electrophoresis (2DGE) to provide a 2DGE gel comprising said unaffected or affected proteins, said method comprising (a) providing a computer readable medium having stored thereon at least one image or composite image of at least a portion of said 2DGE gel comprising said unaffected and/or affected proteins, said proteins being resolvable as spots in said image or in said composite image;

(b) analyzing according to the computer-implemented method of claim 1, on a computer using at least one computing subroutine executed in said computer, said at least one image or composite image, to provide output data representing at least one of said unaffected or affected proteins, wherein said image or composite image, when used to compare images or composite images of said unaffected and affected proteins, identifies (i) qualitative or quantitative changes in at least one of said affected proteins; or (ii) at least one identifying characteristic of at least one of said affected proteins;

(c) obtaining said output data comprising said image or composite image, wherein the output data comprises at least one image or composite image selected from the group consisting of:

(1) a partial unaffected image or unaffected composite image corresponding to at least one of said unaffected proteins in said gel, said partial unaffected image or unaffected composite image comprising images of at least one of the unaffected proteins having the corresponding molecular weights and pIs; or data tables, graphs, histograms, dendrograms or other means of representation of the data, or part of the data shown in (i) or (ii) above; and (2) a partial affected image or affected composite image corresponding to at least one of said affected proteins in said gel, said partial affected image or affected composite image comprising images of at least one of the affected proteins having the corresponding molecular weights and pIs; and wherein said at least one characteristic of at least one of said proteins is selected from the group comprising pI, molecular weight, amino acid sequence, IOD%, mass spectra and a protein modification.

34. A method according to claim 33, wherein said analyzing utilizes at least one computing subroutine selected from the group consisting of data processing and reduction, optical density processing and integration, intensity scaling, intensity merging, positional anchoring and refinement, background analysis, protein coordinate analysis, protein spot identification using boundary or shape characterization with normal, low or high sensitivity, protein spot matching, auto-indexing, statistical analysis, rubber sheeting and vector analysis.

35. A method according to claim 33, wherein said qualitative changes are changes in the structure of at least one of said proteins in said 2DGE gel.

36. A method according to claim 33, wherein said quantitative changes are changes in the amount of at least one of said proteins in said 2DGE gel.

37. A method according to claim 33, wherein said at least one characteristic is selected from the group consisting of pI, molecular weight, amino acid sequence, mass spectra and a post-translational modification.

38. A method according to claim 33, wherein said treated cells have been treated with at least one compound prior to providing said cell sample.

39. A method according to claim 38, wherein said compound is selected from the group consisting of a protein, a nucleic acid and a chemical compound.

40. A method according to claim 39, wherein said pathologically affected cells have been obtained from organs, tissues, biopsies, body fluids, primary secondary or established cell lines, and includes their secreted proteins.

41. A method according to claim 38, wherein said compound is a potential drug.

42. A method according to claim 41, wherein said potential drug is selected from the group consisting of an IL-1 antagonist, an IL-1 antibody, a protein agonist and a protein antagonist.

43. A computer-implemented method for identifying or characterizing qualitative or quantitative changes in affected proteins and for distinguishing unaffected cells and proteins expressed from said unaffected cells from affected cells and proteins expressed by said affected cells wherein said unaffected and/or affected cells have either been treated or immunologically or pathologically affected, in vitro or in vivo, and wherein said unaffected and/or affected cells are derived from a sample of a specific cell type, cell line, tissue or physiological sample, said sample subjected to two-dimensional gel electrophoresis (2DGE) to provide a 2DGE gel comprising said unaffected and/or affected proteins, said method comprising (1) capturing a new image of said electrophoresis gel containing at least one protein, wherein the new image contains a plurality of new image spots corresponding to at least one protein, each new image spot having an integrated optical density percentage (IOD%) and a position;

(2) generating a master composite image which is used to analyze the new image, wherein the master composite image contains a plurality of master composite spots, each master composite spot being defined by at least an IOD% and a position;

(3) generating a master composite spot data list, wherein the master composite spot data list comprises at least a position, an IOD%, a unique spot identifier, the variability of the spot for the position and IOD%, and a saturation value for each of the plurality of master composite spots;

(4) aligning the new image with the master composite image, said aligning comprising (i) selecting a set of anchor points from the master composite spot data list, and (ii) detecting new image spots that have a position that is within a position tolerance of the position of corresponding anchor points and that have an IOD% that is within an IOD% tolerance of the IOD% of corresponding anchor points, and matching the detected new image spots to the corresponding anchor points to form a set of matched new image spots;

(5) calculating a set of vectors linking spots of the same number in the master composite image and in the new gel image; and determining for each vector the length and angle;

(6) calculating the vector difference for each of the set of matched new image spots to form a set of vector differences, and removing from the set of matched new image spots those matched new image spots for which the vector difference falls within a predetermined percentage of the largest vector differences within the set of vector differences to form a set of unmatched new image spots;

(7) selecting a set of well-defined spots from the master composite spot data list, detecting new image spots that have a position that is within a position tolerance of the position of corresponding well-defined spots, matching the detected new image spots to the corresponding well-defined spots, and adding the matched new image spots to the set of matched new image spots;

(8) selecting a set of saturated spots from the master composite spot data list, detecting new image spots that have a position that is within a position tolerance of the position of the corresponding saturated spots, matching the detected new image spots to the corresponding saturated spots, and adding the matched new image spots to the set of matched new image spots;

(9) selecting a set of weak spots from the master composite spot data list, detecting new image spots that have a position that is within a position tolerance of the position of corresponding weak spots, matching the detected new image spots to the corresponding weak spots, and adding the matched new image spots to the set of matched new image spots; and

(10) searching the new image outside of the set of matched new image spots to locate unidentified new image spots.

44. The method of claim 1, wherein said master composite spot data list further comprises a saturation value for each of the plurality of master composite spots.

45. The method of claim 1, wherein said master composite spot data list further comprises as least one characteristic of at least one of said proteins, said characteristic selected from the group consisting of pI, molecular weight, reliability coefficients for the positional and quantitative data for each spot, shape information, local background level, amino acid sequence, mass spectra and a protein modification.

46. The method of claim 42, further comprising generating a database which contains information selected from the group consisting of the type of sample analyzed; the type of cells, the type of organism; the type of condition, disease or infection and the extent thereof; the type and amount of treatment of the organism; the type of proteins in the database; the characteristics or identity of said proteins; the manner in which the sample has been collected and treated; the type of experimentation done on the sample or the proteins; and the type of information already present in the database.

47. The computer-implemented method of claim 1, further comprising extracting one or more of the purified affected proteins from said gel.

48. A computer-based system according to claim 23, said computer readable medium further having stored thereon a database of information useful in the interpretation of the gel images, such information relating to the origin of the sample, its treatment, preparation and the conditions of the experiment, together with any form of data relating to specific protein spots on the gels.

49. A computer-based system according to claim 48, wherein said information is obtained from manual entry or downloading the data from other electronic media and networks.

50. A computer-based system according to claim 48, wherein said at least one computing subroutine causes the computer to analyze said image or composite image optionally with reference to the database.

51. A computer-based system according to claim 23, wherein said output data further comprises at least one marker image or marker composite image representing at least one marker protein present in each 2DGE gel from said unaffected or affected cells.

52. A computer-based system according to claim 51, wherein said marker proteins have the corresponding molecular weights and pIs.

53. A method according to claim 33, wherein said analyzing is performed with reference to a database of information useful in the interpretation of the gel images.

54. A method according to claim 33, wherein said output data further comprises at least one marker image or marker composite image representing at least one marker protein present in each 2DGE gel from said normal, treated or pathologically affected cells.

55. A method according to claim 54, wherein said output data further comprises a partial marker image or marker composite image corresponding to at least one of said marker proteins in said gel, said partial marker image or marker composite image comprising the images of at least one of the marker proteins having the corresponding molecular weights and pIs.

* * * * *